(12) United States Patent
Overes et al.

(10) Patent No.: US 9,554,789 B2
(45) Date of Patent: Jan. 31, 2017

(54) EXPANDABLE DILATOR

(71) Applicant: DePuy Synthes Products, Inc., Raynham, MA (US)

(72) Inventors: Tom Overes, Langendorf (CH); Silas Zurschmiede, Zuchwil (CH); Alfred Niederberger, Zuchwil (CH); Johann Fierlbeck, Salzburg (AT)

(73) Assignee: DePuy Synthes Products, Inc., Raynham, MA (US)

( * ) Notice: Subject to any disclaimer, the term of this patent is extended or adjusted under 35 U.S.C. 154(b) by 28 days.

(21) Appl. No.: 14/253,899

(22) Filed: Apr. 16, 2014

(65) Prior Publication Data
US 2014/0316209 A1    Oct. 23, 2014

Related U.S. Application Data

(60) Provisional application No. 61/812,877, filed on Apr. 17, 2013, provisional application No. 61/838,640, filed on Jun. 24, 2013, provisional application No. 61/838,630, filed on Jun. 24, 2013.

(51) Int. Cl.
*A61B 17/02*    (2006.01)
*A61B 17/34*    (2006.01)
*A61B 17/00*    (2006.01)

(52) U.S. Cl.
CPC ....... *A61B 17/0218* (2013.01); *A61B 17/0206* (2013.01); *A61B 17/0293* (2013.01); *A61B 17/3439* (2013.01); *A61B 90/30* (2016.02); *A61B 90/57* (2016.02); *A61B 2017/00261* (2013.01); *A61B 2017/0225* (2013.01); *A61B 2017/3443* (2013.01)

(58) Field of Classification Search
CPC ............ A61B 17/0218; A61B 17/3439; A61B 17/0206
See application file for complete search history.

(56) References Cited

U.S. PATENT DOCUMENTS

| | | |
|---|---|---|
| 5,707,359 A | 1/1998 | Bufalini |
| 5,772,661 A | 6/1998 | Michelson |
| 5,945,635 A | 8/1999 | Suzuki et al. |
| 6,187,000 B1 | 2/2001 | Davison et al. |
| 6,428,556 B1 | 8/2002 | Chin |
| 6,616,678 B2 * | 9/2003 | Nishtala ................ A61M 29/02 604/104 |
| 6,676,639 B1 * | 1/2004 | Ternstrom .......... A61B 17/3417 604/174 |
| 6,793,656 B1 | 9/2004 | Mathews |
| 6,800,084 B2 | 10/2004 | Davison et al. |
| 6,945,933 B2 | 9/2005 | Branch et al. |
| 7,056,321 B2 | 6/2006 | Pagliuca et al. |
| 7,108,705 B2 | 9/2006 | Davison et al. |
| 7,144,393 B2 | 12/2006 | DiPato et al. |

(Continued)

FOREIGN PATENT DOCUMENTS

| | | |
|---|---|---|
| WO | WO 2005/060837 | 7/2005 |
| WO | WO 2008/134288 A2 | 11/2008 |

(Continued)

*Primary Examiner* — Jacqueline Johanas
(74) *Attorney, Agent, or Firm* — Baker & Hostetler LLP

(57) ABSTRACT

Expandable dilators, dilation assemblies, and kits are disclosed, along with methods for using same.

21 Claims, 45 Drawing Sheets

(56) References Cited

U.S. PATENT DOCUMENTS

| | | | |
|---|---|---|---|
| 7,179,225 B2* | 2/2007 | Shluzas | A61B 17/3439 600/219 |
| 7,261,688 B2 | 8/2007 | Smith et al. | |
| 7,691,057 B2 | 4/2010 | Miles et al. | |
| 7,819,801 B2 | 10/2010 | Miles et al. | |
| 7,981,029 B2 | 7/2011 | Branch et al. | |
| 8,231,570 B2 | 7/2012 | Ortiz et al. | |
| 2004/0143167 A1* | 7/2004 | Branch | A61B 17/0218 600/212 |
| 2005/0075644 A1* | 4/2005 | DiPoto | A61B 1/3135 606/90 |
| 2005/0209627 A1* | 9/2005 | Kick | A61B 17/22 606/191 |
| 2005/0273132 A1* | 12/2005 | Shluzas | A61B 17/3439 606/198 |
| 2006/0106416 A1* | 5/2006 | Raymond | A61B 17/02 606/198 |
| 2006/0135981 A1* | 6/2006 | Lenker | A61B 17/3439 606/191 |
| 2006/0195017 A1* | 8/2006 | Shluzas | A61B 17/0218 600/210 |
| 2006/0229636 A1* | 10/2006 | Woodburn | A61B 17/02 606/108 |
| 2006/0271057 A1* | 11/2006 | Shluzas | A61B 1/00149 606/86 R |
| 2007/0038216 A1* | 2/2007 | Hamada | A61B 17/02 606/53 |
| 2007/0060939 A1* | 3/2007 | Lancial | A61B 1/00154 606/191 |
| 2007/0073112 A1* | 3/2007 | Holmes | A61B 17/02 600/225 |
| 2008/0039865 A1* | 2/2008 | Shaher | A61B 17/0206 606/119 |
| 2009/0024158 A1* | 1/2009 | Viker | A61B 17/0206 606/201 |
| 2009/0105546 A1* | 4/2009 | Hestad | A61B 17/0206 600/210 |
| 2009/0275802 A1* | 11/2009 | Hawkes | A61B 17/0218 600/219 |
| 2010/0041955 A1* | 2/2010 | Grey | A61B 1/267 600/212 |
| 2010/0211093 A1* | 8/2010 | Abbate | A61B 17/0218 606/196 |
| 2011/0144442 A1* | 6/2011 | Farrell | A61B 1/32 600/206 |
| 2011/0144443 A1* | 6/2011 | Shelton, IV | A61B 1/32 600/206 |
| 2011/0144448 A1* | 6/2011 | Shelton, IV | A61B 17/3423 600/216 |
| 2011/0282156 A1* | 11/2011 | Lenker | A61B 17/3439 600/208 |
| 2012/0022575 A1* | 1/2012 | Mire | A61B 5/4893 606/198 |
| 2012/0289785 A1* | 11/2012 | Albrecht | A61B 17/0293 600/208 |
| 2014/0039264 A1* | 2/2014 | Heiman | A61B 17/025 600/202 |
| 2014/0039494 A1* | 2/2014 | Kick | A61B 17/3478 606/46 |
| 2014/0058209 A1* | 2/2014 | Grey | A61B 17/02 600/212 |
| 2014/0088367 A1* | 3/2014 | DiMauro | A61B 17/025 600/202 |
| 2014/0275797 A1* | 9/2014 | Ibrahim | A61B 17/3439 600/208 |
| 2014/0303666 A1* | 10/2014 | Heiman | A61B 17/0218 606/198 |
| 2014/0316209 A1* | 10/2014 | Overes | A61B 17/0218 600/206 |

FOREIGN PATENT DOCUMENTS

| | | |
|---|---|---|
| WO | WO 2009/137700 | 11/2009 |
| WO | WO 2011/098989 | 8/2011 |
| WO | WO 2012/074884 | 6/2012 |
| WO | WO 2013/009382 A1 | 1/2013 |

\* cited by examiner

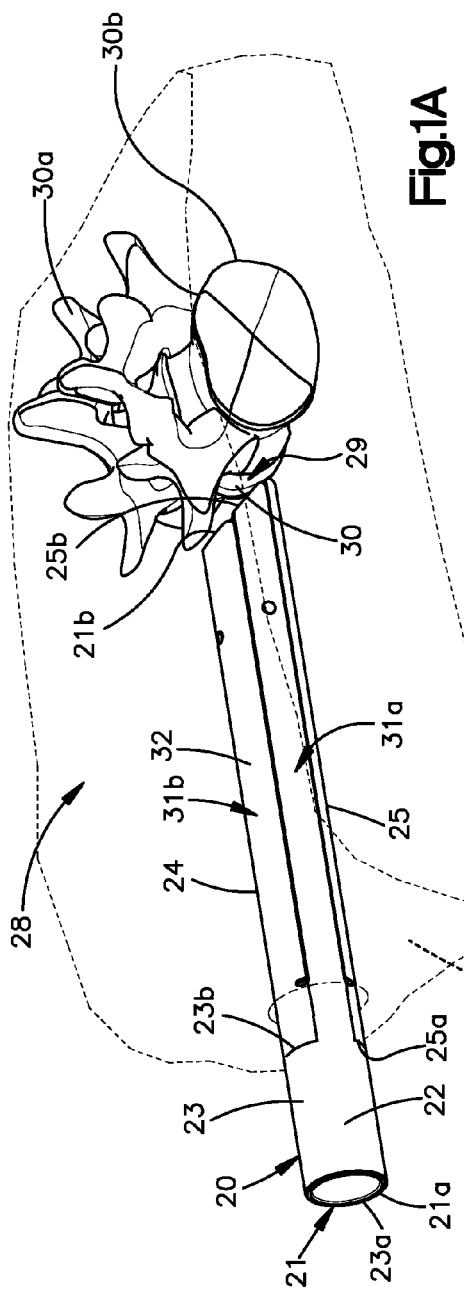
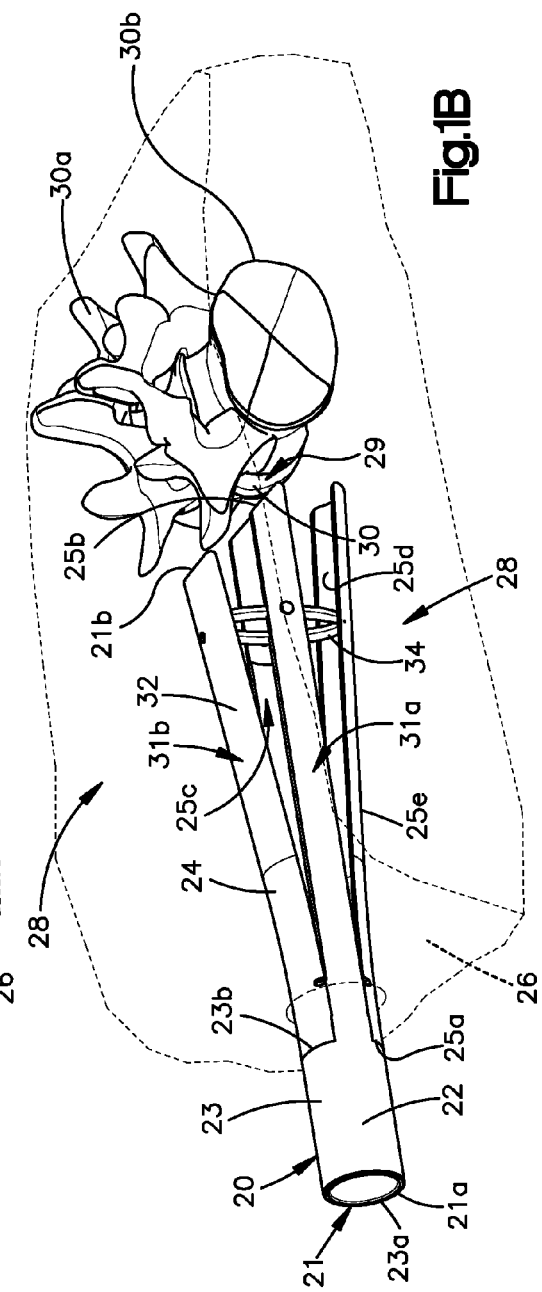

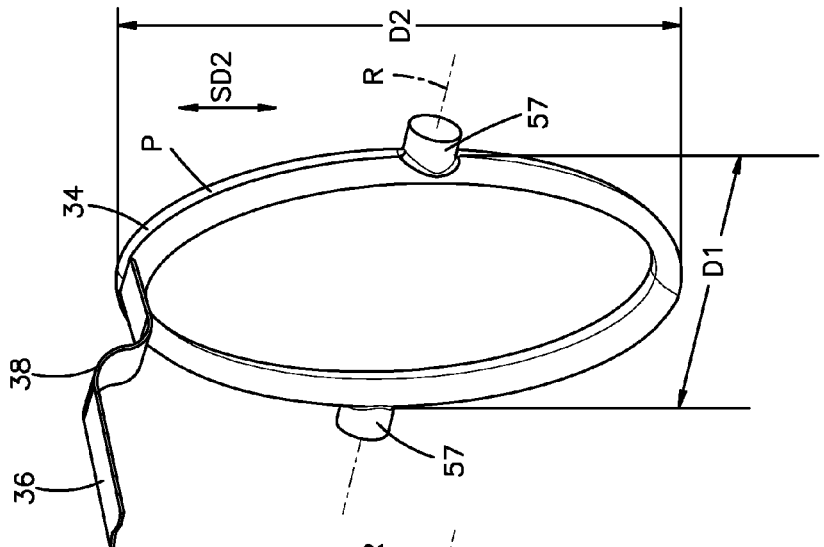
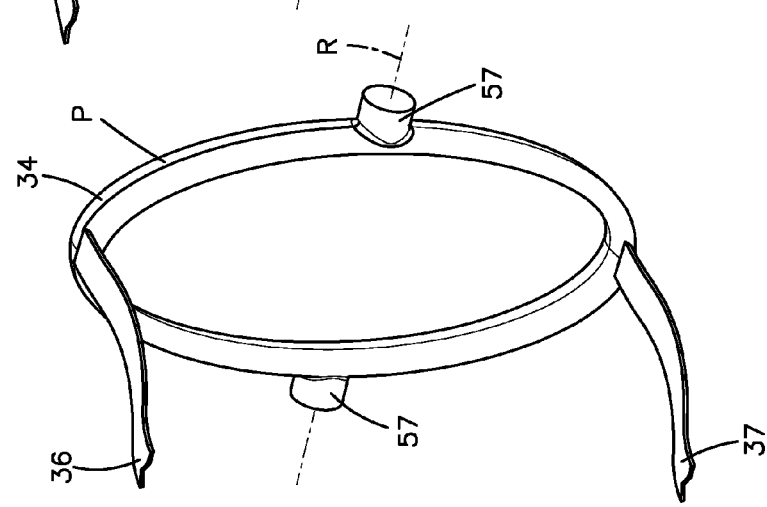
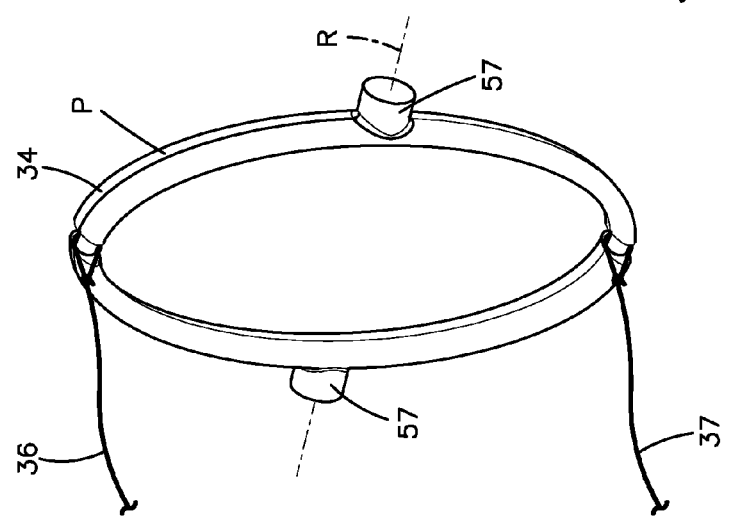

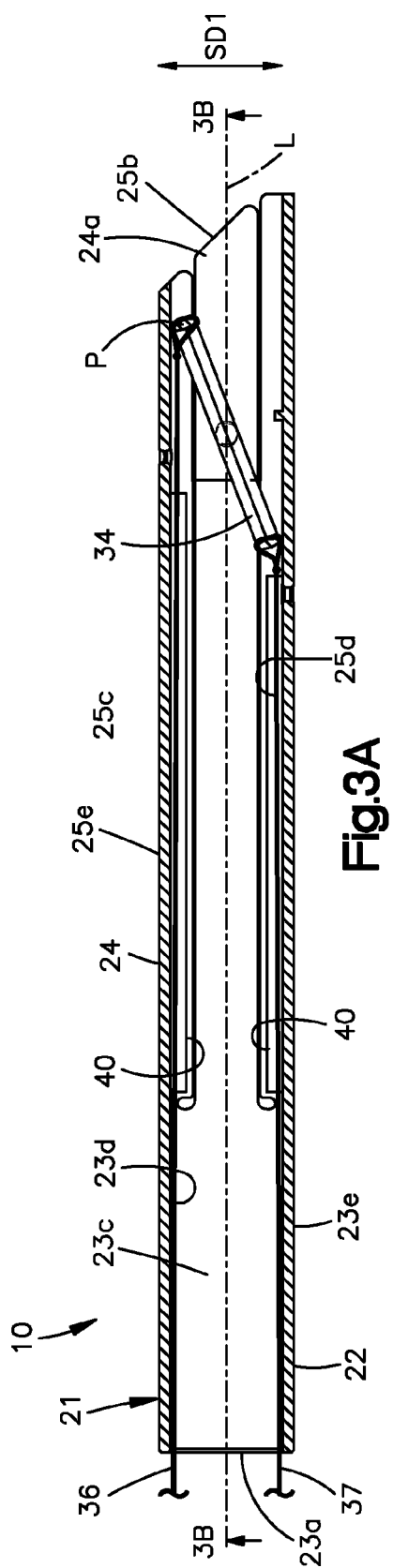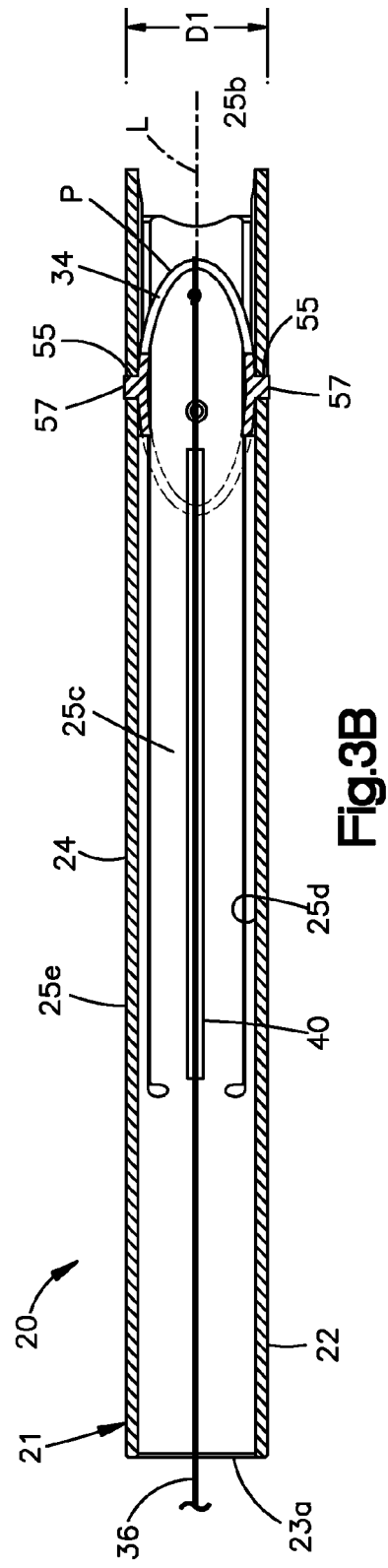

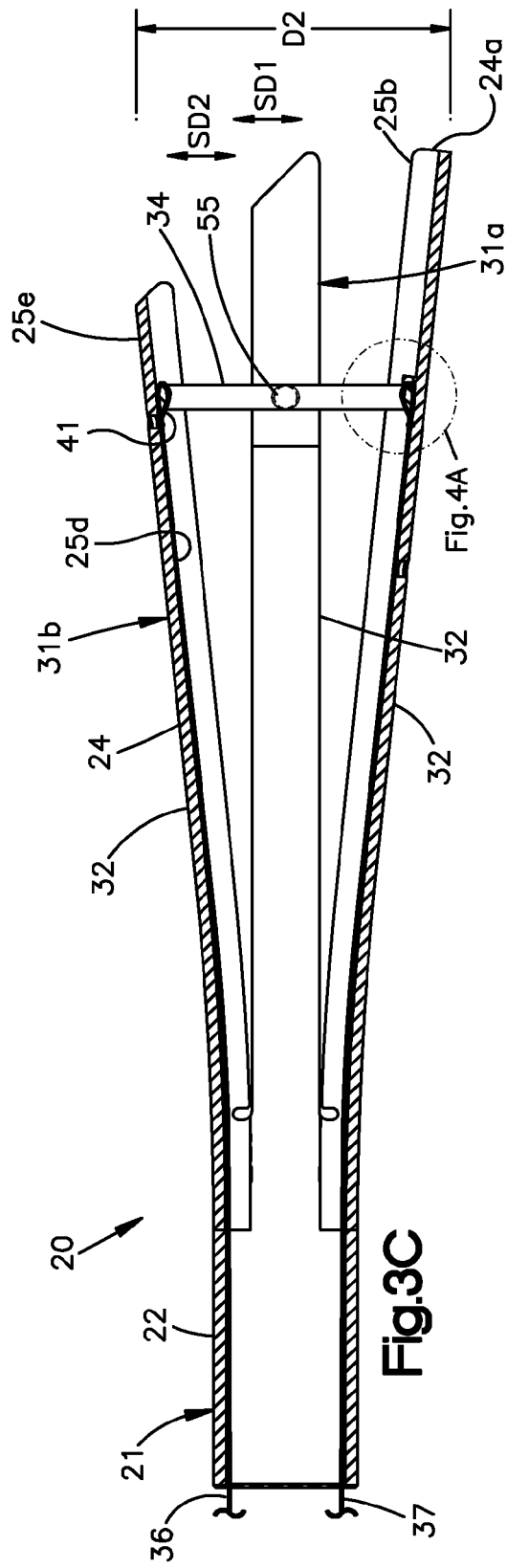

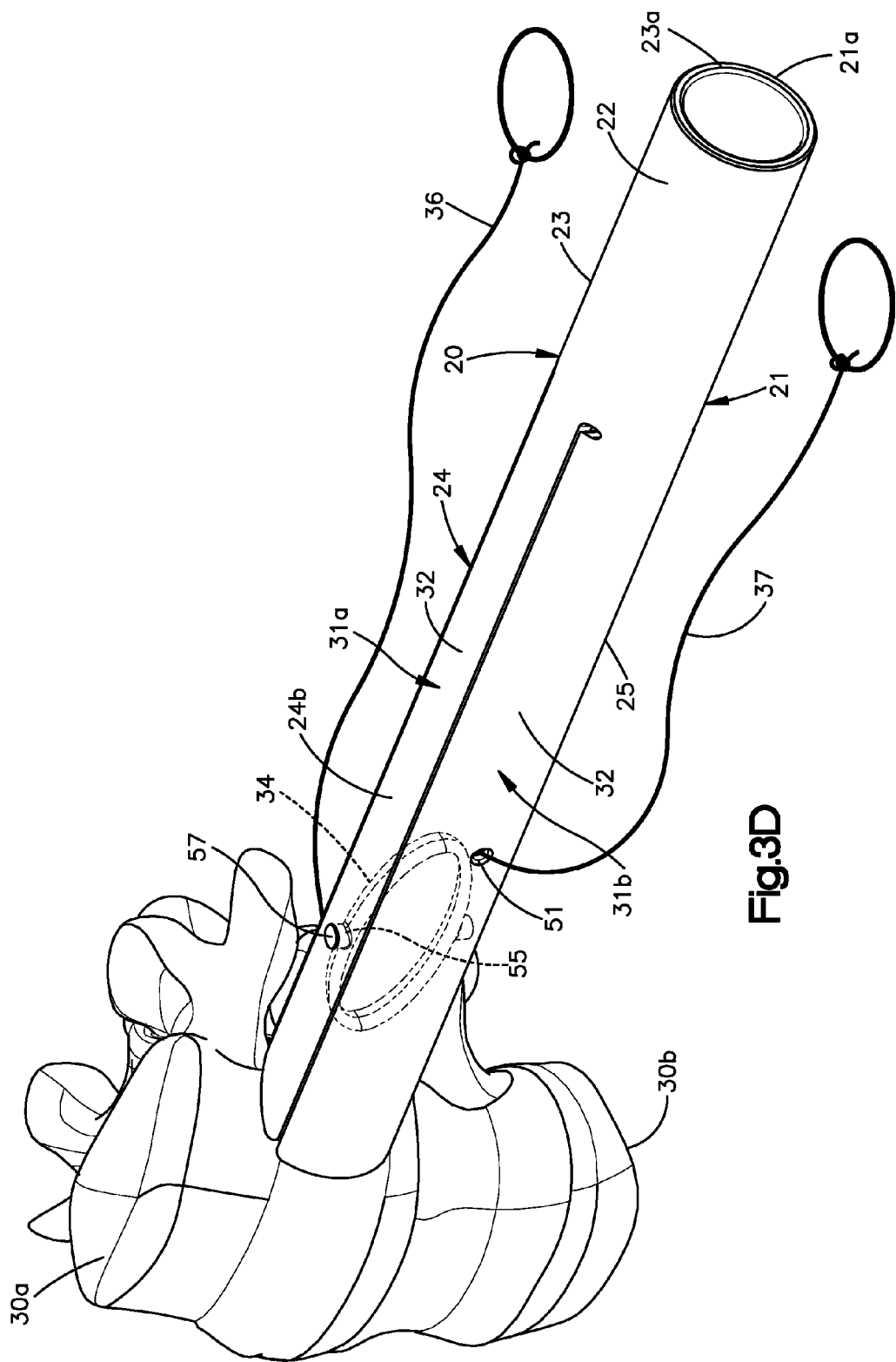

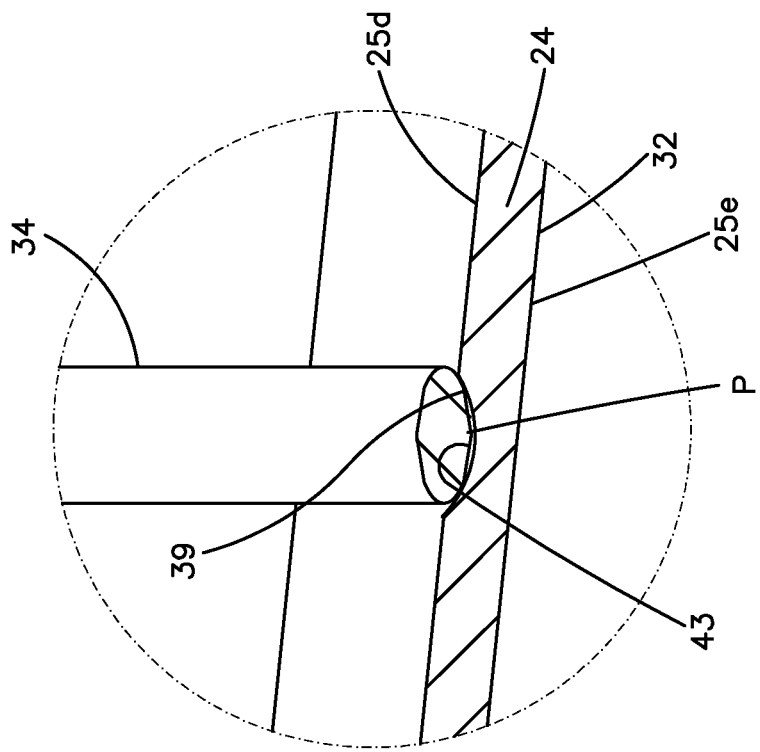
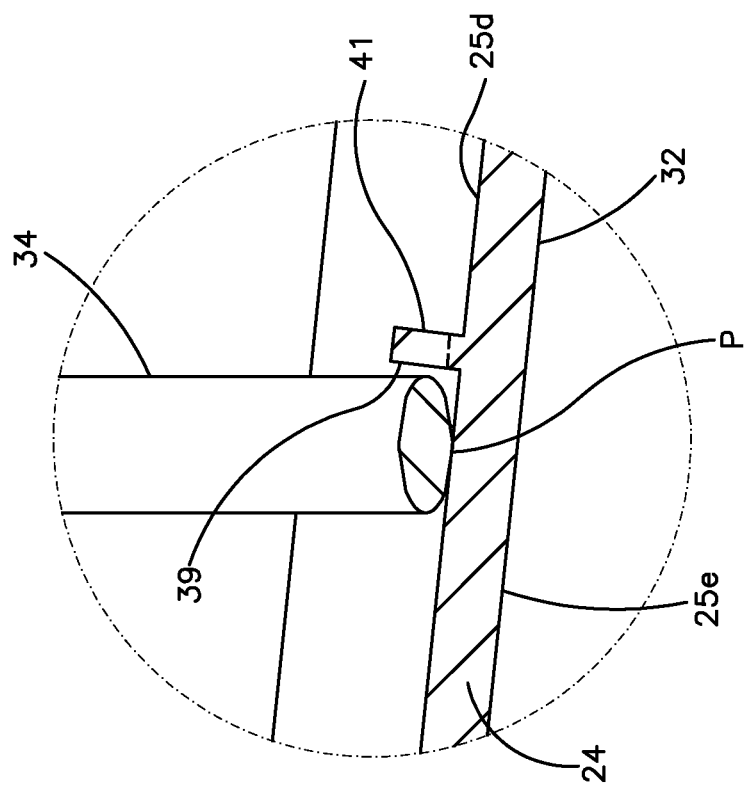

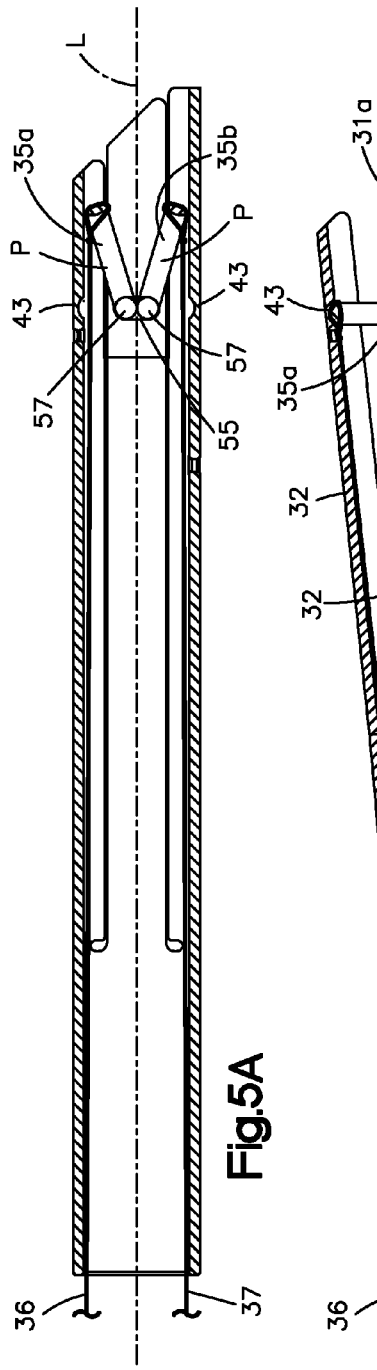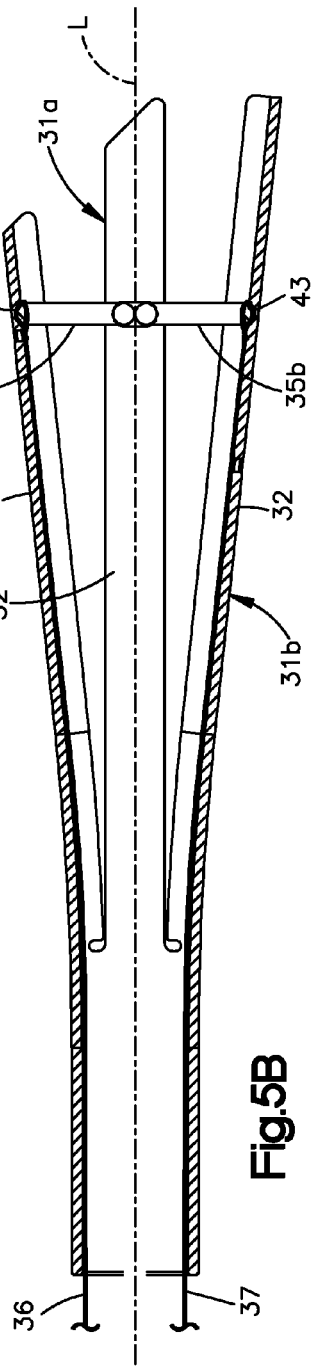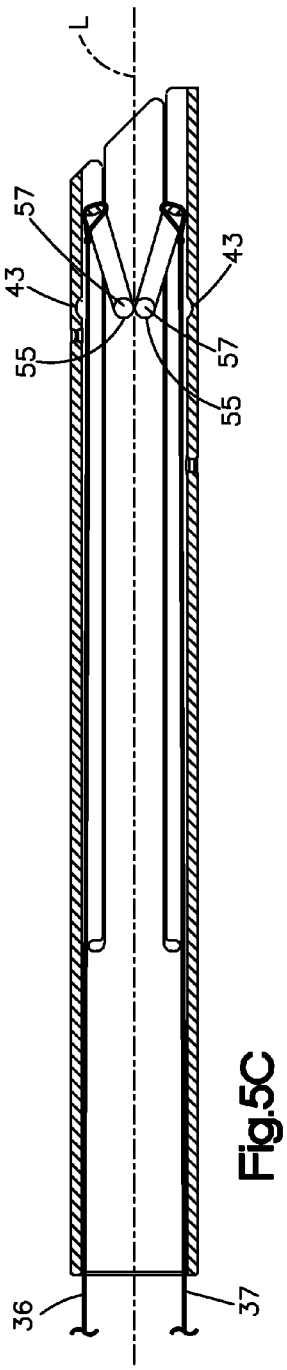

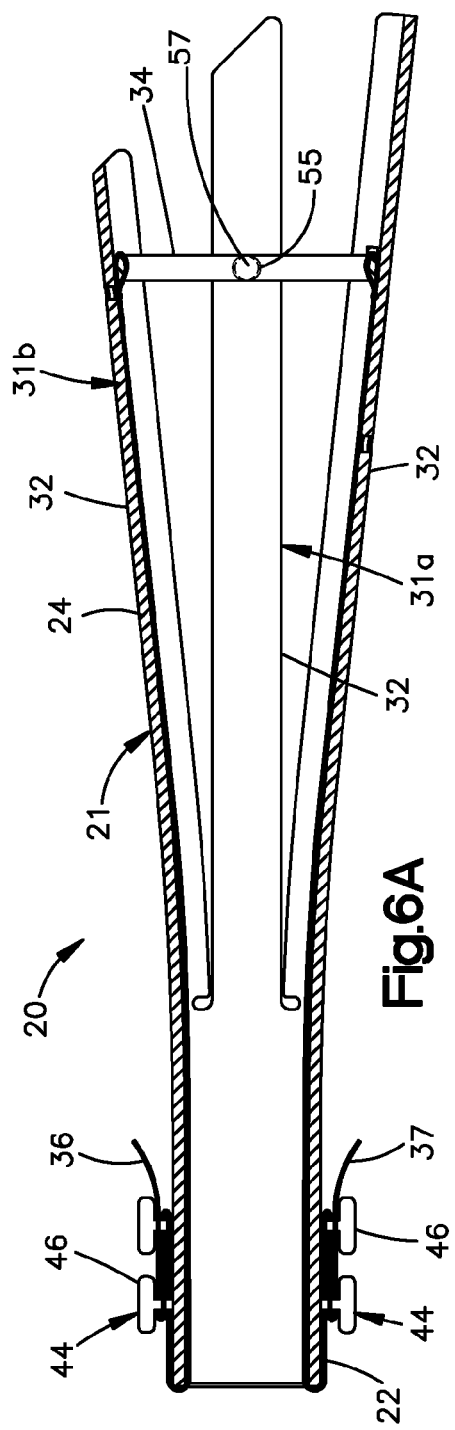
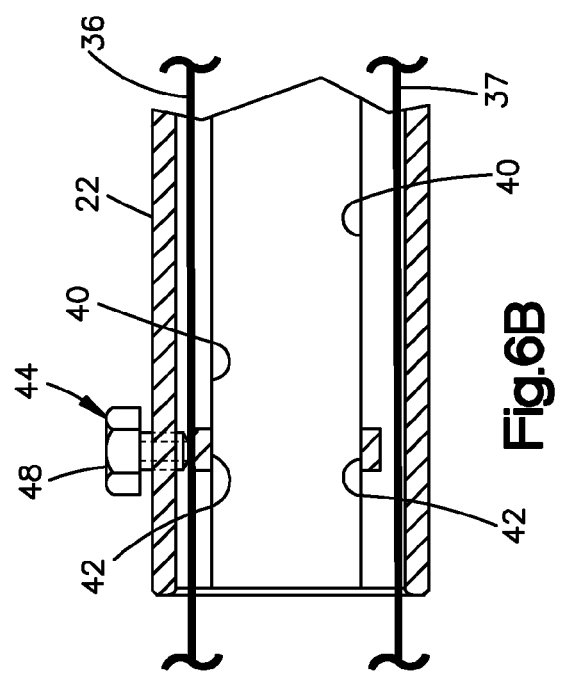
Fig.6A
Fig.6B

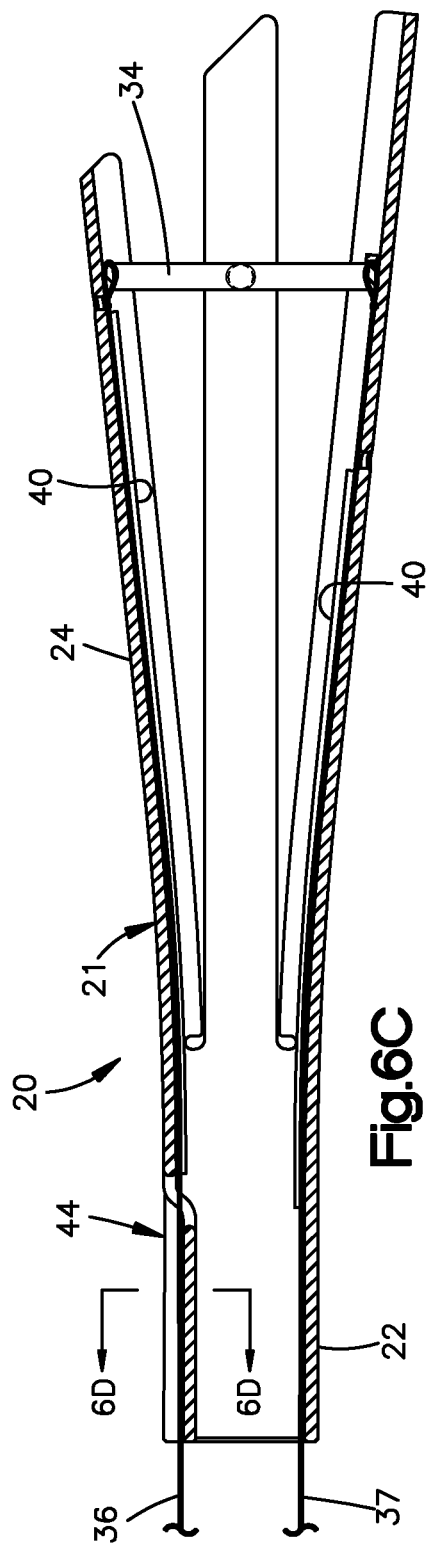
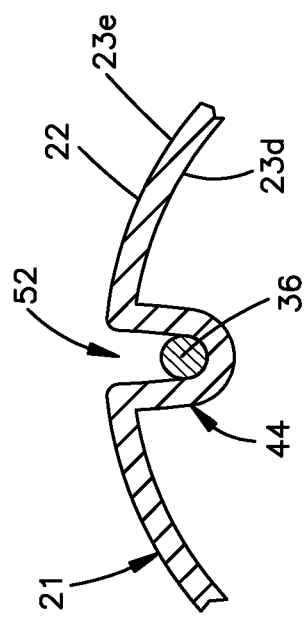

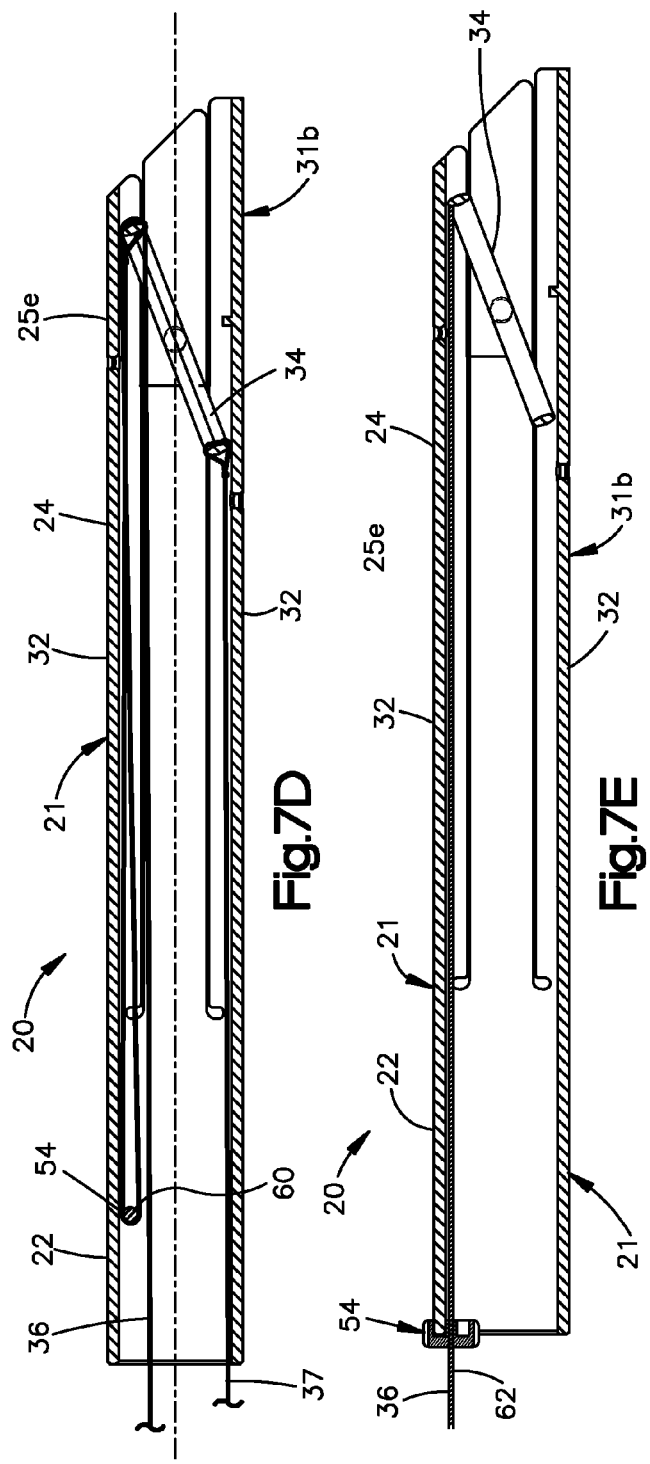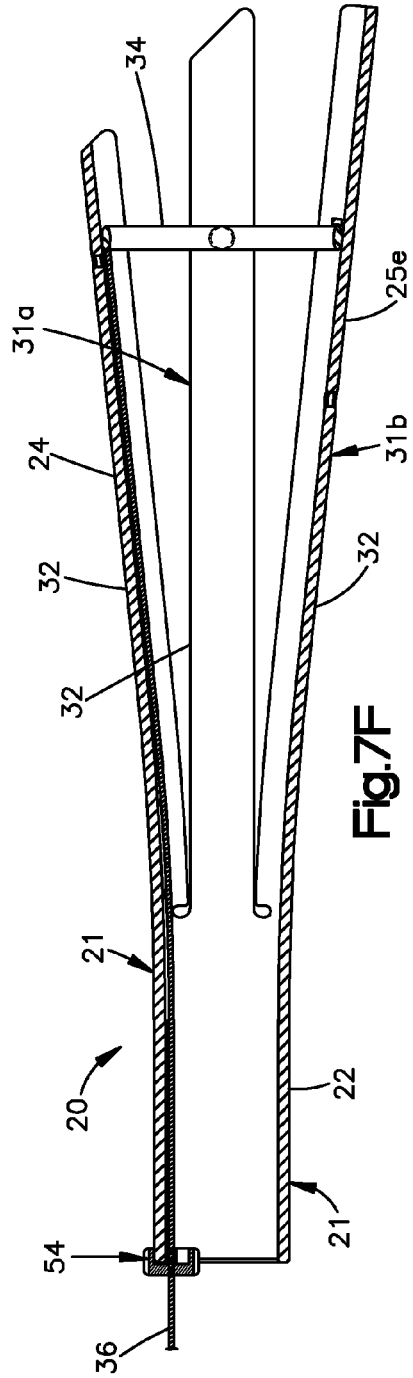

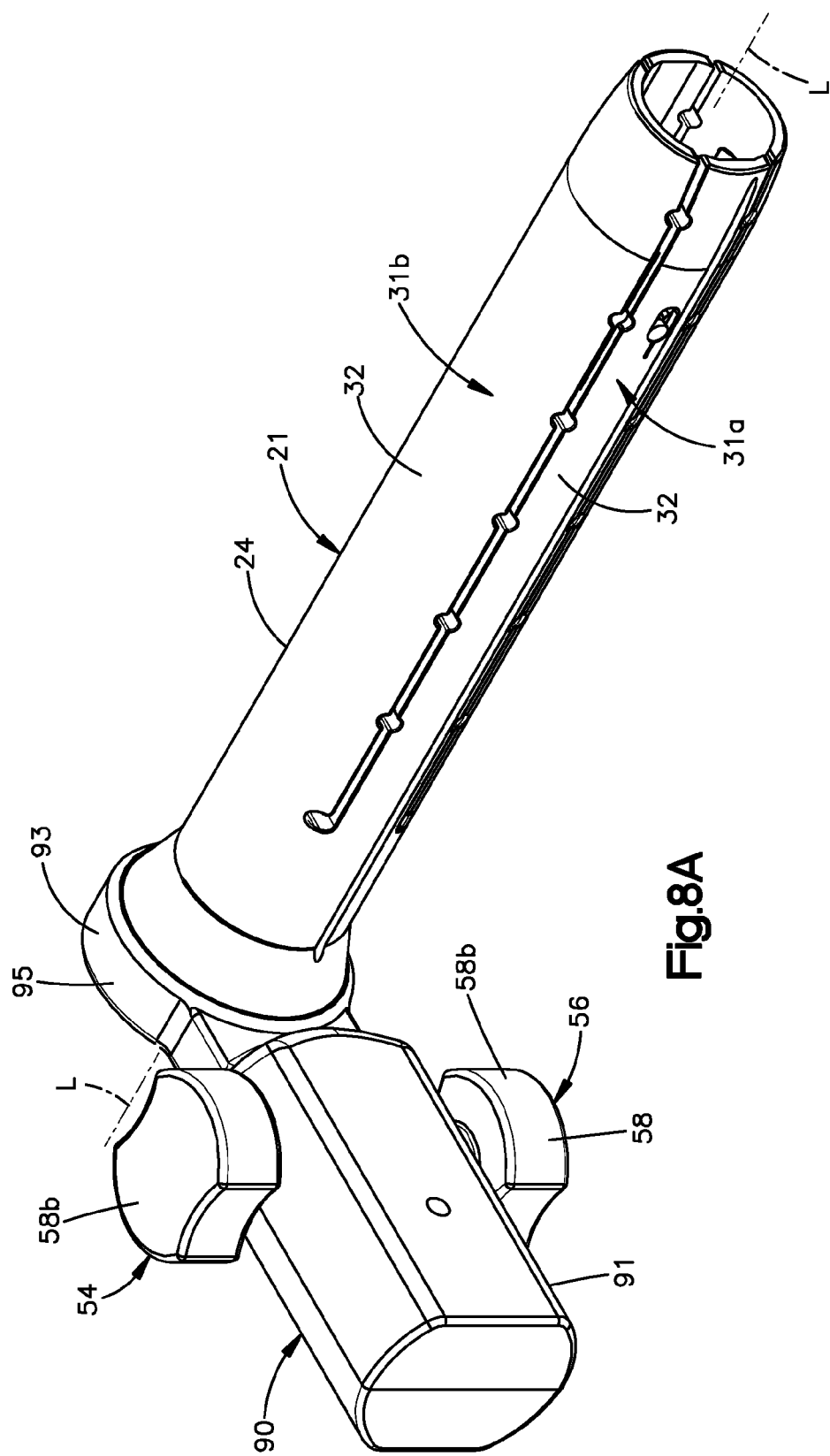

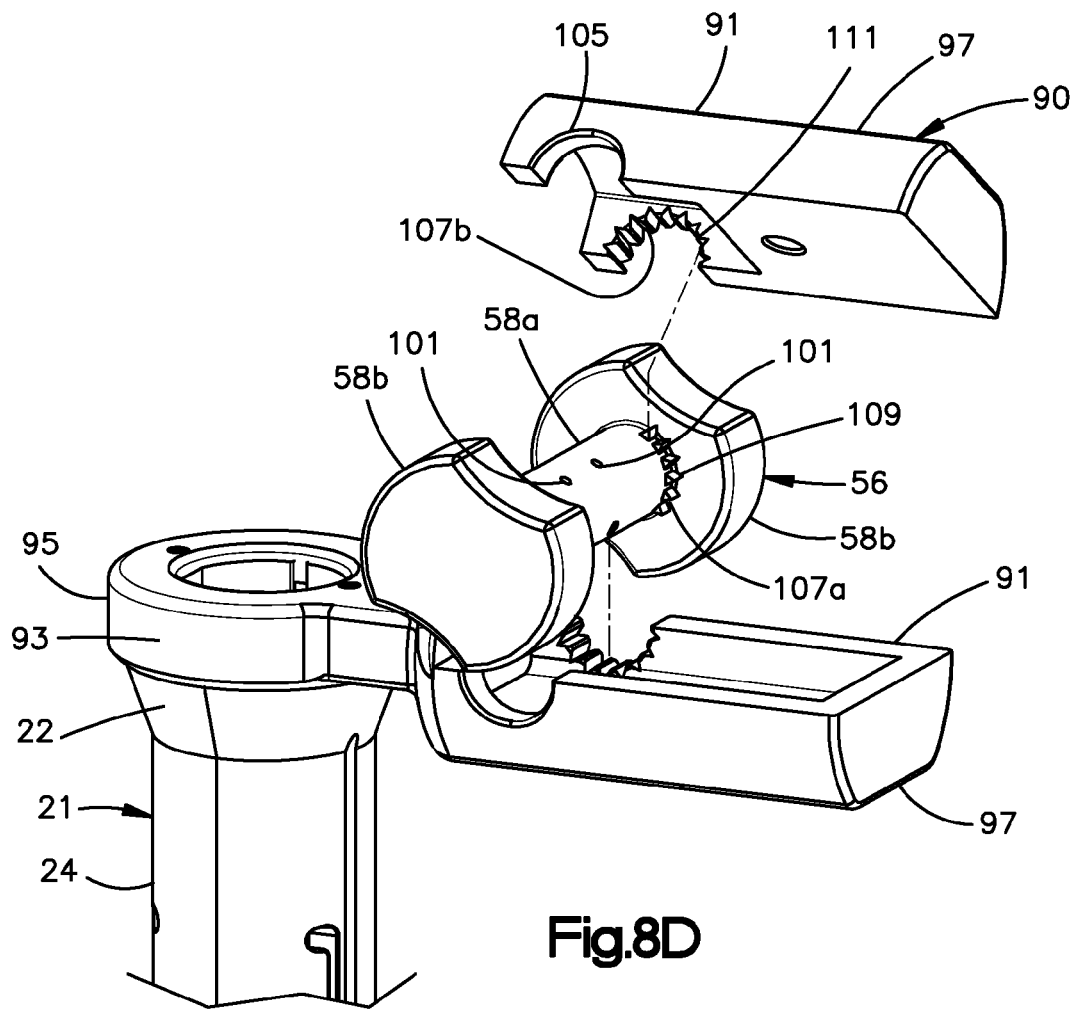
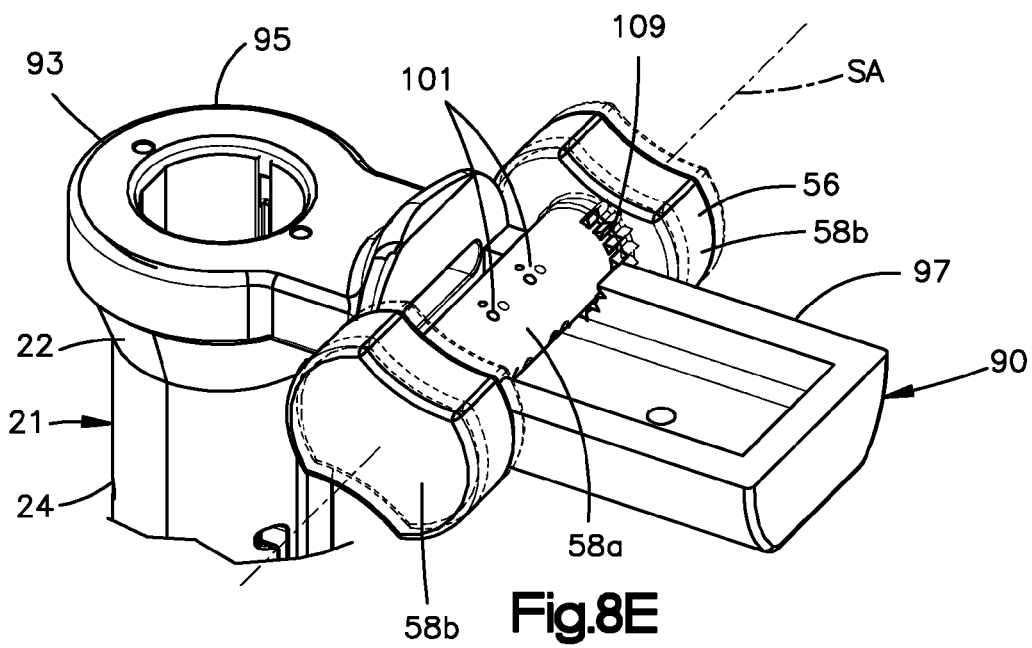

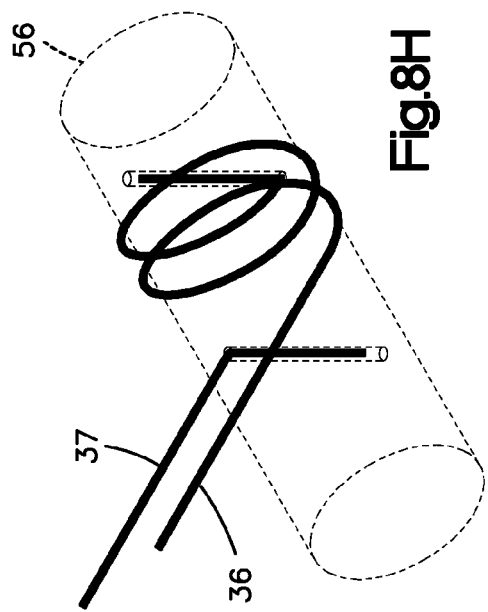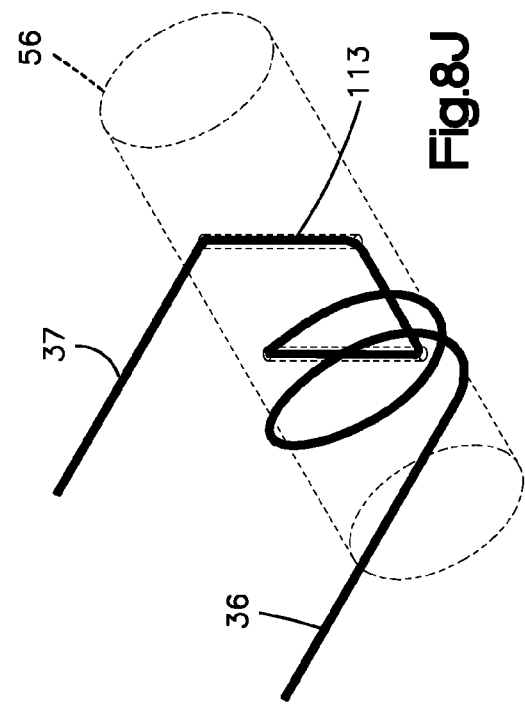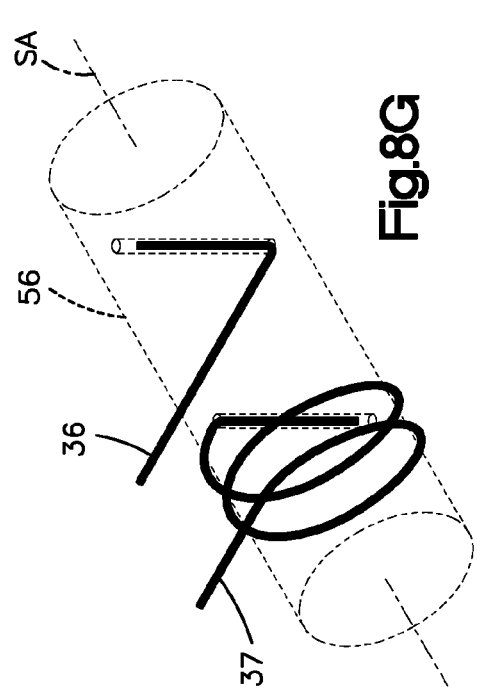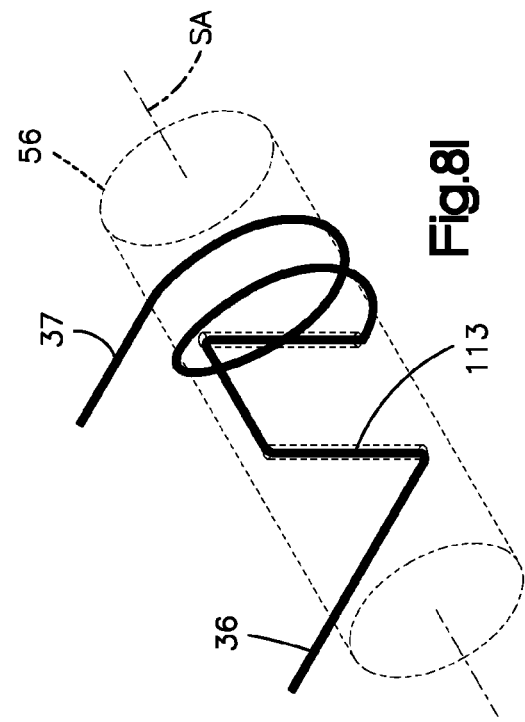

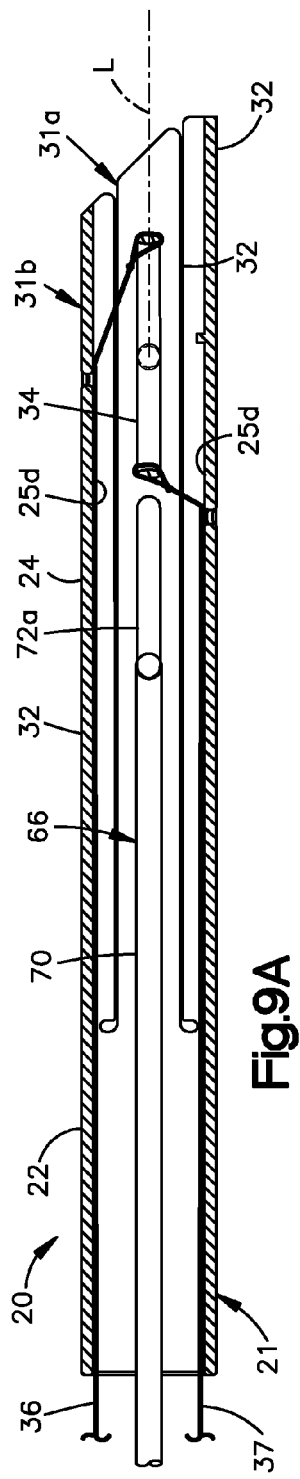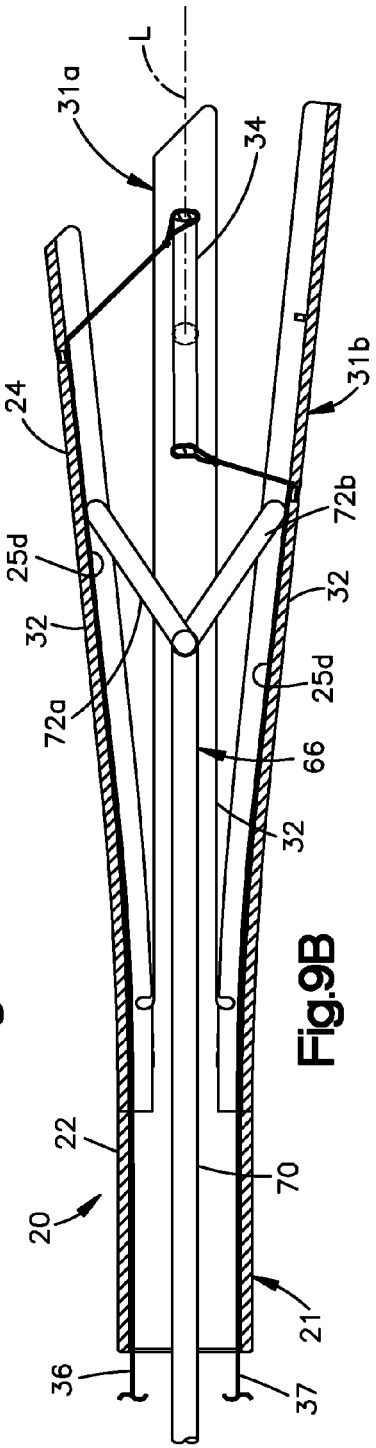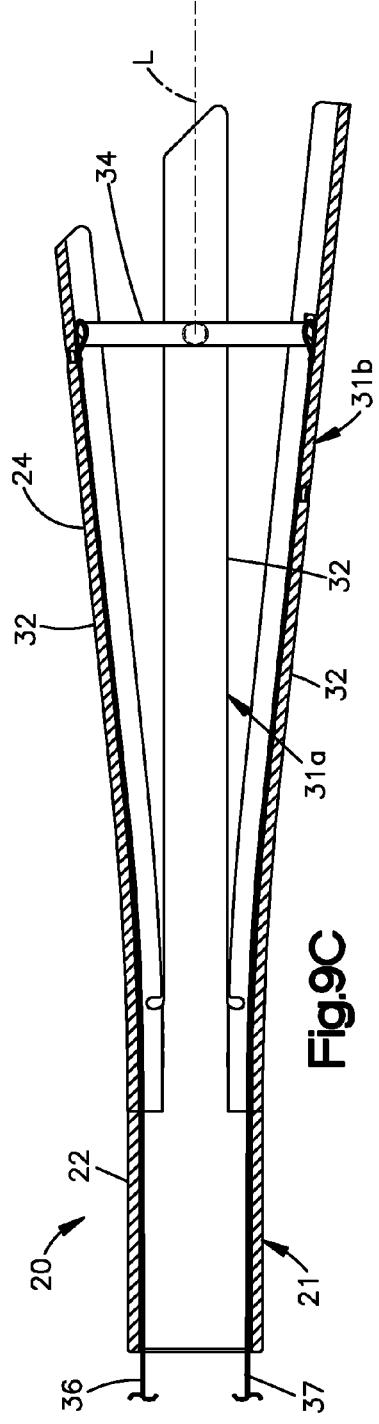

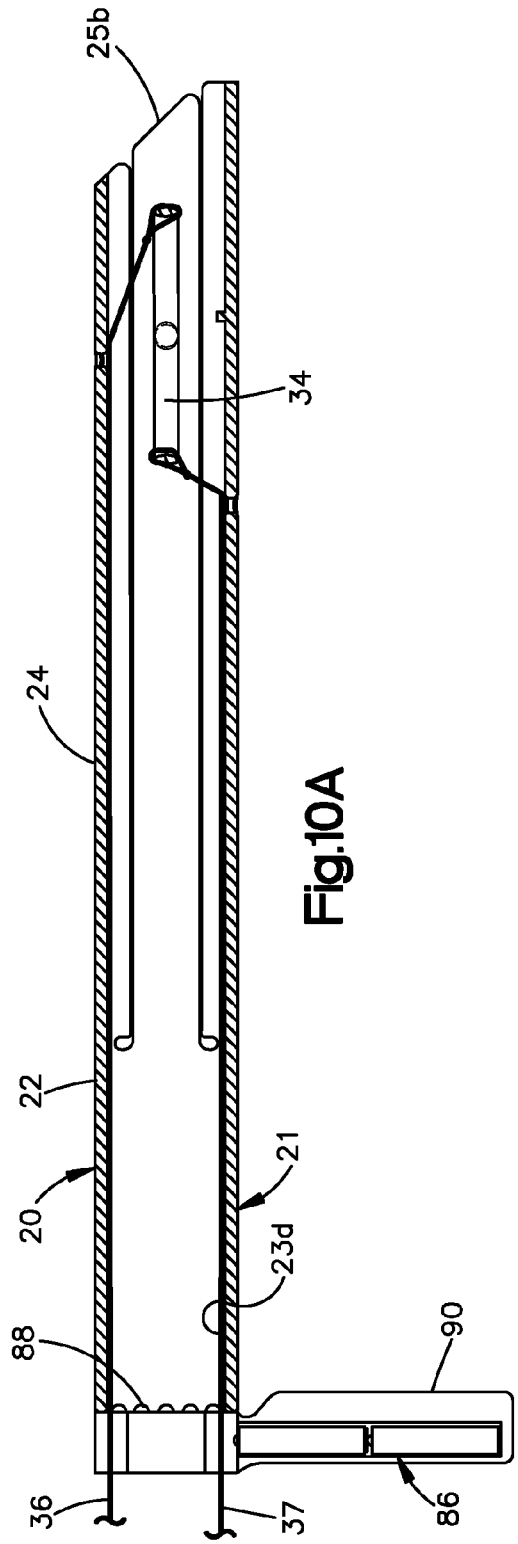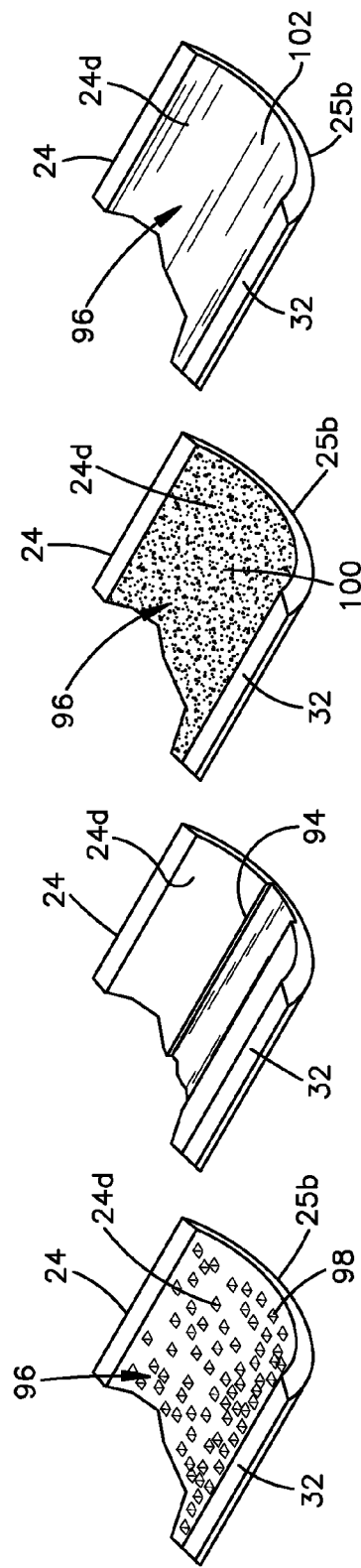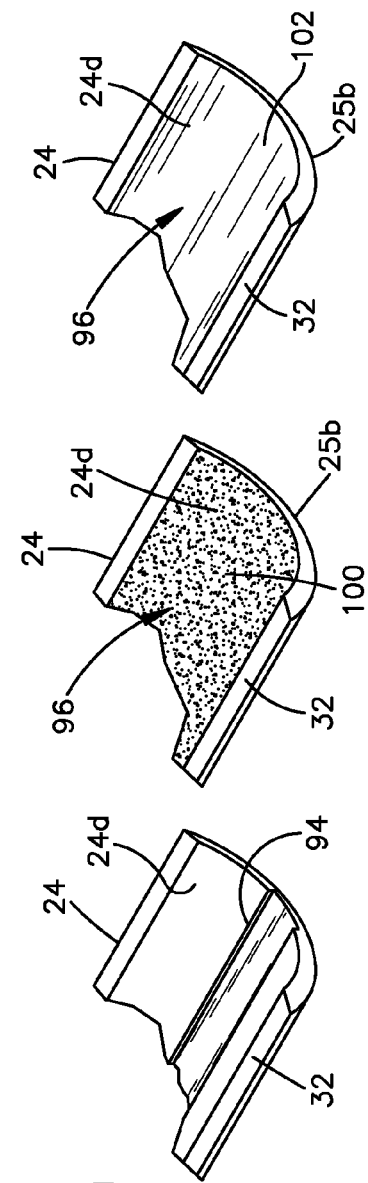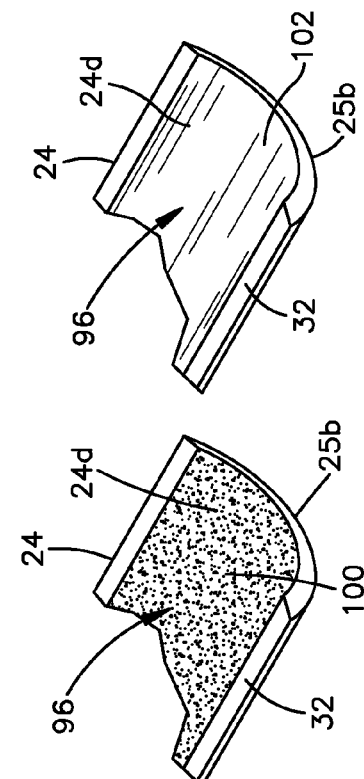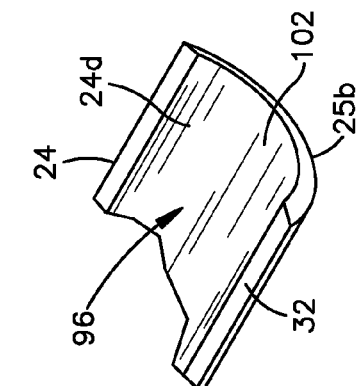

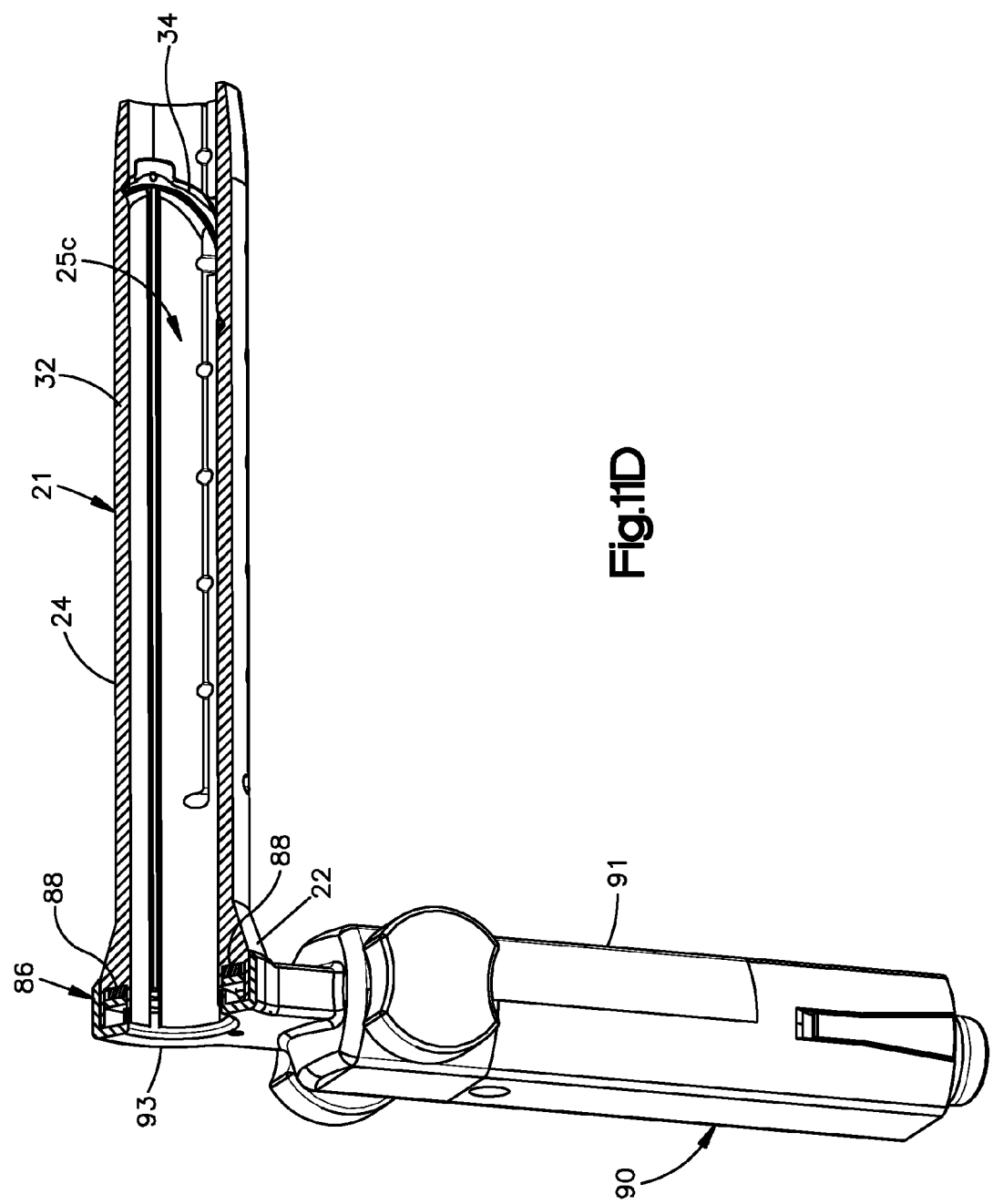

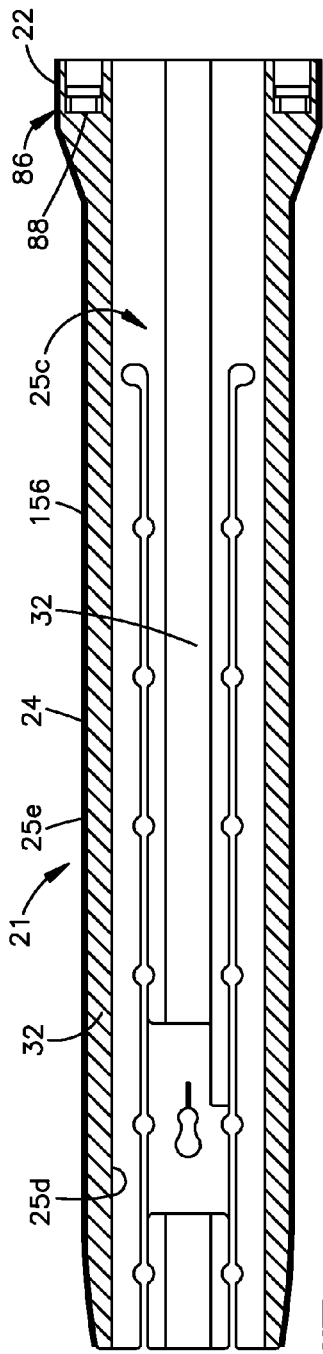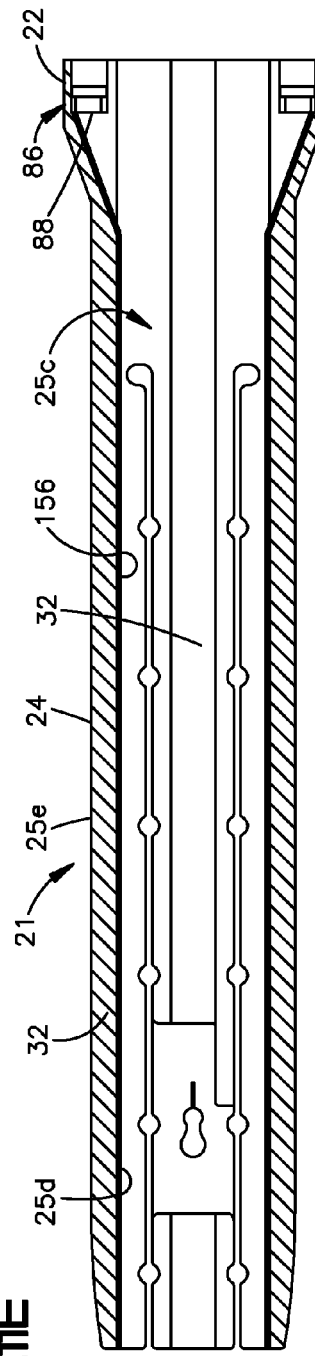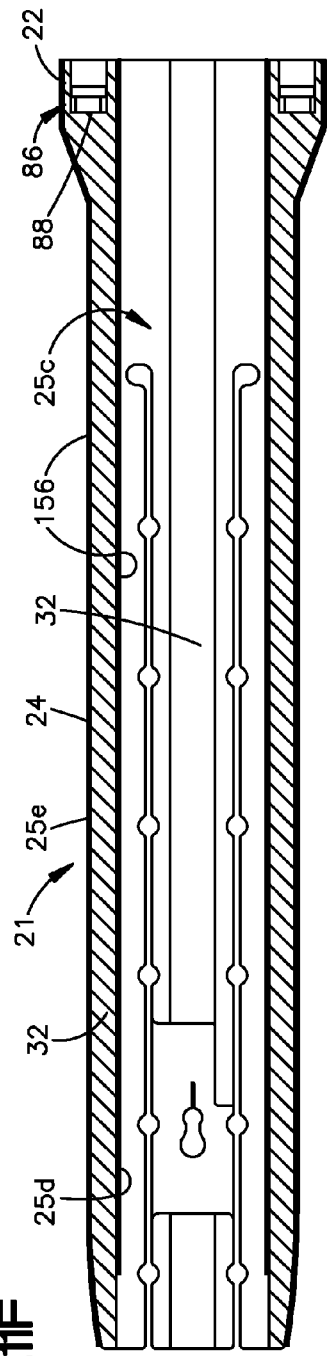

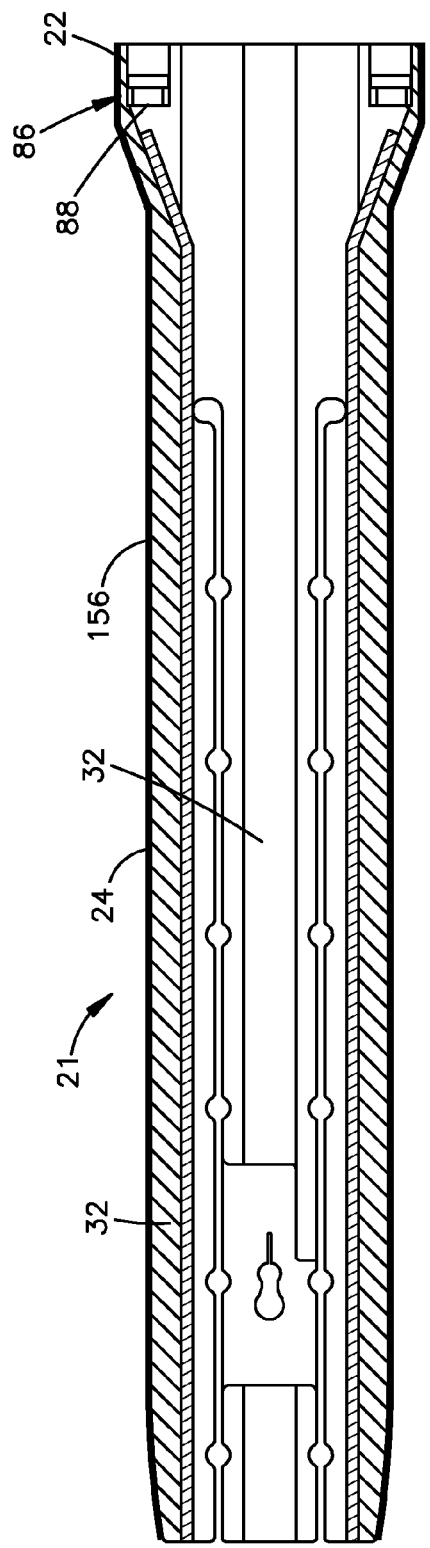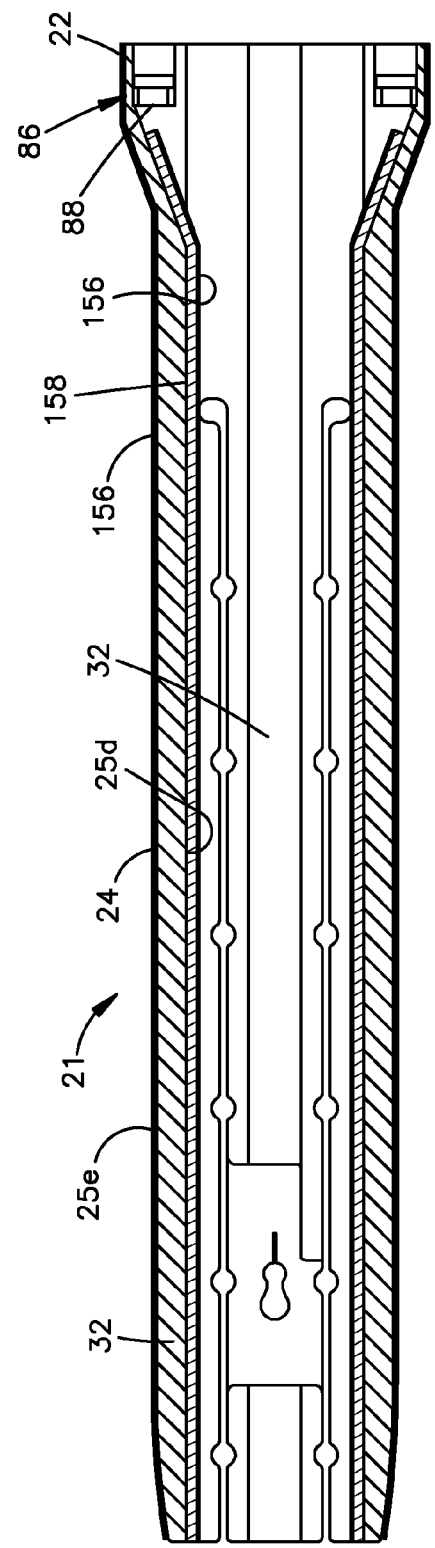

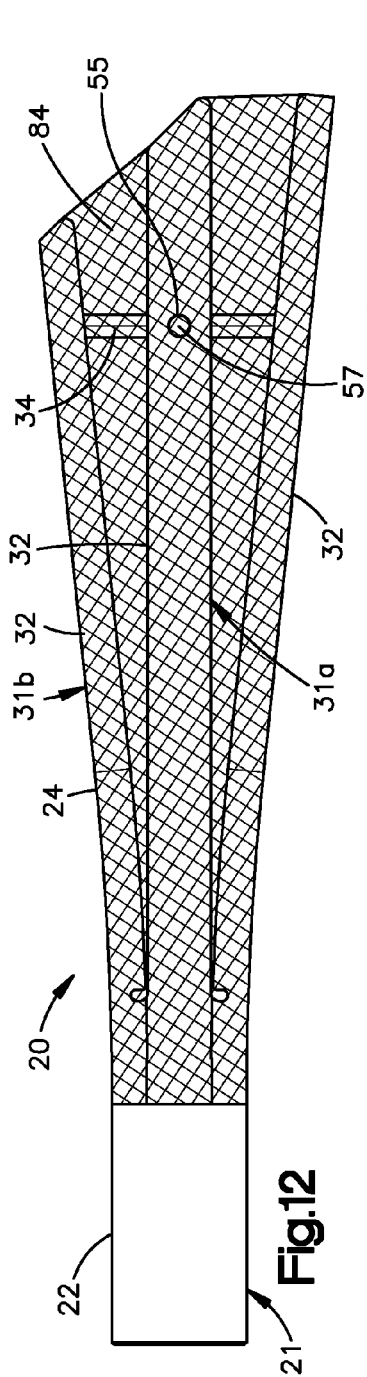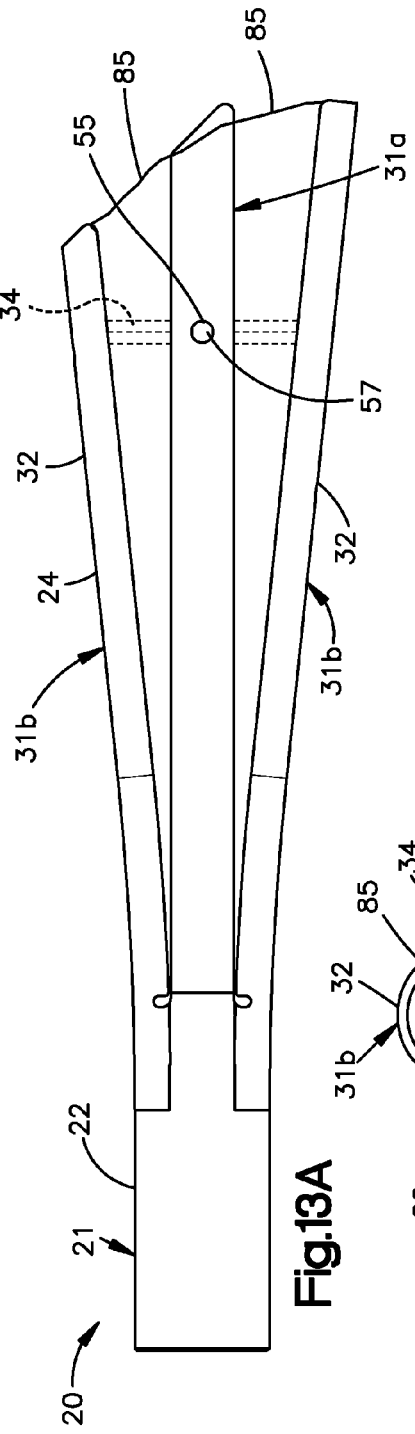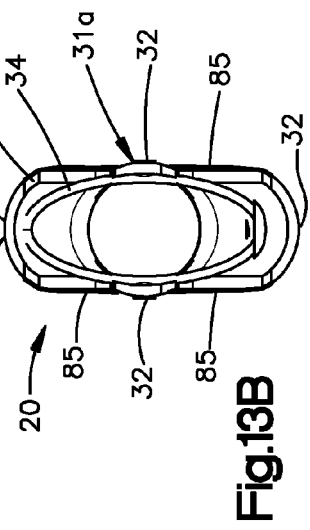

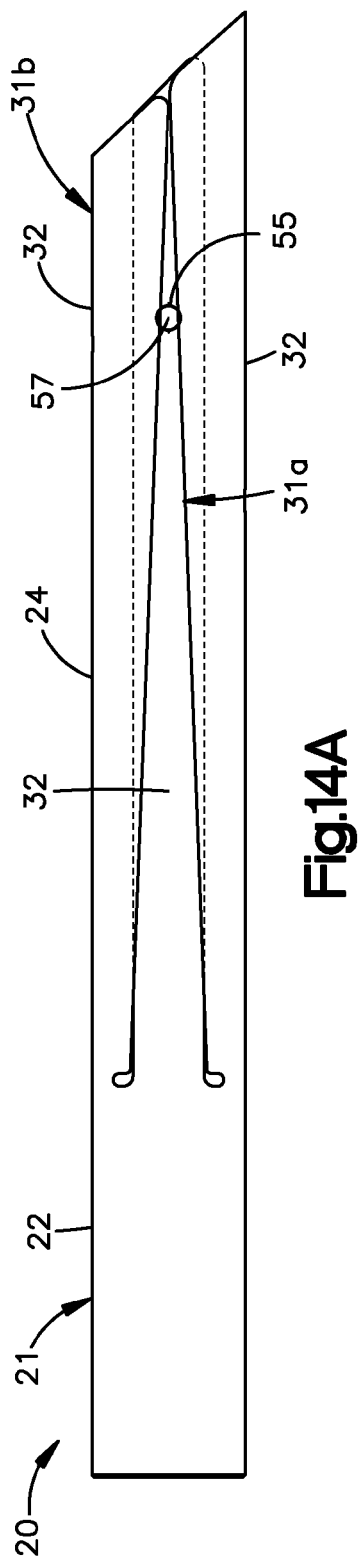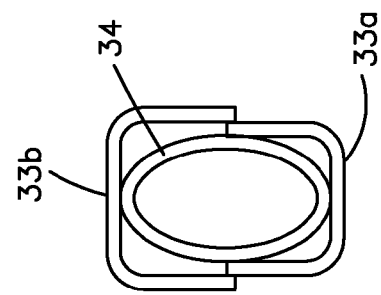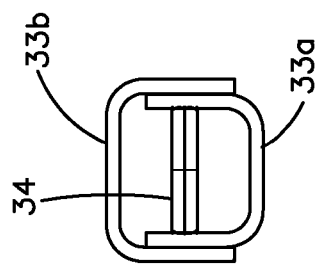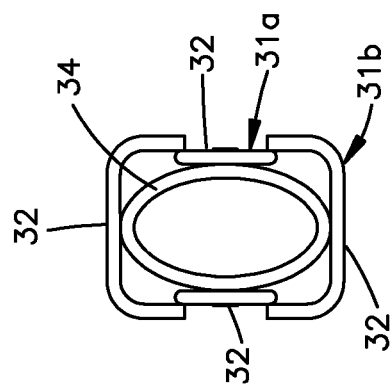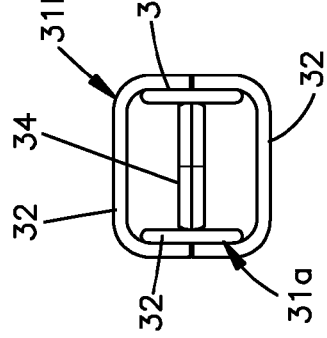

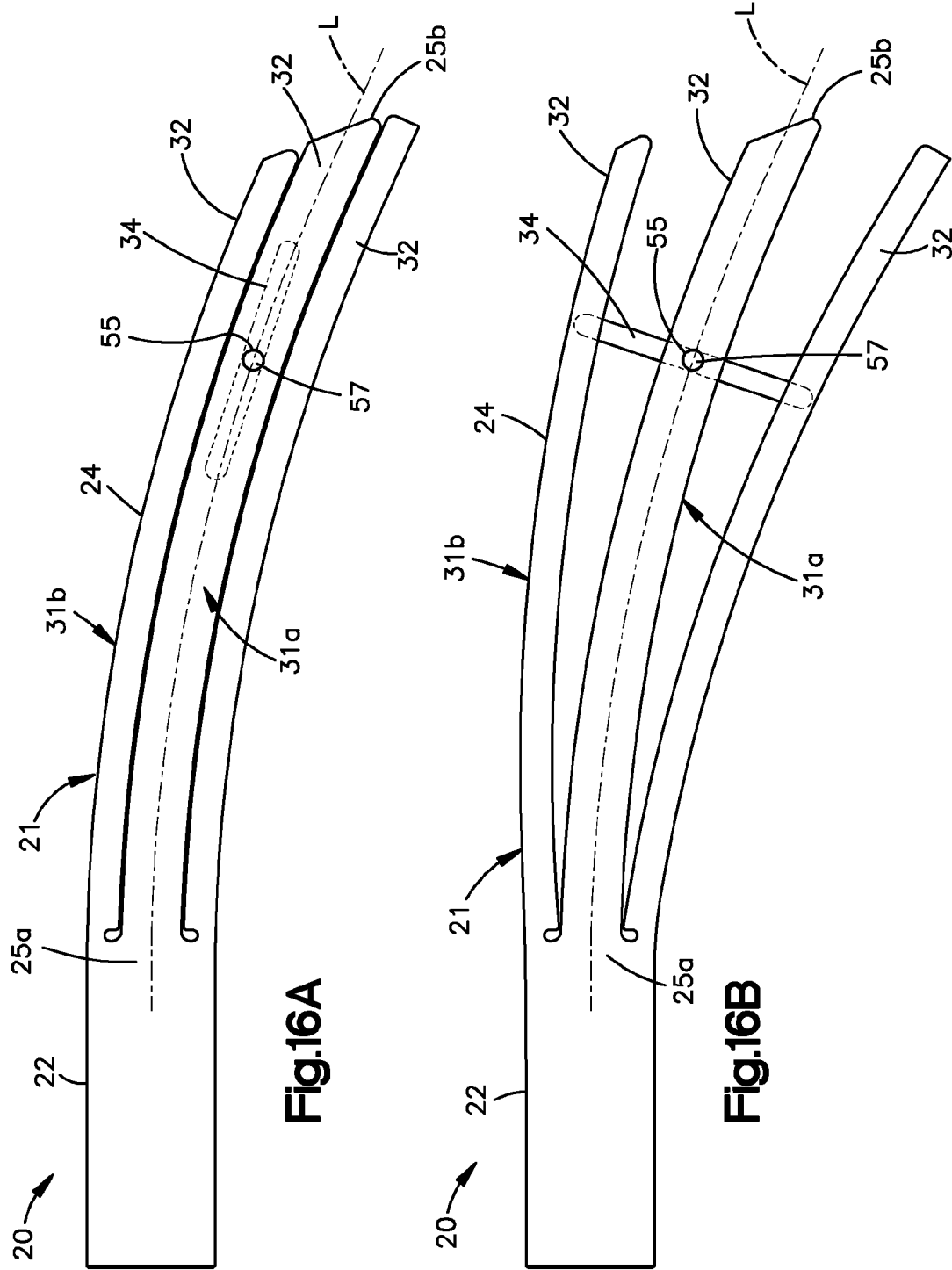

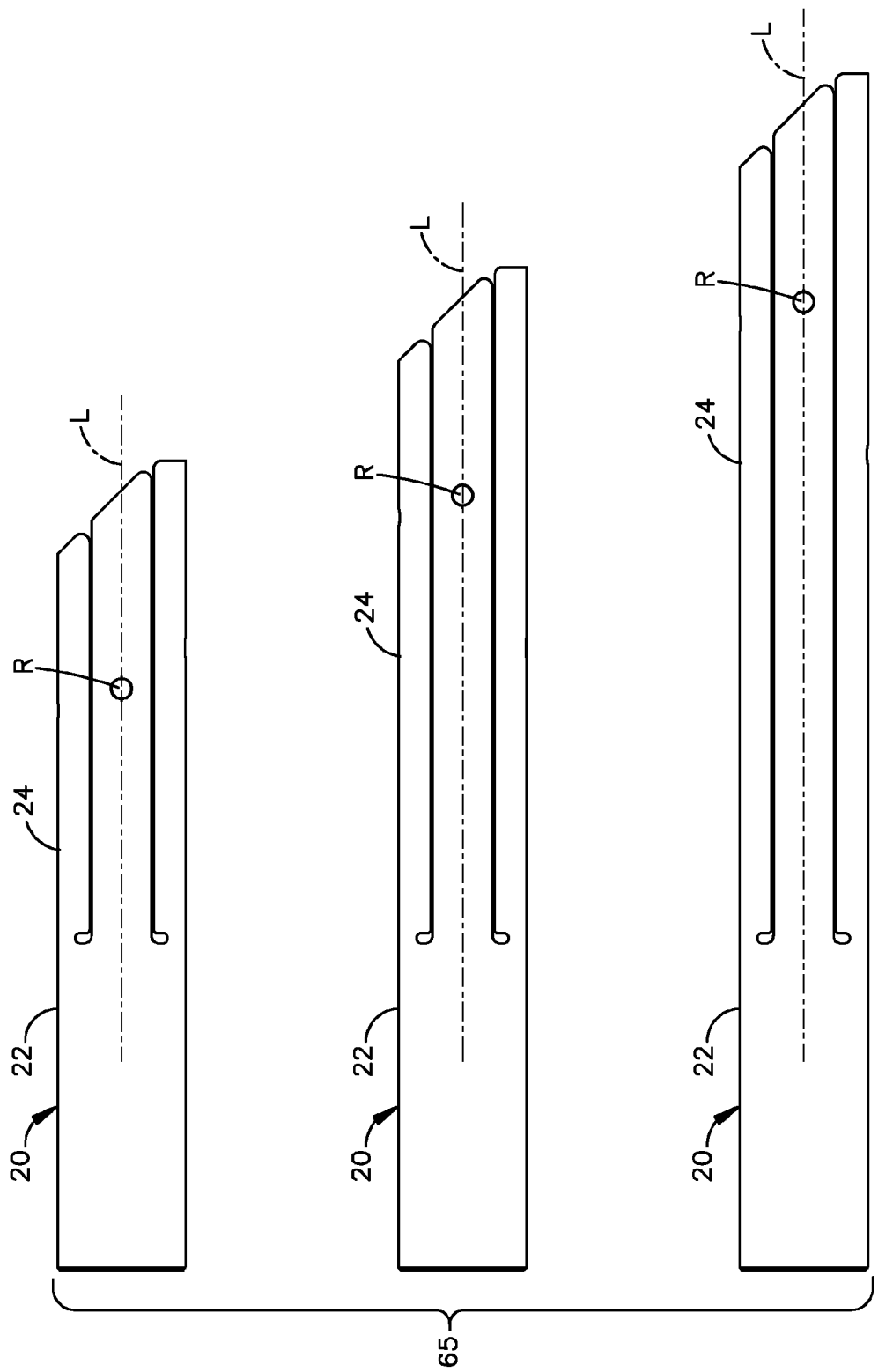

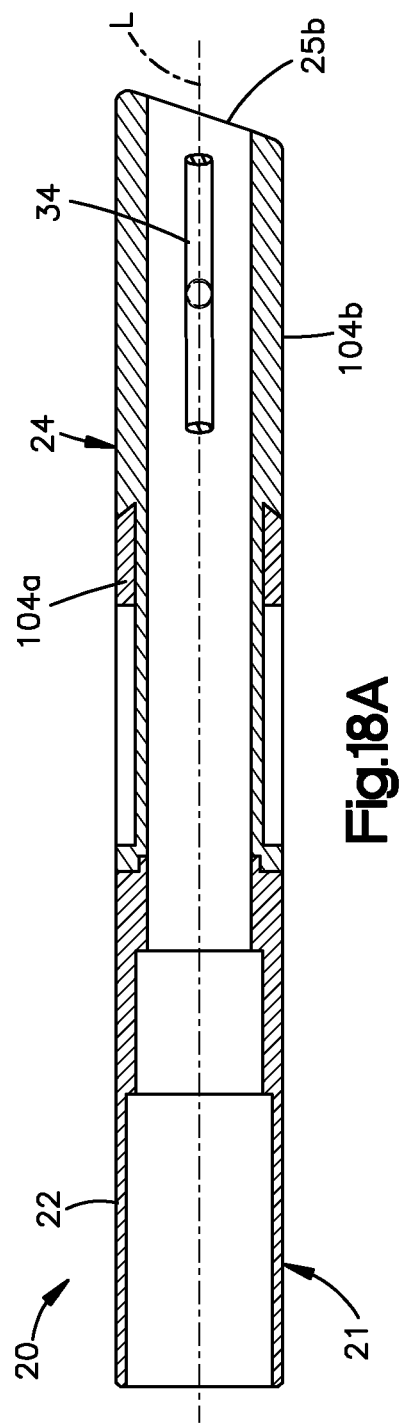
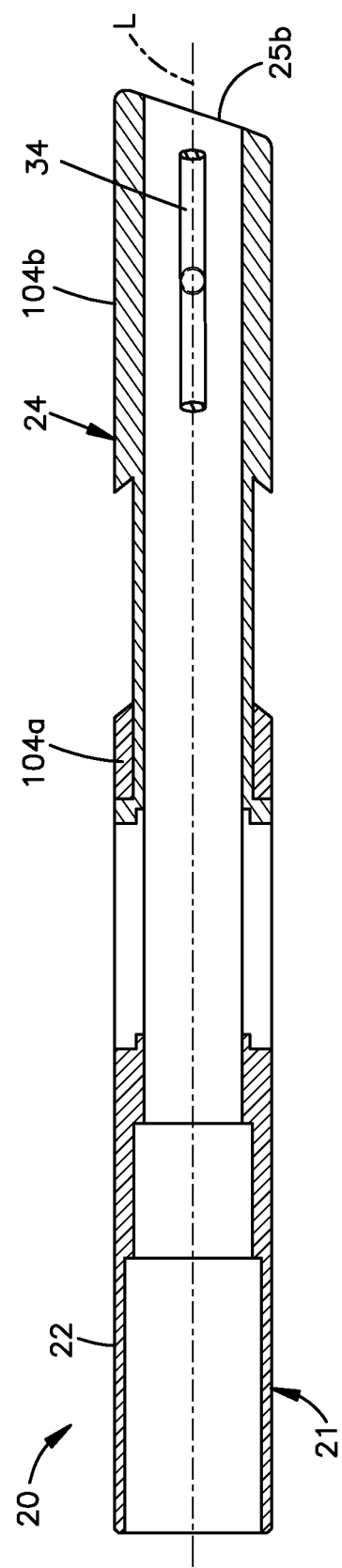

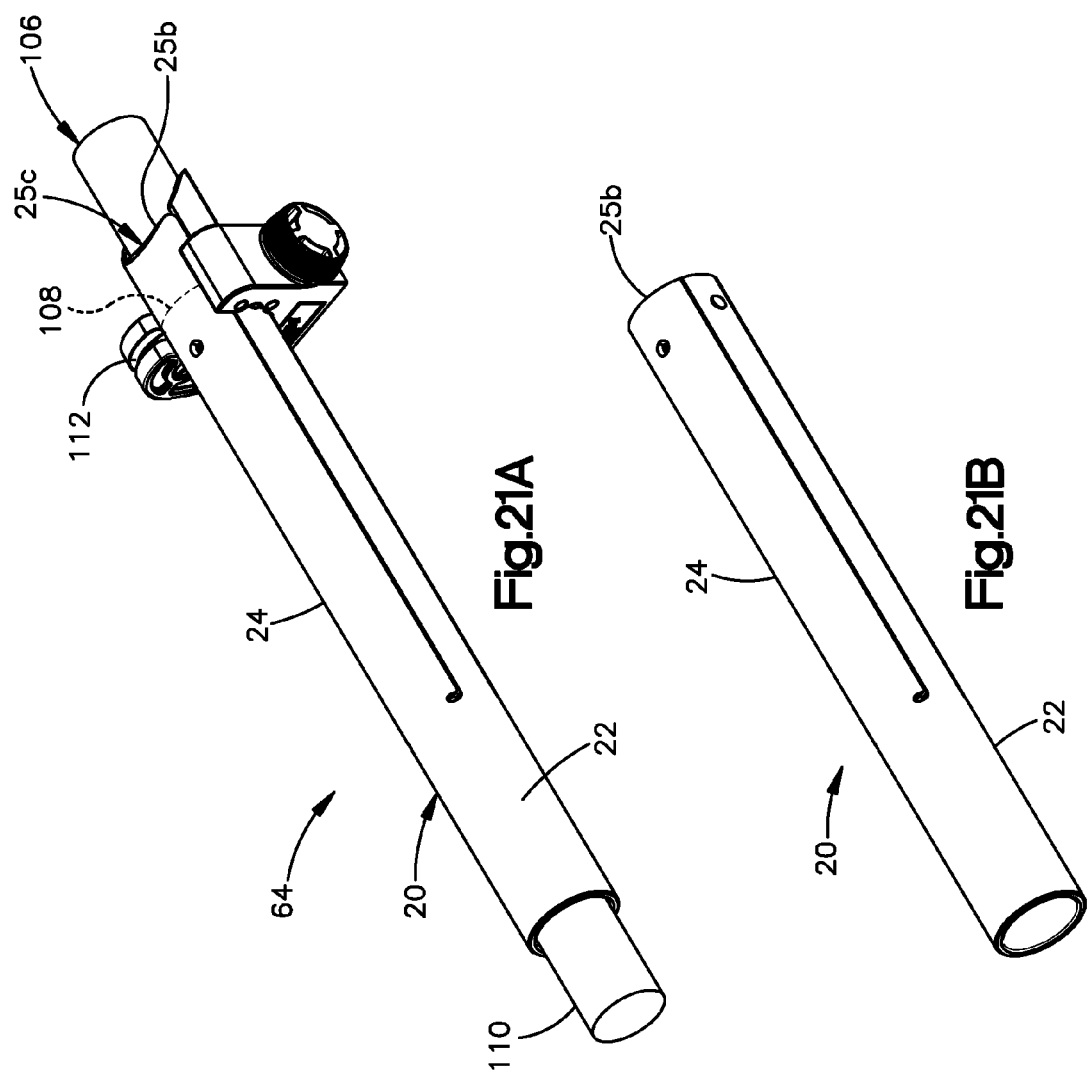

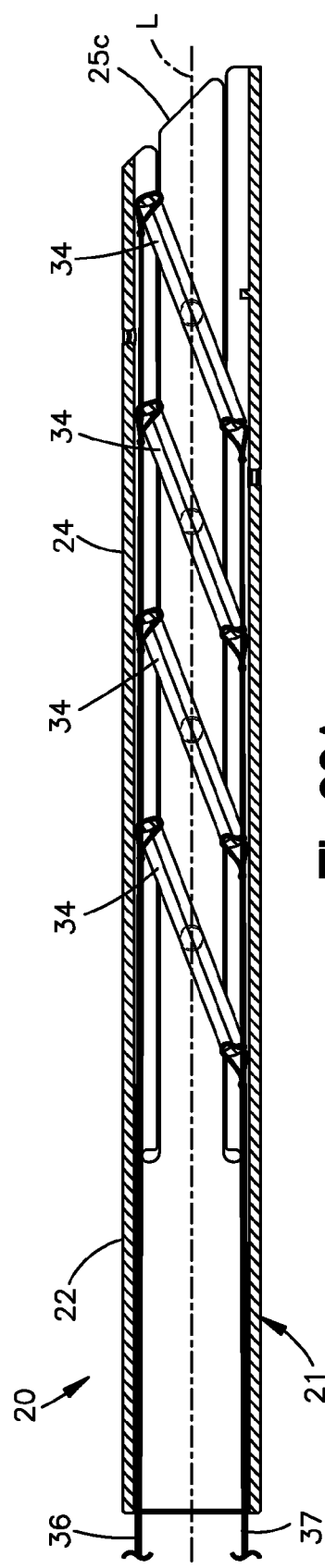
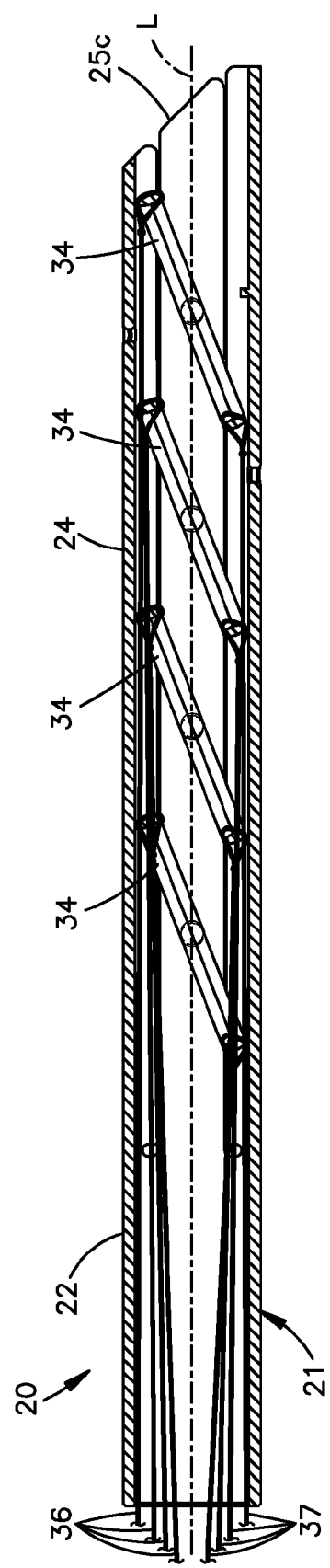
Fig.22A
Fig.22B

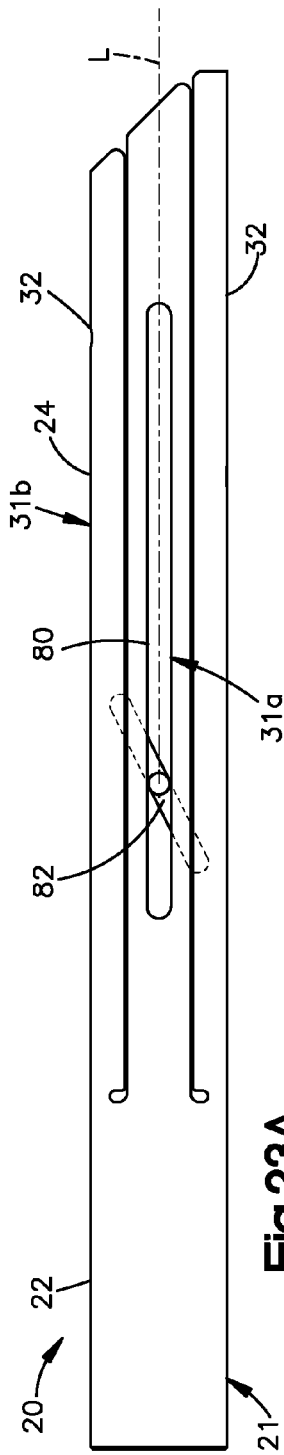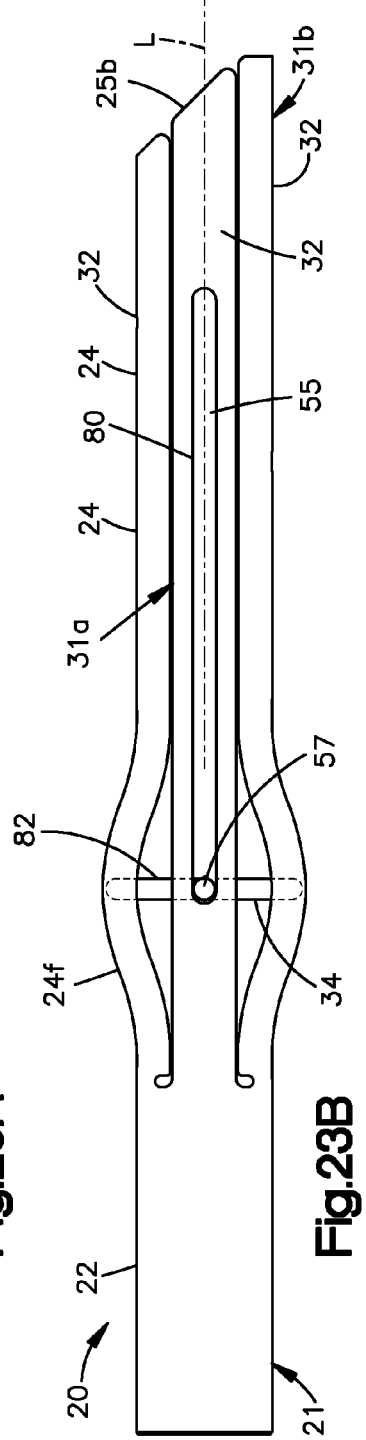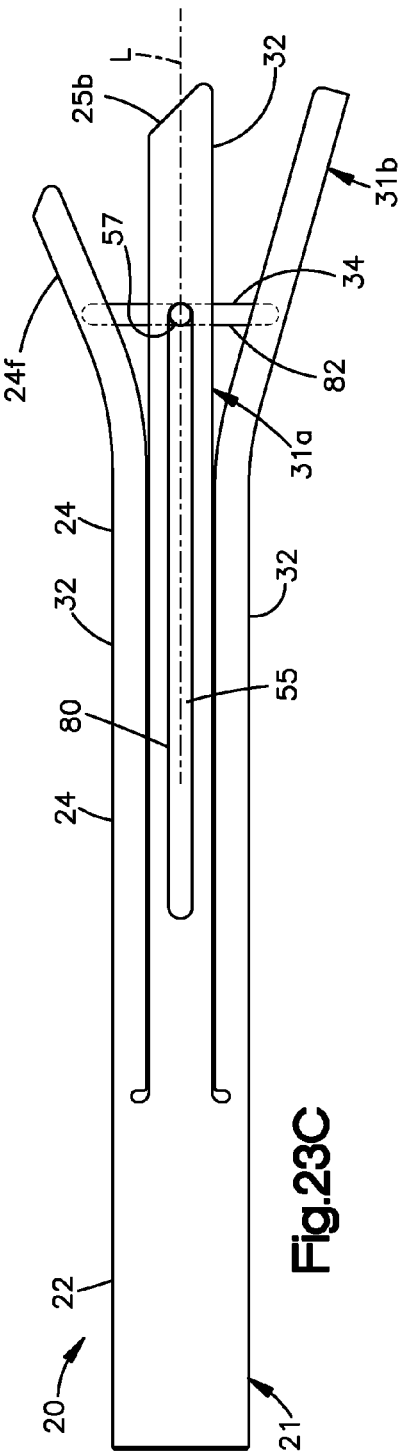

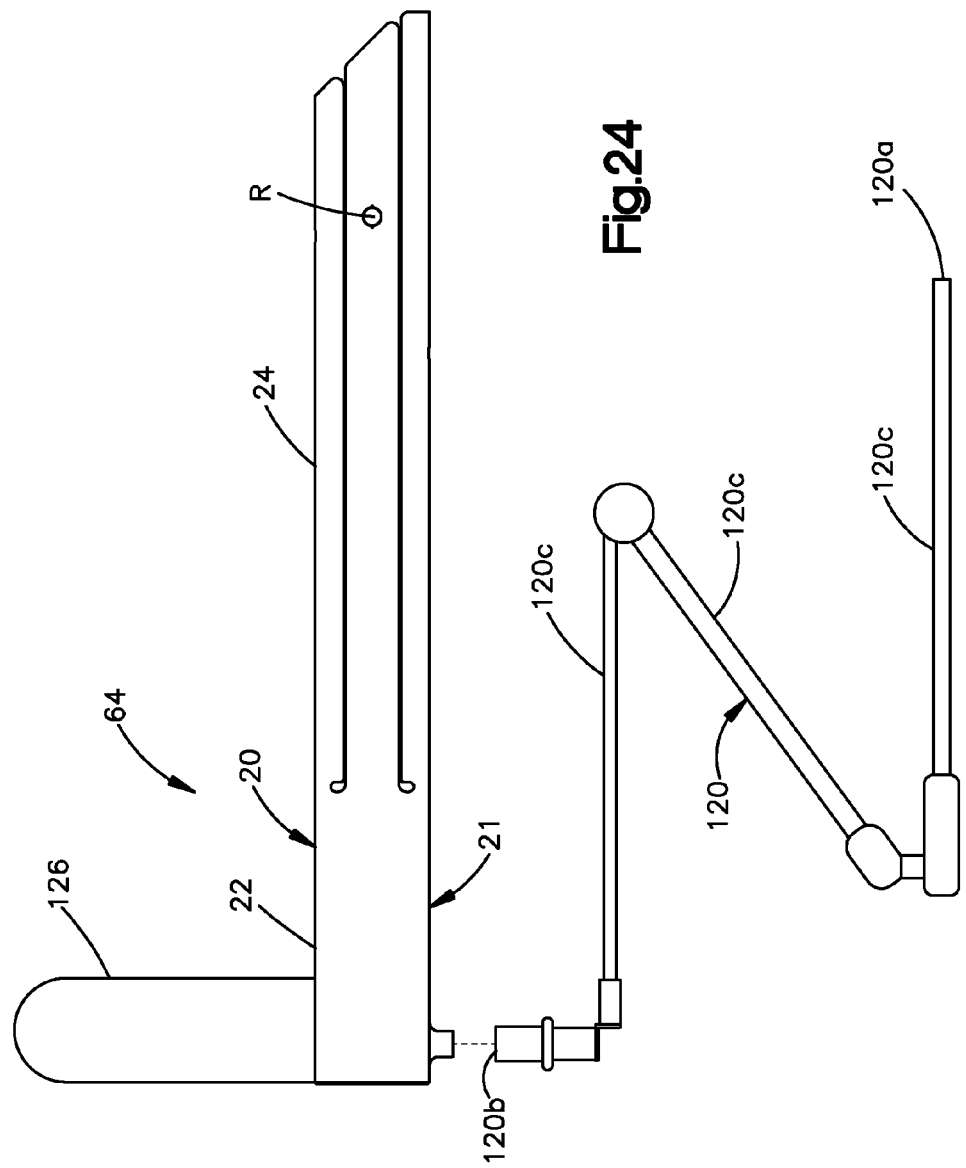

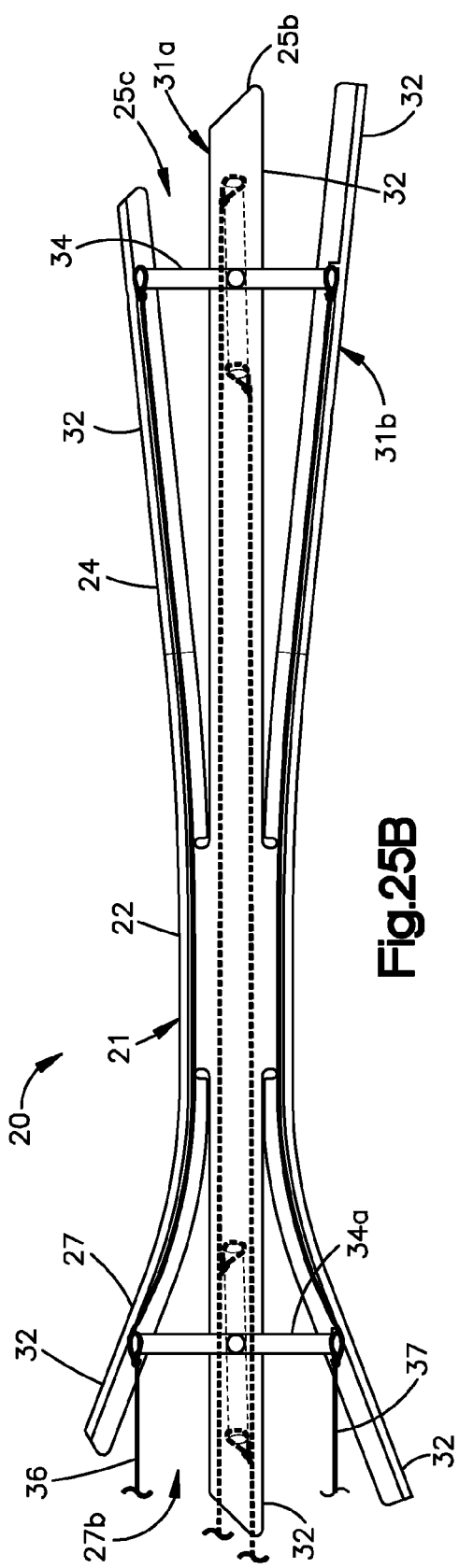
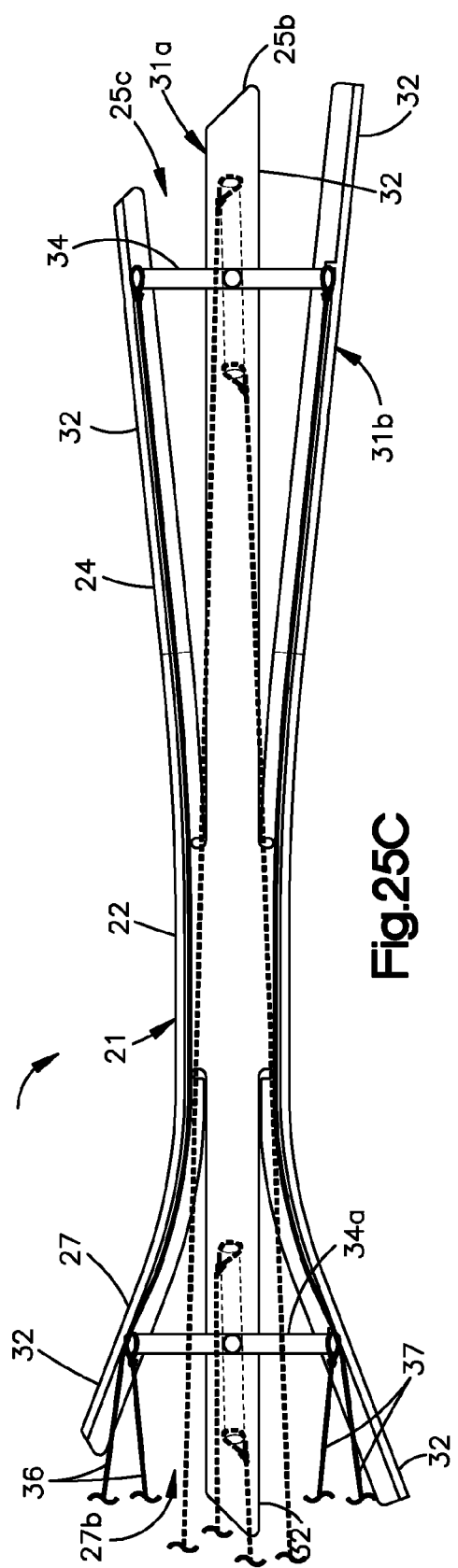

EXPANDABLE DILATOR

CROSS REFERENCE TO RELATED APPLICATIONS

This claims the benefit of U.S. Patent Application Ser. No. 61/812,877 filed Apr. 17, 2013, U.S. Patent Application Ser. No. 61/838,640 filed Jun. 24, 2013, and U.S. Patent Application Ser. No. 61/838,630 filed Jun. 24, 2013, the disclosure of each of which is hereby incorporated by reference in its entirety.

BACKGROUND

Conventional dilators are typically employed to gain surgical access to a target surgical site. For instance, an incision is made in the patient's skin, and the dilator is inserted through the incision and the soft tissue so that the distal end of the dilator is positioned adjacent the target surgical site. The dilator thus defines a channel through the soft tissue through which the surgical instruments can be driven to the target surgical site. Conventional dilators can include blades that at least partially define the channel. The blades can be actuated from a first position to a dilated position so as to expand the distal end and widen the channel at the distal end, thereby increasing the surgeon's working area at the target surgical site.

SUMMARY

In accordance with one embodiment, an expandable dilator is configured to dilate soft tissue. The expandable dilator can include a base that defines an outer surface and an inner surface opposite the outer surface, the inner surface at least partially defining a first conduit. The expandable dilator can further include a dilation member that extends from the base. The dilation member can define an inner surface and an outer surface opposite the inner surface, wherein the inner surface of the dilation member at least partially defines a second conduit in fluid communication with the first conduit. The second conduit is elongate along a longitudinal axis. The expandable dilator can further include an expansion member that is coupled to the dilation member and is movable with respect to the dilation member from a first position to an expanded position so as to cause at least a portion of the dilation member to expand from a first configuration to an expanded configuration along a direction of expansion that is angularly offset with respect to the longitudinal axis.

BRIEF DESCRIPTION OF THE DRAWINGS

The foregoing summary, as well as the following detailed description of example embodiments of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIG. 1A is a perspective view of an expandable dilator constructed in accordance with one embodiment, shown inserted into soft tissue, showing expandable dilator blades in a first position;

FIG. 1B is a perspective view of an expandable dilator illustrated in FIG. 1A, but showing the expandable dilator blades in a dilated position;

FIG. 2A is a perspective view of an expansion member of the expandable dilator illustrated in FIGS. 1A-B, the expansion member constructed in accordance with one embodiment;

FIG. 2B is a perspective view of an expansion member of the expandable dilator illustrated in FIGS. 1A-B, the expansion member constructed in accordance with another embodiment;

FIG. 2C is a perspective view of an expansion member of the expandable dilator illustrated in FIGS. 1A-B, the expansion member constructed in accordance with another embodiment;

FIG. 3A is a sectional side elevation view of the expandable dilator illustrated in FIG. 1A;

FIG. 3B is a sectional top plan view of the expandable dilator illustrated in FIG. 3A, taken at line 3B-3B;

FIG. 3C is a sectional side elevation view of the expandable dilator illustrated in FIG. 3A, shown in the dilated position;

FIG. 3D is a perspective view of the expandable dilator constructed in accordance with an alternative embodiment;

FIG. 4A is an enlarged sectional side elevation view of a portion of the expandable dilator illustrated in FIG. 3C, taken at region 4A;

FIG. 4B is an enlarged sectional side elevation view of the portion of the expandable dilator illustrated in FIG. 4B, but constructed in accordance with an alternative embodiment;

FIG. 5A is a sectional side elevation view of an expandable dilator, wherein the expansion member includes a pair of first and second expansion member segments, each shown in a respective first position;

FIG. 5B is a sectional side elevation view of the expandable dilator illustrated in FIG. 5A, showing the first and second expansion member segments in respective expanded position;

FIG. 5C is a sectional side elevation view of an expandable dilator as illustrated in FIG. 5A, but constructed in accordance with an alternative embodiment;

FIG. 6A is a sectional side elevation view of the expandable dilator as illustrated in FIG. 1B, showing a retention member constructed in accordance with one embodiment, configured to retain the dilator blades in the dilated position;

FIG. 6B is a sectional side elevation view of the expandable dilator as illustrated in FIG. 1B, showing a retention member constructed in accordance with another embodiment, FIG. 6C is a sectional side elevation view of the expandable dilator as illustrated in FIG. 1B, showing a retention member constructed in accordance with another embodiment, FIG. 6D is a sectional end elevation view of a portion the expandable dilator as illustrated in FIG. 6C, taken along line 6D-6D;

FIG. 7D is a sectional side elevation view of the expandable dilator illustrated in FIG. 1A, including an actuation leverage member constructed in accordance with another embodiment;

FIG. 7E is a sectional side elevation view of the expandable dilator illustrated in FIG. 1A, showing an actuation leverage member constructed in accordance with an alternative embodiment;

FIG. 7F is a sectional side elevation view of the expandable dilator illustrated in FIG. 1B, including the actuation leverage member illustrated in FIG. 7E;

FIG. 8A is a perspective view of an expandable dilator similar to the expandable dilator illustrated in FIG. 1A, but including an actuation leverage member constructed in accordance with another embodiment, showing the expandable dilator blades in a first position;

FIG. 8D is an exploded perspective view of a portion of the expandable dilator illustrated in FIG. 8A, showing the actuation leverage member;

FIG. 8E is a partial perspective view of the portion of the expandable dilator illustrated in FIG. 8D, showing the actuation leverage member movable between a locked position and an unlocked position;

FIG. 8G is a schematic perspective view of the actuation member attached to first and second actuation members and shown in a first position that causes the expandable dilator to be in the first position illustrated in FIG. 8A;

FIG. 8H is a schematic perspective view of the actuation member illustrated in FIG. 8G, but shown in a second position that causes the expandable dilator to be in the second position illustrated in FIG. 8B;

FIG. 8I is a schematic perspective view of the actuation member attached to a single actuation member and shown in a first position that causes the expandable dilator to be in the first position illustrated in FIG. 8A;

FIG. 8J is a schematic perspective view of the actuation member illustrated in FIG. 8I, but shown in a second position that causes the expandable dilator to be in the first position illustrated in FIG. 8A;

FIG. 9A is a sectional side elevation view of the expandable dilator illustrated in FIG. 1A, but including an auxiliary expansion member constructed in accordance with an one embodiment, shown in a first configuration;

FIG. 9B is sectional side elevation view of the expandable dilator as illustrated in FIG. 9A, shown in an expanded configuration;

FIG. 9C is a sectional side elevation view of the expandable dilator as illustrated in FIG. 9B, showing the expansion member in an expanded configuration retaining the dilator blades in the dilated position;

FIG. 10A is a sectional side elevation view of the expandable dilator as illustrated in FIG. 1B, including an illumination assembly constructed in accordance with one embodiment;

FIGS. 10B-10E are perspective views of a portion of the dilator blades illustrated in FIG. 10A, including a light shaping member constructed in accordance with different embodiments;

FIG. 11D is a sectional perspective view of the expandable dilator illustrated in FIG. 11C;

FIG. 11E is a sectional side elevation view of a dilation member of the expandable dilator illustrated in FIG. 11D, constructed in accordance with one embodiment;

FIG. 11F is a sectional side elevation view of the dilation member of the expandable dilator as illustrated in FIG. 11E, but constructed in accordance with another embodiment;

FIG. 11G is a sectional side elevation view of the dilation member of the expandable dilator as illustrated in FIG. 11F, but constructed in accordance with another embodiment;

FIG. 11K is a sectional side elevation view of the dilation member of the expandable dilator as illustrated in FIG. 11J, but constructed in accordance with another embodiment;

FIG. 11L is a sectional side elevation view of the dilation member of the expandable dilator as illustrated in FIG. 11K, but constructed in accordance with another embodiment;

FIG. 11O is a perspective view of the expandable dilator illustrated in FIGS. 11A-B, but shown constructed in accordance with another embodiment;

FIG. 12 is a side elevation view of the expandable dilator as illustrated in FIG. 1B, including an expandable material that surrounds at least a portion of the dilator blades;

FIG. 13A is a side elevation view of the expandable dilator as illustrated in FIG. 1B, including a cover that is connected between adjacent dilator blades;

FIG. 13B is an end elevation view of the expandable dilator as illustrated in FIG. 13A;

FIG. 14A is a side elevation view of the expandable dilator as illustrated in FIG. 1A, showing the dilator blades overlapping in accordance with one embodiment;

FIG. 14B is an end elevation view of the expandable dilator as illustrated in FIG. 14A;

FIG. 14C is an end elevation view of the expandable dilator as illustrated in FIG. 14B, showing the dilator blades in the dilated position;

FIG. 15A is an end elevation view similar to FIG. 14B, but showing the expandable dilator constructed in accordance with an alternative embodiment;

FIG. 15B is an end elevation view of the expandable dilator as illustrated in FIG. 15A, showing the dilator blades in the dilated position;

FIG. 16A is side elevation view of the expandable dilator as illustrated in FIG. 1A, but including curved dilator blades in accordance with an alternative embodiment FIG. 16B is side elevation view of the expandable dilator as illustrated in FIG. 16A, but showing the curved dilator blades in a dilated position;

FIG. 17 is a side elevation view of an expandable dilator kit including a plurality of expandable dilators as illustrated in FIG. 1A, but of different sizes;

FIG. 18A is a side elevation view of the expandable dilator as illustrated in FIG. 1A, but showing telescopic dilator blades constructed in accordance with one embodiment, the telescopic dilator blades shown in a retracted position;

FIG. 18B is a side elevation view of the expandable dilator as illustrated in FIG. 18A, but showing the telescopic dilator blades in an extended position;

FIG. 21A is a perspective view of an expandable dilator assembly including the expandable dilator illustrated in FIG. 1A and a cutter assembly configured to reduce a length of the expandable dilator;

FIG. 21B is a perspective view of the expandable dilator illustrated in FIG. 20A, having the reduced length;

FIG. 22A is a sectional side elevation view of the expandable dilator as illustrated in FIG. 1A, but including a plurality of expansion members in accordance with an alternative embodiment;

FIG. 22B is a sectional side elevation view of the expandable dilator as illustrated in FIG. 22A, but constructed in accordance with another embodiment;

FIG. 23A is a sectional side elevation view of the expandable dilator as illustrated in FIG. 1A, but showing the dilator blades made from a flexible material;

FIG. 23B is a sectional side elevation view of the expandable dilator as illustrated in FIG. 23A, but showing an expansion member locally expanding a portion of the dilator blades;

FIG. 23C is a sectional side elevation view of the expandable dilator as illustrated in FIG. 23B, but showing an expansion member translated to the distal end of the dilator blades so as to locally expand the distal end of the dilator blades;

FIG. 24 is a schematic side elevation view of an expandable dilator assembly including the expandable dilator illustrated in FIG. 1A and an articulating support assembly configured to support the expandable dilator;

FIG. 25B is a sectional side elevation view of the expandable dilator as illustrated in FIG. 25A; and FIG. 25C is a sectional side elevation view of the expandable dilator as illustrated in FIG. 25A, but constructed in accordance with another embodiment.

DETAILED DESCRIPTION

Figure 7A:
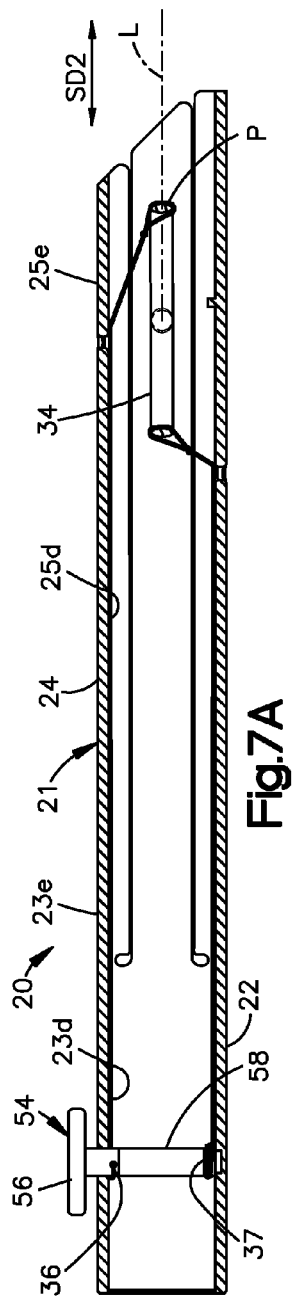
FIG. 7A is a sectional side elevation view of the expandable dilator illustrated in FIG. 1A, including an actuation leverage member constructed in accordance with one embodiment.

Referring initially to FIGS. 1A-3D, an expandable dilator 20 includes a dilator body 21 that can be made of any suitable biocompatible material. The dilator body 21 can include a base 22 and a dilation member 24 that extends from the base 22 along a distal direction to a free end 24*a* of the dilation member 24. As will be described in more detail below, the dilation member 24 can extend along a substantially straight path from the base 22 along the distal direction, or can extend along a curved or any suitable alternatively shaped path along the distal direction. Further as will be described in more detail below, the dilation member 24 can include at least a pair of dilator blades 32, for instance a first pair 31*a* of opposed dilator blades 32, and a second pair 31*b* of opposed dilator blades 32. It should thus be appreciated that reference herein to the dilation member 24 can refer equally to one or more up to all of the dilator blades 32, unless otherwise indicated. For instance, reference herein to expansion of the dilation member 24 can equally apply to expansion of one or more of the dilator blades 32, unless otherwise indicated. The dilation member 24 is configured to be inserted through an incision formed in the anatomical dermal layer 26, and into soft tissue 28 that is disposed behind the dermal layer along the direction of insertion, until the free end 24*a* of the dilation member 24 is positioned adjacent a target surgical site 29 at which a surgical procedure is to be performed.

The dilator body 21 defines a proximal end 21*a* and a distal end 21*b* that is spaced from the proximal end 21 along a distal direction, which can be straight, curved, or otherwise shaped as desired. Similarly, the proximal end 21*a* is spaced from the distal end 21*b* along a proximal direction, which can be straight, curved, or otherwise shaped as desired. The base 22 includes a base body 23 that defines a proximal end 23a and a distal end 23b, and a first conduit 23c that extends through the base body 23 from the proximal end 23a to the distal end 23b. The base body 23, and thus the base 22, defines an inner surface 23d that at least partially or entirely defines the first conduit 23c, and an outer surface 23e opposite the inner surface 23d. The dilation member 24 defines a dilation body 25 that defines a proximal end 25a and a distal end 25b, and a second conduit 25c that extends through the dilation body 25 from the proximal end 25a to the distal end 25b. The dilation body 25, and thus the dilation member 24, defines an inner surface 25d that at least partially or entirely defines the second conduit 25c, and an outer surface 25e opposite the inner surface 25d. The proximal end 21a of the dilator body 21 can be defined by the proximal end 23a of the base 22, and the distal end 21b of the dilator body 21 can be defined by the distal end 25b of the dilation body 25, which can define the free end 24a of the dilation member 24. It should be appreciated that reference to the inner surface 25d and the outer surface 25e can apply to any one or more up to all of respective inner and outer surfaces of one or more up to all of the dilator blades 32.

The proximal end 25a of the dilation member 24 extends along the distal direction with respect to the distal end 23b of the base 22, for instance from the distal end 23b. The dilation member 24 can be monolithic with the base 22, or can be attachable, for instance removably attachable, to the base 22. The first conduit 23c is in fluid communication with the second conduit 25c, such that surgical instrumentation can be inserted into the proximal end 23a of the base 22, through the first conduit 23c and the second conduit 25c and out the distal end 25b of the dilation member to perform a surgical procedure at the target surgical site 29.

The target surgical site 29 can be defined by any anatomy of a human or other animal, such as a quadruped. In accordance with the illustrated embodiment, the target surgical location is an intervertebral space 30 that is disposed between, and can be defined between a first or superior vertebral body 30a and a second or inferior vertebral body 30b that is inferior with respect to the first vertebral body 30a. The vertebrae 30a-b can be defined by any vertebral region, such as the lumbar or thoracic region. The dilation member 24 can be inserted along a lateral transpsoas approach to the intervertebral space 30, using neuro-monitoring. The soft tissue 28 can be sequentially dilated as desired prior to inserting the dilation member 24 through the soft tissue 28 to the target surgical site 29.

The dilation member 24 can be inserted in a first configuration, which can be an initial configuration, into the soft tissue 28 to a depth whereby the free end 24a is disposed adjacent the surgical site 29. At least a portion of the dilation member 24, for instance the free end 24a, can be subsequently expanded to an expanded configuration along a direction of expansion. For instance, the second conduit 25c can be elongate along a longitudinal axis L, which can be centrally disposed with respect to the inner surface 25d of the dilation member 24. The direction of expansion can be angularly offset, such as perpendicular, with respect to the longitudinal axis L. For instance, the dilation member 24 can be oriented such that the direction of expansion is in the anterior-posterior direction, the cranial-caudal direction, or in a direction that includes both the anterior-posterior direction and the cranial-caudal direction. Thus, the direction of expansion can be in a plane that is defined by the anterior-posterior direction and the cranial caudal direction.

Thus, the cross-sectional dimension of the second conduit 25c at the distal end 25b along a select direction SD1 between opposed inner surfaces 25d, which can be the direction of expansion, is greater than the cross-sectional dimension of the second conduit 25c at the proximal end 25a along the select direction SD1. For instance, the cross-sectional dimension of the second conduit 25c at the proximal end 25a along the select direction SD1 can be the substantially equal to the cross-sectional dimension of the second conduit 25c at the distal end 25b when the dilation member is in the first configuration. When the distal end 25b of the dilation member 24 is positioned adjacent the surgical site 29, the base 22 or the proximal end 25a of the dilation member 24 can traverse the dermal layer 26. Accordingly, because the incision can be made only large enough to receive the base 22 and the dilation member 24 when in the first configuration, the surgical procedure can be minimally invasive.

In accordance with the illustrated embodiment, the expandable dilator 20 includes an expansion member 34 that is coupled to the dilation member 24 and movable with respect to the dilation member 24 from a first position (see FIGS. 3A-B) to an expanded position (see FIG. 3C) so as to cause at least a portion, for instance the free end 24a, of the dilation member 24 to expand from the first configuration to the expanded configuration along the direction of expansion. For instance, the expansion member 34 can be coupled to the dilation member 24 at or adjacent the free end 24a, and thus spaced further from the proximal end 25a than the distal end 25b. In accordance with one embodiment, the expansion member 34 is rotatably coupled to the dilation member 24 so as to rotate relative to the dilation member 24 about an axis of rotation R from the first position to the expanded position. The axis of rotation R can define a central axis of the expansion member 34 that bisects the expansion member 34 into two equal halves. Alternatively, the axis of rotation R can be offset with respect to the central axis of the expansion member 34. The direction of expansion can be angularly offset, such as substantially perpendicular, with respect to the axis of rotation R. The axis of rotation R can be oriented angularly offset, for instance substantially perpendicular, with respect to the longitudinal axis L of the second conduit 25c. For instance, the axis of rotation R can intersect the longitudinal axis L of the second conduit 25c. The dilation member 24 can be oriented such that the axis of rotation R is cranial-caudal direction, the anterior-posterior direction, or in a direction that includes both the anterior-posterior direction and the cranial-caudal direction. Thus, the axis of rotation R can be disposed in a plane that is defined by the anterior-posterior direction and the cranial caudal direction.

The expansion member 34 can define an outer perimeter P having a first outer dimension D1 along the axis of rotation R, and a second outer dimension D2 along a select direction SD2 that is angularly offset, for instance perpendicular, with respect to the axis of rotation R. The second outer dimension D2 is greater than the first outer dimension D1, such that rotation of the expansion member 34 from the first position to the expanded position causes the expansion member 34 to bias the dilation member 24 from the first configuration at least toward, for instance to, the expanded configuration. It should also be appreciated that the expansion member 34 defines a first distance that extends from the axis of rotation R along a direction perpendicular to the axis of rotation to an outer perimeter P of the expansion member 34, the first distance being greater than the second distance from the axis of rotation R to at least a portion of the dilation member 24 along a direction perpendicular to the axis of rotation when the dilation member is in the first configuration. Accordingly, the outer perimeter P of the expansion member 34 can abut at least a portion of the inner surface 25d of the dilation member 24 and apply a biasing force to the dilation member that biases the dilation member 24 toward, for instance to, the expanded configuration, as the expansion member 34 is moved to the expanded position. The expansion member 34 can be rotated in a first rotational direction about the axis of rotation R from the first position to the expanded position. The expansion member 34 can be rotated in a second rotational direction opposite the first direction about the axis of rotation R from the expanded position to the first position, which can withdraw the biasing force that is applied from the outer perimeter P to the inner surface 25d of the dilation member 24.

The expansion member 34 can define the shape of an oval or any suitable alternative shape as desired, and can be an annular ring so as to define a channel is disposed in the second conduit 25c. The surgical instrumentation can thus be inserted through the proximal end 25a of the second conduit 25c, through the channel of the expansion member 34, and out the distal end 25b of the second conduit 25c. When the expansion member 34 is in the first position, the select direction SD2 can be substantially parallel to the longitudinal axis L (see FIG. 7A), or angularly offset with respect to the longitudinal axis L (see FIG. 3A). When the expansion member 34 is in the expanded position, the select direction can be oriented substantially perpendicular to the longitudinal axis L and substantially parallel to the select direction SD2 of the dilation member 24.

As described above, the dilation member 24 can include at least a pair of dilator blades 32 that are supported by the base 22, and can extend between the proximal end 25a and the distal end 25b, for instance from the proximal end 25a to the distal end 25b. One of the pair of dilator blades 32 can be configured to be biased by the expansion member 34 to move away from the other of the dilator blades 32, from a first position to a dilated position. At least one or more up to all of the dilator blades 32 can be monolithic with the base 22 or attachable, for instance removably attachable, to the base 22.

At least a portion of the dilator blade 32, for instance at the distal end 25b, is spaced further from the longitudinal axis L when in the dilated position than when in the first position. As the at least one of the dilator blades 32 moves from the first position to the dilated position, the dilation member 24 can be said to move from the first configuration to the expanded configuration. In accordance with one embodiment, the dilation member 24 can include a first pair 31a of opposed dilator blades 32, and a second pair 31b of dilator blades 32, though the dilation member 24 can include any number of blades 32 as desired that at least partially define the second conduit 25c. The dilator blades 32 of the first pair 31a can be opposite each other along the cranial-caudal direction. The dilator blades 32 of the second pair 31b are configured to be spaced from each other along the anterior-posterior direction, though it should be appreciated that the first and second pairs 31a and 31b of dilator blades 32 can be spaced along any direction as desired that can lie in a plane defined by the anterior-posterior direction and the cranial-caudal direction. At least one or more up to all of the dilator blades 32 can define a curvature along a plane that extends normal to the longitudinal axis L, or can define any alternative shape as desired. The expansion member 34 is rotatably coupled to at least one or both of the dilator blades 32 of one of the first and second pairs 31a and 31b of dilator blades 32. One of the dilator blades 32 of the second pair 31b, for instance an anterior blade 32 of the second pair 31b, can extend further from the base along the distal direction than the other of the blades 32 of the second pair 31b, which can be a posterior blade 32 that is spaced from the anterior blade 32 in the posterior direction when the dilation member 24 is driven into the soft tissue 28.

Expansion of the expansion member 34 from the first position to the expanded position causes the expansion member 34 to bias one or both of the dilator blades 32 of the other of the first and second pairs 31a and 31b of the dilator blades 32, respectively referred to as an expandable dilator blade or blades, to expand from the first position to the dilated position. Expansion of a dilator blade from the first position to the dilated position can increase a distance between the expanded dilator blade with respect to the longitudinal axis L, for instance along the select direction SD1. Further, expansion of a dilator blade 32 of an opposed pair of dilator blades from the first position to the dilated position can increase a distance between the expanded dilator blade and the opposed dilator blade 32 of the pair of dilator blades, for instance along the select direction SD1.

In accordance with the illustrated embodiment, the expansion member 34 is rotatably coupled to one or both of the dilator blades 32 of the first pair 31a. For instance, the dilator blades 32 of the first pair 31a can each define a first attachment location 55, such as an aperture, and the expansion member 34 can define a complementary second attachment location 57, such as a projection that is sized to be inserted into the aperture. It should be appreciated that the first and second attachment locations 55 and 57 can be alternatively constructed as desired. Rotation of the expansion member 34 about the axis of rotation R with respect to the dilator blades 32 of the first pair 31a from the first position to the expanded position causes the expansion member 34 to bias one or both of the dilator blades 32 of the second pair 31b to expand from the first position to the dilated position away from the longitudinal axis L and the other dilator blade of the second pair 31b along the select direction SD1. Thus, the dilator blades 32 of the second pair 31b can be referred to as expandable blades that are movable from the first position to the dilated position. It should be appreciated, of course, that the expansion member 34 can be rotatably coupled to one or both of the dilator blades 32 of the second pair 31b, such that the expansion member 34 biases one or both of the dilator blades 32 of the first pair to expand from the first position to the dilated position as the expansion member 34 expands from the first position to the expanded position. While the attachment locations 55 can be supported by the dilator blades 32 of the first pair 31a of dilator blades, such that the dilator blades 32 of the second pair 31b define expandable dilator blades 32, the attachment locations can alternatively be supported by the dilator blades 32 of the second pair 31b of dilator blades, such that one or both of the dilator blades 32 of the first pair 31a of dilator blades define expandable dilator blades.

The dilator blades 32 can be configured substantially linearly along a linear direction from their respective proximal ends to their respective distal ends, such that the longitudinal axis L of the dilation member 24 can extend substantially linearly from the proximal end 25a to the distal end 25b. Alternatively, as illustrated in FIGS. 16A-16B, one or more of the dilator blades 32 can be curved along a direction between their respective proximal ends and their respective distal ends, for instance from their respective proximal ends to their respective distal ends, such that the longitudinal axis L is curved at least between the proximal end 25a and the free end 25b. The dilation member 24 can define any suitable alternative shape as desired. It is envisioned that curved surgical tools can be inserted through the second conduit 25c when the longitudinal axis L is curved, and a camera can be inserted through the second conduit 25c to the distal end 25b to allow for viewing of the target surgical site.

Referring also to FIG. 12, the expandable dilator 20 can be configured to prevent soft tissue from entering the second conduit 25c through gaps between the dilator blades 32 when the dilation member 24 is in the expanded configuration. For instance, the expandable dilator 20 can include an expandable sleeve 84 that is made from an expandable material, such as a mesh, that is configured to receive at least a portion of the dilation member 24, such that the sleeve 84 surrounds at least a portion of the dilator blades 32. Thus, the sleeve 84 can fully surround at the dilator blades 32 along at least a portion up to all of their respective lengths both when the dilator blades 32 are in the first position and when the dilator blades 32 are in the dilated position. Alternatively or additionally, as illustrated in FIGS. 13A-B, the expandable dilator 20 can include a plurality of covers 85, which can be made of any suitable biocompatible material that is connected between adjacent edges of adjacent ones of at least two or more up to all of the dilator blades 32 so as to extends across a gap that is defined between the adjacent dilator blades 32 along at least a portion of the length of the respective dilator blades 32.

Alternatively or additionally still, referring to FIGS. 14A-14C, one or both of the expandable dilator blades 32, which can be defined by the second pair 31b, can overlap the dilator blades 32 of the first pair 31a, both when in the first position and when in the dilated position, such that the dilator blades 32 fully enclose an entirety of the perimeter of at least a portion of the second conduit 25c, at least along a portion up to all of their respective lengths. For instance, one or both of the dilator blades 32 of the second pair 31b can include arms that extend to a location that overlaps respective ones of the dilator blades 32 of the first pair 31a along a direction that is parallel with respect to the axis of rotation R, both in the first position and in the expanded position.

Referring to FIGS. 15A-15B, the dilation member 24 constructed in accordance with an alternative embodiment can include a first dilator blade 33a and a second dilator blade 33b that is opposite the first dilator blade 33a along the select direction SD1. Each of the first and second dilator blades 33a and 33b can overlap each other along a direction that is parallel to the axis of rotation R. For instance, each of the first and second dilator blades 33a and 33b can define side walls that overlap, such that select side walls of one of the first and second dilator blades 33a and 33b are inner side walls that are disposed closer to the longitudinal axis L than the side walls of the other of the first and second dilator blades 33a and 33b. The dilator blade 33a having the inner side walls can be referred to as an inner dilator blade 33a, and the dilator blade 33b having the other side walls can be referred to as an outer dilator blade 33b.

The expansion member 34 can be coupled, for instance rotatably coupled, to one or both of the side walls of the inner dilator blade 33a. For example, the inner dilator blade 33a can define a first attachment location, such as an aperture, and the expansion member 34 can define a complementary attachment location, such as a projection that is sized to be inserted into the aperture. Rotation of the expansion member 34 about the axis of rotation R with respect to the inner dilator blade 33a from the first position to the expanded position, whereby the expansion member 34 biases the outer dilator blade 33b away from the longitudinal axis L along the select direction SD1 to the dilated position. Thus, the outer dilator blade 33b can be referred to as the expandable blade that is movable from the first position to the dilated position. Thus, the dilator blades 33a and 33b can overlap along the axis of rotation R, for instance at their respective opposed side walls, both when in the first position and when in the dilated position. Accordingly, the dilator blades 33a and 33b can fully define at least a portion of the outer perimeter of the second conduit 25c both when in the first position and when in the dilated position, thereby preventing soft tissue from entering the second conduit 25c when the dilation member 24 is in the expanded configuration.

Referring again to FIGS. 1-3D, the expandable dilator 20 can further include an actuator 36 that is coupled, directly or indirectly, to the expansion member 34. The actuator 36 can be attached to the expansion member 34 at a location offset from the axis of rotation R along the select direction SD2. As illustrated in FIG. 2A, the actuator 36 can be separate from the expansion member 34 and coupled, directly or indirectly, to the expansion member 34. For instance, the actuator 36 can be can be tied to or otherwise secured to the expansion member 34 at an attachment location of the expansion member 34, which can be a groove, channel, or other localized structure that prevents the actuator 36 from sliding along the perimeter P of the expansion member 34 to a location closer to the axis of rotation R along the select direction SD2. Alternatively, as illustrated in FIG. 2C, the actuator 36 can be attached to the expansion member 34 via an attachment member 38 that can extend between the expansion member 34 and the actuator 36. Alternatively still, as illustrated in FIG. 2B, the actuator 36 can be monolithic with the expansion member 34. The actuator 36 can be flexible as illustrated in FIGS. 2A and 2B, or can be substantially rigid as illustrated in FIG. 2C. The attachment member 38 can be flexible and can extend between the rigid actuator 36 illustrated in FIG. 2C and the expansion member 34.

The actuator 36 is configured to receive an actuation force, for instance in the proximal direction, that can be referred to as an expansion force, and in turn apply a biasing force, for instance in the proximal direction, to the expansion member 34 that causes the expansion member 34 to move from the first position to the expanded position. The actuator 36 extends along the proximal direction from the expansion member 34 toward the base 22. A pulling force can be applied to the actuator 36, which causes the actuator 36 to apply biasing force in the proximal direction to the expansion member. The actuator 36 can extend from the expansion member 34 through the second conduit 25c, and into the first conduit 23c. The actuator 36 can further extend through the proximal end 23a of the first conduit 23c. Thus, the expansion member 34 can extend from the expansion member 34, directly or indirectly, into and through the base 22 and out the base 22. The dilation member 24 can define an actuator retention channel 40 that is supported by the inner surface 25d of one or both of the expandable blades 32. For instance, the actuator retention channel 40 can extend into the inner surface 25d, or can be defined by structure that extends from the inner surface 25d into the second conduit 25c. The dilation member 24 can further include at least one retention rib 42 (see FIG. 6B) that extends across the channel 40 that retains at least a portion of the actuator 36 in the retention channel, thereby limiting or preventing movement of the actuator 36 from the channel into the second conduit 25c. Alternatively, the retention channel 40 can be defined by an aperture that extends through the respective expandable dilator blades. Thus, the actuator 36 can extend along the channel 40 that is defined by the dilation member 24 along a direction between the proximal end 25a and the distal end 25b. Alternatively, as illustrated in FIG. 3D, the expandable dilator 20 can define one or more apertures 51 that extend through the dilator body, for instance through the inner and outer surfaces 25d and 25e of the dilation member 24, or through the inner and outer surfaces 23d and 23e of the base 22. One or both of the first actuator and the second actuators 37 (described below) can extend out the dilator body 21 through a respective aperture 51.

Referring now to FIGS. 4A-B, the dilation member 24 can include at least one stop surface 39 supported by the dilation body 25, for instance at the inner surface 25d of one or more up to all of the dilator blades 32, including one or all of the expandable dilator blades 32. The stop surface 39 is configured to abut the expansion member 34 when the expansion member 34 has rotated to the expanded position. The stop surface 39 can be defined by a stop member 41 that extends from the inner surface 25d toward the longitudinal axis L. The stop member 41 can prevent the expansion member 34 from further rotating along the first rotational direction once the expansion member 34 has rotated to the expanded position. Alternatively or additionally, the at least one stop surface 39 can be defined by a groove 43 that is supported by the inner surface 25d of at least one or more up to all of the dilator blades 32, including one or all of the expandable dilator blades 32. For instance, the groove 43 can extend into the inner surface 25d along a direction away from the longitudinal axis L. The groove 43 is configured to frictionally receive the expansion member 34 once the expansion member 34 has rotated to the expanded position, thereby providing tactile feedback that the expansion member 34 is in the expanded position. It is also envisioned that each of the dilator blades 32 can include a plurality of grooves 43 that are spaced along the distal direction, such that each of the grooves can receive the expansion member 34 as the expansion member rotates from the first position to the expanded position. Accordingly, one or more of the grooves 43 can be configured to receive the expansion member in one or more intermediate positions between the first position and the dilated position, and provide tactile feedback to the user when it is desired to retain the dilator blades 32 in the intermediate position, and thus retain the dilation member 24 in an intermediate position that is between the first position and the expanded position.

With continuing reference to FIGS. 1A-3D, the actuator 36 can be a first actuator, and the expandable dilator 20 can further include a second actuator 37 that is coupled, directly or indirectly, to the expansion member 34 in the manner described above with respect to the first actuator 36. The second actuator 37 can be attached to the expansion member 34 at a location offset from the axis of rotation R along the select direction SD2, such that the axis of rotation R is disposed between the first and second actuators 36 and 37 with respect to the select direction SD2. The second actuator 37 is configured to receive an actuation force, for instance in the proximal direction, which can be referred to as a contraction force, and in-turn apply a corresponding biasing force to the expansion member 34 that causes the expansion member 34 to move from the expanded position to the first position. The second actuator 37 extends along the proximal direction from the expansion member 34 toward the base 22. A pulling force can be applied to the second actuator 37, which causes the second actuator 37 to apply the force in the proximal direction to the expansion member 34 that biases the expansion member 34 from the expansion position toward, for instance to, the first position. The second actuator 37 can extend from the expansion member 34 through the second conduit 25c, and into the first conduit 23c. The second actuator 37 can further extend through the proximal end 23a of the first conduit 23c, or can alternatively can extend out the aperture 51 as described above. Thus, the second actuator 37 can extend from the expansion member 34, directly or indirectly, into and through the base 22 and out the base 22.

Referring to FIGS. 5A-5C, it should be appreciated that the expansion member 34, and all expansion members described herein, can include at least one of a first expansion member segment 35a and a second expansion member segment 35b, each configured to move between a respective first position and a respective expanded position. Each of the first and second expansion member segments 35a and 35b can be rotatable with respect to the dilation member 24 in the manner described above with respect to the expansion member 34, and is configured to move at least a portion of the dilation member 24 from the first configuration to the expanded configuration. The portions of the dilation member 24 that are configured to be moved by the first and second expansion member segments 35a and 35b can be opposite from each other with respect to the longitudinal axis L, or otherwise angularly offset with each other. For instance, the first expansion member segment 35a can be operatively coupled to a first expandable dilator blade 32 of the first or second pair 31a or 31b, for instance of the second pair 31b as shown. Similarly, the second expansion member segment 35b can be operatively coupled to a second expandable dilator blade 32 of the first or second pair 31a or 31b, for instance of the second pair 31b as shown.

As illustrated in FIG. 5A, the attachment members 57 of each of the first and second expansion member segments 35a and 35b can be rotatably coupled to the dilation member 24, for instance to a stationary one of the blades 32 of one of the first and second pairs 31a or 31b, such as the first pair 31a as shown, to a common attachment member 55 of the dilation member 24 at each side of the dilation member 24 opposite the longitudinal axis L. The common attachment members 55 can, for example, be configured as an aperture of the type described above that is elongate and configured to receive both attachment member 57 at opposed ends of the expansion member segments 35a and 35b. Alternatively, as illustrated in FIG. 5C, the dilation member 24, for instance at a stationary one of the blades 32 of one of the first and second pairs 31a or 31b, such as the first pair 31a as shown, can include a pair of attachment members 55 at each side of the dilation member 24 opposite the longitudinal axis L. Thus, each attachment member 57 of the first and second expansion member segments 35a and 35b can be attached to a unique attachment member 55 in the manner described above.

The first actuator 36 can extend from the first expansion member segment 35a in the manner described above with respect to the expansion member 34, and the second actuator 37 can extend from the second expansion member segment 35b in the manner described above with respect to the expansion member 34. As illustrated in FIG. 5A and FIG. 5C, the first and second expansion member segments 35a and 35b can be in their respective first positions, prior to movement to their respective expanded positions, such that their perimeters P extend from their respective axes of rotation along the distal direction. Separate actuation forces, for instance expansion forces, can be independently applied to the first and second actuators 36 and 37 in the proximal direction as desired. The first and second actuators 36 and 37 can in-turn apply respective biasing forces in response to the respective actuation forces that cause the corresponding first and second expansion member segments 35a and 35b to rotate from their respective first positions to their respective expanded positions, whereby the perimeter abuts a stop surface, which can be configured as a respective groove 43 as described above. Separate actuation forces, for instance contraction forces, can further be independently applied to the first and second actuators 36 and 37 in the proximal direction as desired. The first and second actuators 36 and 37 can in-turn apply respective biasing forces in response to the respective actuation forces that cause the corresponding first and second expansion member segments 35a and 35b to rotate from their respective expanded positions to their respective first positions. When in their first positions, after movement to their respective expanded positions, the respective perimeters P can extend from their respective axes of rotation along the proximal direction. Thus, one or more of the dilator blades 32 can be selectively moved between their respective first position and their dilated position. While the expansion member 34 can include first and second expansion member segments 35a and 35b as described herein, it should be further appreciated that the expansion member 34 can alternatively include one of the first expansion member segments 35a and 35b.

Referring now to FIGS. 6A-6D, the expandable dilator 20 can further include at least one securement member 44 that is supported by the dilator body 21, for instance in from the inner surface that at least partially defines the dilator body conduit, which can include one or both of the first conduit 23c and the second conduit 25c, or out from the outer surface of the dilator body 21 that is opposite the inner surface. All of the securement members 44 can extend in from the inner surface of the dilator body 21 or out from the opposed outer surface of the dilator body 21 as desired, for instance depending on whether the actuators 36 and 37 extend through the conduits or through an aperture 51 and along the outer surface of the dilator body 21. The securement members 44 are configured to attach to respective ones of the actuators 36 and 37. For instance, one of the securement members 44 is configured to attach to the first actuator 36 as to prevent the actuator from moving in the distal direction from the base 22 toward the dilation member 24 after the actuator has biased the expansion member 34 to the expanded position, thereby retaining the expansion member 34 in the expanded position. One of the securement members 44 is further configured to attach to the second actuator 37. The securement member 44 can, for example, be supported by the base 22, the dilation member 24, or both. As illustrated in FIG. 6A, the securement member 44 can be configured as a cleat 46 that is supported by the dilator body 21, whereby the respective actuator is configured to be wrapped about the cleat 46, for instance in a figure-8 pattern, so as to retain the expansion member 34 in the expanded position. As illustrated in FIG. 6B, the securement member 44 can be configured as a set screw 48 that is threadedly supported by the dilator body 21, and rotatable with respect to the dilator body 21 so as to translate toward a surface of the dilator body 21, for instance of the retention rib 42, so as to capture the respective actuator between the set screw 48 and the surface of the dilator body 21. Alternatively still, as illustrated in FIGS. 6C-6D, the securement member 44 can be configured as a clamp 50 supported by the dilator body 21. The clamp 50 can define a groove 52 that is sized to receive the respective actuator such that the actuator 36 is compressed and captured in the groove 52. The groove can be defined by the outer surface of the dilator body 21, for instance the outer surface 23b of the base 22.

Referring now to FIGS. 7A-7F, it is recognized that expansion of the dilation member 24 can be resisted by the soft tissue that surrounds the dilation member 24. For instance, the soft tissue can apply a force to the outer surface 25e that resists movement of the dilation member 24 from the first configuration to the expanded configuration. Accordingly, the expandable dilator 20 can further include an actuation leverage member 54 that is supported by the dilator body 21. The actuation leverage member 54 is configured to receive an actuation force, alter the actuation force, and apply the altered actuation force through the actuator 36 to the expansion member 34 to move the expansion member 34 from the first position toward the expanded position, for instance to the expanded position. For instance, the actuation leverage member 54 is configured to receive a rotational force and alter the rotational force to a linear force that is applied to the expansion member 34. Alternatively or additionally, the actuation leverage member 54 is configured to increase or magnify the applied actuation force such that the altered force is an increased force or magnified force that is applied to the expansion member 34.

Figure 7B:
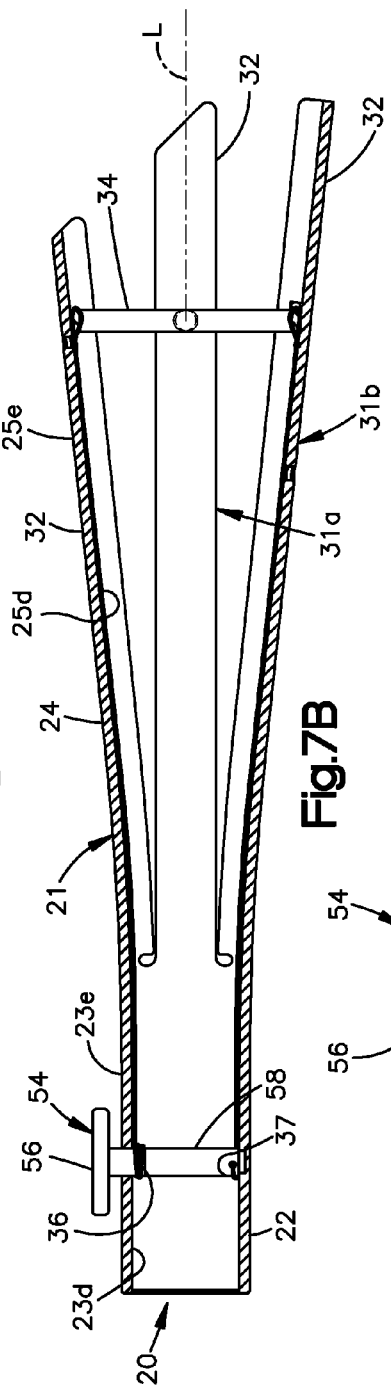
FIG. 7B is a sectional side elevation view of the expandable dilator illustrated in FIG. 1B, including the actuation leverage member illustrated in FIG. 7A.
Figure 7C:
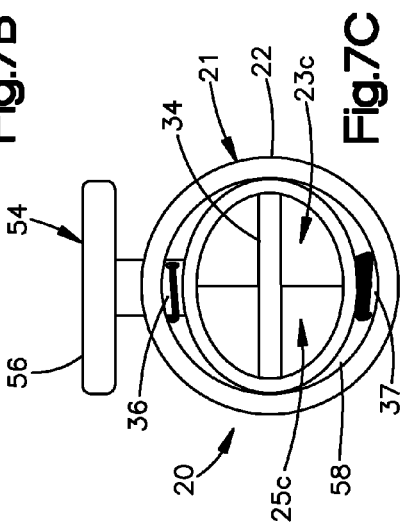
FIG. 7C is an end elevation view of the expandable dilator illustrated in FIG. 7A.

As illustrated in FIGS. 7A-7C, the leverage member 54 can be configured as a spindle or spool 56, which can be cylindrically or alternatively shaped so as to support a winding of actuator 36, that supported by the dilator body 21, for instance at the base 22, and is attached to the first actuator 36. The spool 56 can include a spool body 58 that is rotatable in a first rotational direction with respect to the dilator body 21 so as to cause the actuator 36 to wind around the spool body 58. The spool body 58 can define at least a portion of an annulus. For instance, the spool body 58 can define an annulus (for example ring-shaped) or a portion of an annulus (for example substantially C-shaped), such that the 56 defines a channel that extends through the spool body 58 that can be in alignment with the first conduit 23c and the second conduit 25c along the longitudinal axis L. The spool 56 is configured to receive an applied rotational force and alter the applied force to a linear force that is applied to the expansion member 34 through the actuator 36, thereby causing the expansion member 34 to move from the first position toward the expanded position. The spool 56 is further rotatable in a second rotational direction opposite the first rotational direction so as to cause the actuator 36 to unwind from the spool body 58. The spool 56 can further be attached to the second actuator 37 and can also be configured to wind about the spool body 58. Thus, rotation of the spool 56 in the first rotational direction causes the second actuator 37 to unwind from the spool body 58, and rotation of the spool in the second rotational direction causes the second actuator 37 to wind around the spool body 58, thereby causing the expansion member 34 to move from the expanded position toward the first position, for instance to the first position. The spool 56 can, for instance, be rotated in the first and second directions to a position whereby the spool body 58 extends substantially along the inner surface of the dilator body 21, which can include one or both of the inner surface 23d and the inner surface 25d.

As illustrated in FIG. 7D, the leverage member 54 can be configured as a pulley system including a pulley 60 that is mounted to the dilator body 21, such as the base 22 or the proximal end 25a of the dilation member 24. The pulley 60 can be rotatable with respect to the dilator body 21, or rotatably fixed to the dilator body 21. The expansion member 34 is spaced from the pulley 60 along the distal direction.

The actuator 36 extends from the expansion member 34 to the pulley 60, for instance along the proximal direction, extends around the pulley 60, and extends from the pulley 60 to a support member, for instance along the distal direction. The support member is spaced from the pulley 60 in the distal direction. The support member can be defined by another pulley supported by the dilator body 21, or can be defined by the expansion member 34. The actuator 36 extends around the support member, and extends from the support member along a proximal direction toward the base 22, for instance to the base 22, and can extend out the base 22 as described above. The pulley system can include as many pulleys and support members as desired. The pulley system is configured to receive an actuation force, magnify the force, and apply the magnified force to the expansion member 34.

Referring now to FIGS. 7E-7F, and as described above with respect to FIG. 2C, the actuator 36 can be substantially rigid, and configured as a rod 62. For instance, the rod 62 can be sufficiently rigid such that a compressive force applied along its length does not cause the rod 62 to buckle. Thus, the rod 62 is configured to receive an actuation force, in the proximal direction, as described above and in-turn apply a biasing force to the expansion member 34 along the proximal direction that causes the expansion member 34 to rotate from the first position to the expanded position. Similarly, the rod 62 is configured to receive an actuation force, for instance in the distal direction, which can be referred to as a contraction force, and in-turn and in turn apply a biasing force to the expansion member 34 along the proximal direction that causes the expansion member 34 to rotate from the expanded position to the first position. The rod 62 can be threadedly supported by the dilator body 21, for instance at the base 22, such that rotation of the rod 62 in a first rotational direction relative to the dilator body 21, or rotation of a nut relative to the dilator body 21, the nut supported by the dilator body 21 and threadedly receiving the rod 62, causes the rod 62 to translate with respect to the dilator body 21 along a direction that causes the expansion member 34 to move in a direction from the first position toward the expanded position. Rotation of the rod 62 in a second rotational direction relative to the dilator body 21 opposite the first direction causes the expansion member 34 to move in a direction from the expanded position toward the first position. Thus, the leverage member 54 can be configured as the rod 62, and can receive a rotational actuation force and alter the actuation force to a linear force that can cause the expansion member 34 to rotate.

Figure 8B:
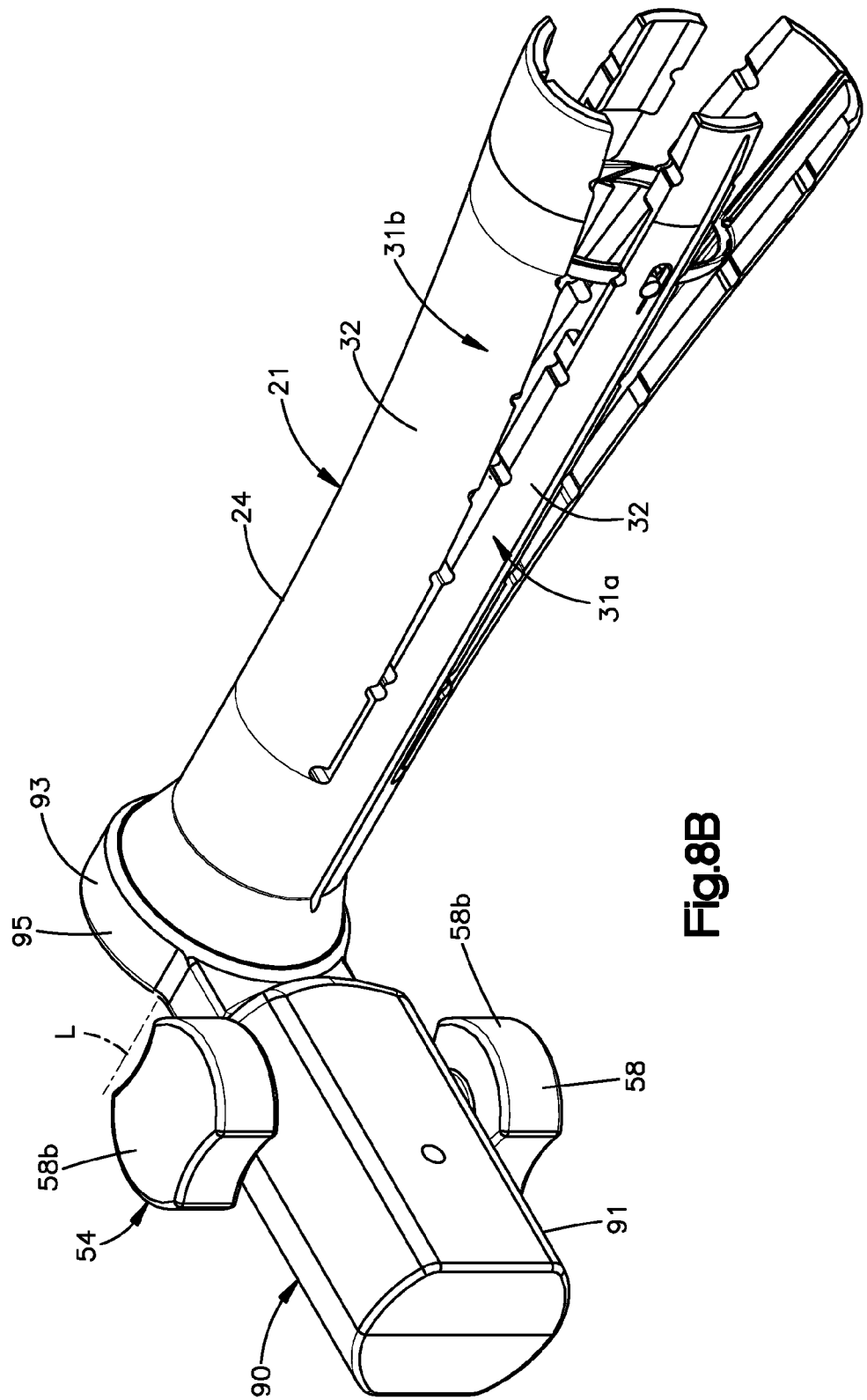
FIG. 8B is a perspective view of the expandable dilator illustrated in FIG. 8A, showing the expandable dilator blades in a dilated position.
Figure 8C:
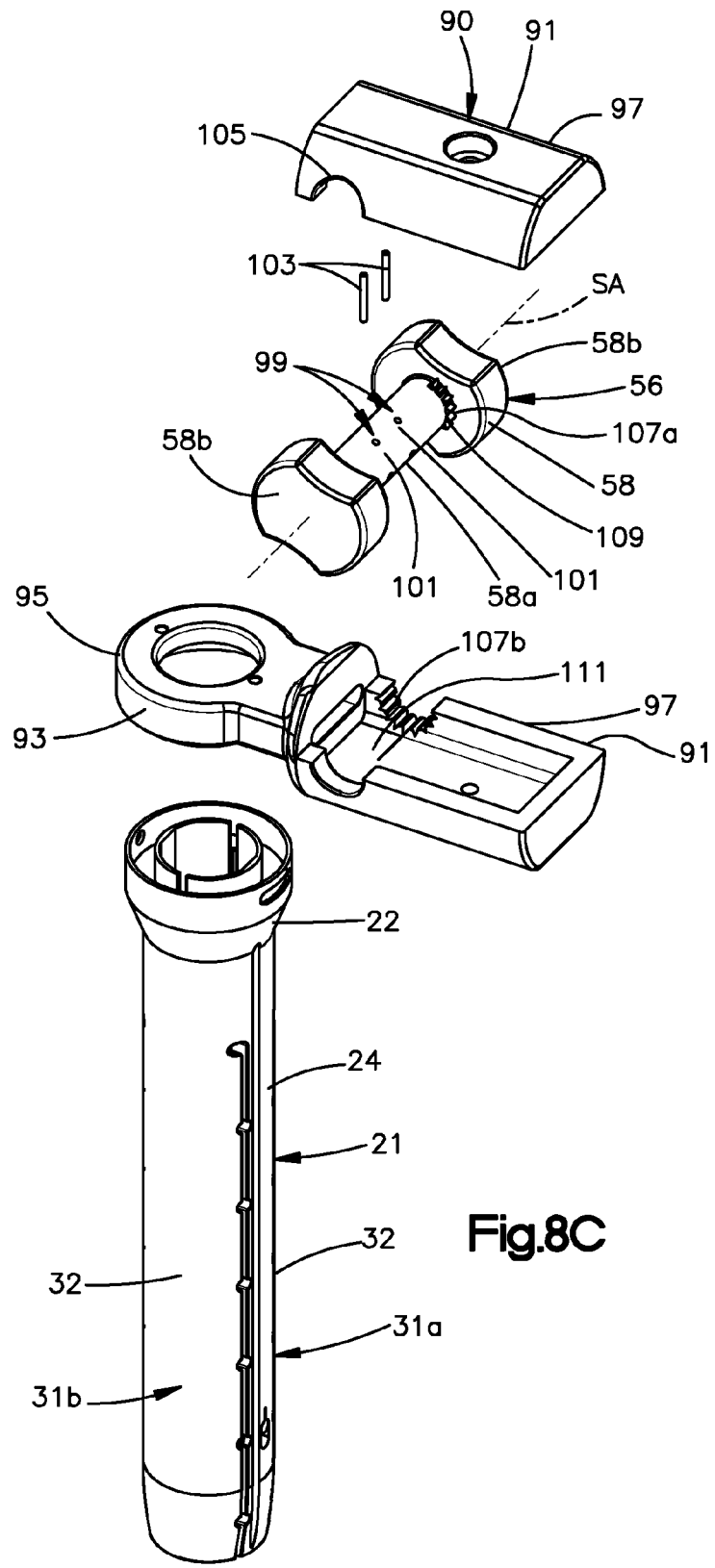
FIG. 8C is an exploded perspective view of a portion of the expandable dilator illustrated in FIG. 8A, showing the actuation leverage member.
Figure 8F:
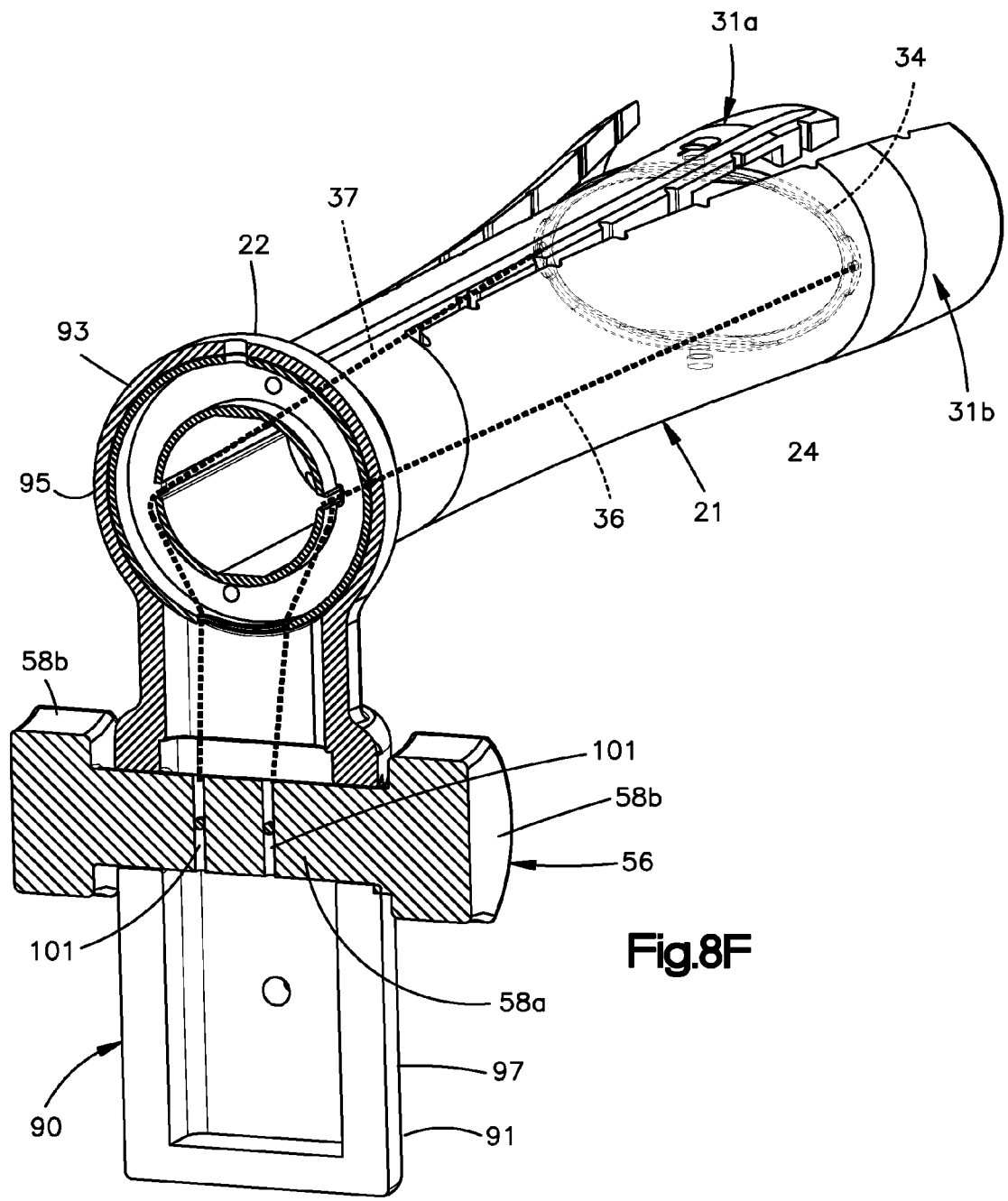
FIG. 8F is a sectional perspective view of the expandable dilator illustrated in FIG. D
Figure 8K:
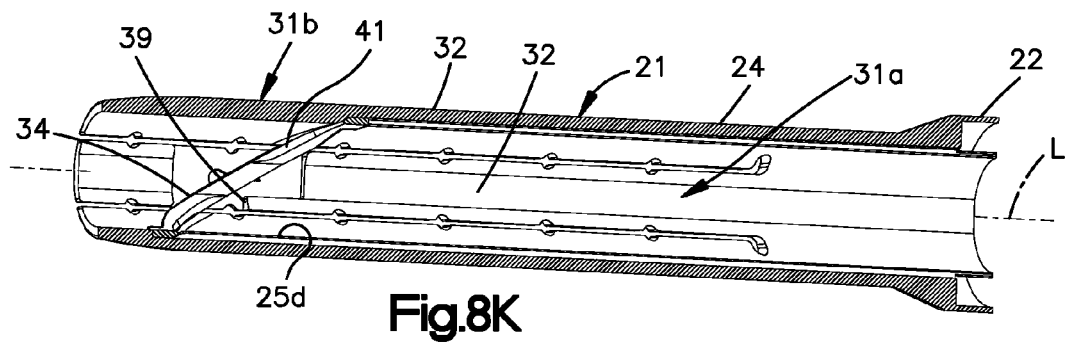
FIG. 8K is a sectional perspective view of a portion of the expandable dilator illustrated in FIG. 8A, showing a stop surface on one of the blades.
Figure 8L:
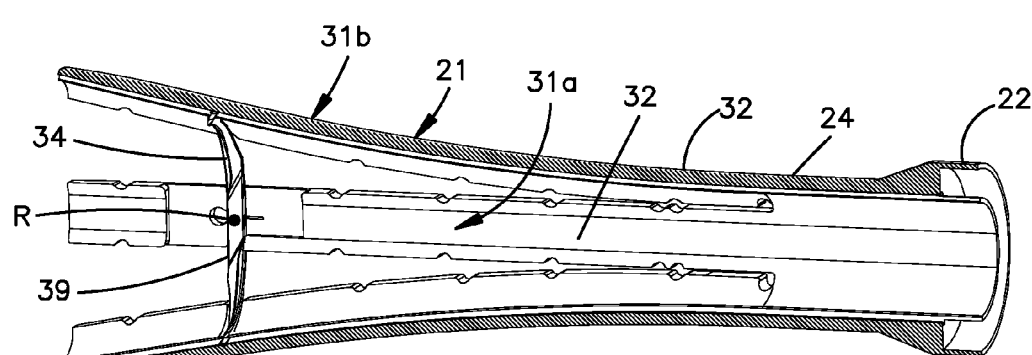
FIG. 8L is a sectional perspective view of a portion of the expandable dilator illustrated in FIG. 8B, showing the stop illustrated in FIG. 8K.
Figure 8M:
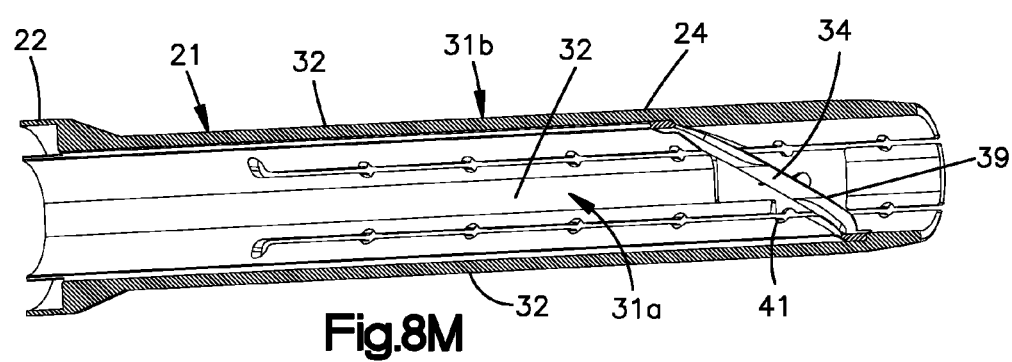
FIG. 8M is a sectional perspective view of a portion of the expandable dilator illustrated in FIG. 8A, showing a stop surface on another one of the blades.
Figure 8N:
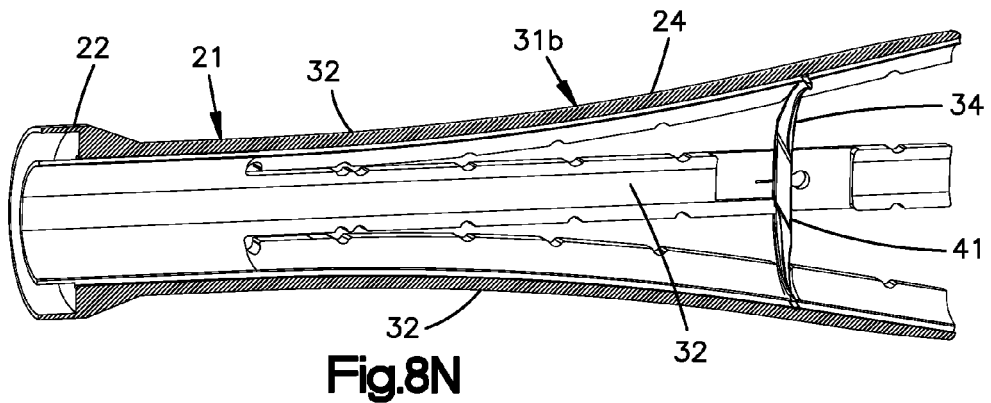
FIG. 8N is a sectional perspective view of a portion of the expandable dilator illustrated in FIG. 8B, showing the stop surface illustrated in FIG. 8M.

Referring also to FIGS. 8A-8C, the dilator body 21, and thus the expandable dilator 20, can include a handle 90 that can be supported by the base 22 or any other location of the dilator body 21. For instance, the handle 90 can be configured to attach to the base 22 or any other location of the dilator body 21. In accordance with the illustrated embodiment, the handle 90 extends out with respect to the base 22 along a direction that is angularly offset, for instance perpendicular, with respect to the longitudinal axis L. For instance, the handle 90 can include a handle body 91 and an attachment member 93 that is supported by the handle body 91. For instance, the attachment member 93 can extend from the handle body 91. The attachment member 93 can, for instance, include a wall 95 which can be an annular wall that is configured to receive the base 22, such that the base 22 is press-fit in the wall 95. It should be appreciated, of course, that the attachment can attach to the base 22 in any manner as desired. For instance, the wall 95 can be received by the base. Alternatively or additionally, an auxiliary attachment member, such as a one or more screws or locking pins or the like can attach the base 22 to the attachment member 93. Alternatively still, at least a portion of the handle body 91 can be monolithic with the base 22.

Referring also to FIGS. 8C-8E, the handle body 91 can be a one-piece handle body 91 or can include a plurality of handle body segments 97. For instance, the handle body 91 can define two handle body segments 97 that can be attached to each other. The handle body 91 can support the leverage member 54, which can be configured as a spool 56, which can be cylindrically or alternatively shaped, in the manner described above. Thus, the spool 56 can be configured to support a winding of at least one actuator 36 that is attached to the spool 56.

The spool 56 can include a spool body 58 that can include a shaft 58a and at least one knob 58b, such as a pair of knobs 58b. The shaft 58a is rotatable about a spool axis SA relative to the dilator body 21, and for instance relative to the handle 90. The shaft 58a can extend between the knobs 58b, and can be monolithic with the knobs 58b or attached to the knobs 58b in any manner as desired. Thus, the spool axis SA can extend through the knobs 58b, and can extend centrally through the shaft 58a. The expandable dilator 20 can include an aperture 105 that extends through the dilator body 21. For instance, the handle 90 can include the aperture 105 that extends through the handle body 91. The aperture 105 can be sized such that the spool shaft 58a extends through the aperture, such that the dilator body 21, for instance the handle body 91, is disposed between the knobs 58b. The spool 56 can define at least one attachment member 99 that is configured to attached to a respective at least one actuator 36. For instance, the attachment member 99 can be configured as an aperture 101 that extends at least into or through the spool body 58, for instance the spool shaft 58a. The aperture 101 can be sized to receive the respective actuator 36. The spool 56 can further include at least one locking member such as a locking pin 103 that is configured to be inserted into the aperture 101 so as to secure the respective actuator 36. For instance, the locking pin 103 can be press-fit into the aperture 101 so as to capture the respective actuator 36 or 37 between the locking pin 103 and the spool body 58 in the corresponding aperture 101. It should be appreciated, of course, that the actuator 36 can be attached to the spool body 58 in accordance with any alternative embodiment as desired.

The spool 56 and the dilator body 21, for instance the handle 90, can include complementary locking members 107a and 107b, respectively. The spool 56 is movable with respect to the dilator body 21, for instance the handle 90, between a first unlocked position whereby the locking members 107a and 107b are disengaged and a second locked position whereby the locking members 107a and 107b are engaged with each other. When the locking members 107a and 107b are disengaged, the spool 56 is rotatable with respect to the dilator body 21, such as the handle 90, about the spool axis SA. When the locking members 107a and 107b are engaged, the spool 56 is locked from rotation relative to the dilator body 21, such as the handle 90. In accordance with one embodiment, the locking member 107a of the spool 56 comprises at least one tooth 109, such as a plurality of teeth 109, that extend out from the spool body 58. For instance, the teeth 109 can extend out from the spool shaft 58a away from the spool axis SA, though it should be appreciated that the teeth 109 can alternatively extend out from any suitable surface of the spool body 58. In accordance with the illustrated embodiment, the teeth 109 can be spaced circumferentially about each other about at least a portion of the outer surface of the spool body 58, for instance of the shaft 58a. The teeth 109 can define a length 109 along the spool axis SA that is less than a length that the shaft 58a extends out from the dilator body 21, such as the handle 90.

In accordance with one embodiment, the locking member 107b of the dilator body 21, such as the handle 90, comprises at least one tooth 119, such as a plurality of teeth 111. The teeth 111 can be complementary to the teeth 109 and configured to intermesh with the teeth 109. The teeth 111 can at least partially define the aperture 105. During operation, the spool 56 can move relative to the dilator body 21 such as the handle 90, for instance translate along the spool axis SA, between a first or unlocked position whereby the teeth 109 and 111 are disengaged, for instance spaced from each other along the spool axis SA, and a second locked position whereby the teeth 109 and 111 intermesh. When the spool 56 is in the locked position such that the teeth 109 and 111 intermesh, the engagement between the teeth 109 and 111 lock the spool 56 from rotation relative to the dilator body 21, such as the handle 90. When the spool 56 is in the unlocked position, the spool 56 is rotatable about the spool axis SA with respect to the dilator body 21, for instance the handle 90. While the teeth 109 and 111 are defined by the shaft 56 and the handle 90, respectively, in accordance with one embodiment, it should be appreciated that the teeth can extend from any surface of the spool 56 and the dilator body 21 as desired, and the spool 56 can move relative to the dilator body 21 along any direction as desired between the unlocked and the locked positions. Further, the expandable dilator 20 can include any suitable retention member as desired to retain the spool 56 in one or selectively in both the unlocked and the locked positions. For instance, the retention member can include a spring member supported by at least one of the dilator body 21 and the spool 56 that biases the spool 56 to one of the unlocked position and the locked position. Alternatively, the retention member can be configured as an interference with the handle 90 that provides a resistance to movement of the handle 90 from the locked position to the unlocked position, from the unlocked position to the locked position, or both.

As described above, the expandable dilator 20 can include a first actuator 36 and a second actuator 37 that are attached to respective ones of the attachment members 99, which can be spaced from each other along the spool axis SA. For instance, the actuators 36 and 37 can be inserted into respective ones of the apertures 101, and the respective locking pins 103 can be inserted into the respective aperture 101 so as to capture the actuators 36 and 37 therein, thereby attaching the first and second actuators 36 and 37 to the spool 56, and in particular to the shaft 58a.

Referring also to FIGS. 8G-8H, a the first and second actuators 36 and 37 can be attached to the expansion member 34 in the manner described above, such that the actuation force applied to the first actuator 36 causes the expansion member 34 to move from the first position to the expanded position, and the actuation force applied to the second actuator 36 causes the expansion member 34 to move from the expanded position to the first position. The spool 56, for instance at one or both of the knobs 58b, is configured to receive an applied rotational force in a first rotational direction or in a second rotational direction that causes the spool 56 to rotate about the spool axis SA in the first rotational direction or the second rotational direction, respectively, relative to the dilator body 21, for instance the handle 90. The applied rotational force can be manually applied or applied by a motor that is supported by the dilator body 21 and coupled to the spool 56 at any location of the spool body 58. The spool 56 is configured to receive an applied rotational force and alter the applied rotational force to a linear force that is applied to the expansion member 34 through the first actuator 36, thereby causing the expansion member 34 to move from the first position toward, for instance to, the expanded position. Similarly, the spool 56 is configured to receive an applied rotational force and alter the applied rotational force to a linear force that is applied to the expansion member 34 through the second actuator 37, thereby causing the expansion member 34 to move from the expanded position toward, for instance to, the first position.

In accordance with one embodiment, one of the first and second actuators 36 and 37 can be wound about the shaft 58a along a first rotational direction, for instance a clockwise direction, while the other of the first and second actuators 36 and 37 can be wound about the shaft 58a along a second rotational direction, for instance a counterclockwise direction. Thus, rotation of the spool 56 in the second rotational direction, for instance the counterclockwise direction, causes the first actuator 36 to wind about the shaft 58b, and causes the second actuator 37 to unwind from the shaft 58b. As the first actuator 36 is wound about the shaft 58b, the first actuator 36 applies a force that causes the expansion member 34 to rotate in a direction from the first position to the expanded position. Because the second actuator 37 unwinds about the shaft 58 as the spool 56 is rotated in the second rotational direction, the length of the second actuator 37 increases so as to not prevent rotation of the expansion member 34 in the direction from the first position to the expanded position. The second actuator 37 can be completely unwound from the shaft 58b when the expansion member 34 is in the expanded position, or can be partially wound about the shaft 58b when the expansion member 34 is in the expanded position, but less wound about the shaft 58b than when the expansion member 34 is in the first position. It should be appreciated that the rate that the first actuator 36 winds about the shaft 58b can be equal to the rate that the second actuator 37 unwinds from the shaft 58b when the spool 56 is rotated in the second rotational direction.

Conversely, rotation of the spool 56 in the first rotational direction, for instance the clockwise direction, causes the second actuator 37 to wind about the shaft 58b, and causes the first actuator 36 to unwind from the shaft 58b. As the second actuator 37 is wound about the shaft 58b, the second actuator 37 applies a force that causes the expansion member 34 to rotate in a direction from the expanded position to the first position. Because the first actuator 36 unwinds about the shaft 58b as the spool 56 is rotated in the first rotational direction, the length of the first actuator 36 increases so as to not prevent rotation of the expansion member 34 in the direction from the expanded position to the first position. The first actuator 36 can be completely unwound from the shaft 58b when the expansion member 34 is in the first position, or can be partially wound about the shaft 58b when the expansion member 34 is in the first position, but less wound about the shaft 58b than when the expansion member 34 is in the expanded position. It should be appreciated that the rate that the second actuator 37 winds about the shaft 58b can be equal to the rate that the first actuator 36 unwinds from the shaft 58b when the spool 56 is rotated in the first rotational direction.

As described above, the spool 56 is movable with respect to the dilator body 21, for instance the handle 90, between the first unlocked position whereby the locking members 107a and 107b are disengaged and the second locked position whereby the locking members 107a and 107b are engaged with each other. The locking members 107a and 107b, when disengaged from each other, do not prevent the spool 56 from rotating selectively in the first and second rotational directions, respectively, in response to the applied force. The locking members 107a and 107b, when engaged with each other, prevent spool 56 from rotating selectively in both the first and second rotational directions, respectively, in response to the applied force. During operation, the spool 56 can be moved to the second locked position when the expansion member 34 has expanded the respective blades 32 a desired amount, even though the expansion member 34 is not in the full expanded position. Thus, movement of the spool 56 to the second locked position can cause the expansion member 34 to be fixed in a locked position between the first position and the expanded position.

Referring now to FIGS. 8I-8J, it should be appreciated that the first actuator 36 and the second actuator 37 can be monolithic with each other, so as to define a single actuator 36. Otherwise stated, the expandable dilator 20 can include a single actuator that extends through the spool body 58, and is coupled at each of its opposed ends to the expansion member, for instance at attachment locations that are disposed on opposite sides of the axis of rotation R along the select direction SD2 (see FIGS. 1-3D). Thus, reference to the first and second actuators 36 and 37 can be made with respect to two separate actuators or one monolithic actuator that includes the first and second actuators 36 and 37, which for the purposes of clarity can also be referred to as first and second actuator segments that are monolithic with each other so as to define a single actuator. As illustrated in FIGS. 8I and 8J, the single actuator can be fed through a channel 113 that extends into and out the spool body 58, for instance through the shaft 58b, such that the first and second actuator segments 36 and 37 extend out the shaft 58b from opposed ends of the channel 113. It should thus further be appreciated that the spool 56 is configured to attach to at least one actuation strand that is coupled to the expansion member 24 at two locations, and is rotatable so as to cause the expansion member to selectively move both in a direction from the first position toward the expanded position and in a direction from the expanded position toward the first position.

As described above with reference to FIGS. 8G-8H, one of the first and second actuator segments 36 and 37 of FIGS. 8I-8J is wound, or configured to wind, about the shaft 58a along a first rotational direction, for instance a clockwise direction, while the other of the first and second actuator segments 36 and 37 is wound, or configured to wind, about the shaft 58a along a second rotational direction, for instance a counterclockwise direction. Thus, rotation of the spool 56 in the second rotational direction, for instance the counterclockwise direction, causes the first actuator segment 36 to wind about the shaft 58b, and causes the second actuator segment 37 to unwind from the shaft 58b. As the first actuator segment 36 is wound about the shaft 58b, the first actuator segment 36 applies a force that causes the expansion member 34 to rotate in a direction from the first position to the expanded position. Because the second actuator segment 37 unwinds about the shaft 58 as the spool 56 is rotated in the second rotational direction, the length of the second actuator segment 37 increases so as to not prevent rotation of the expansion member 34 in the direction from the first position to the expanded position. The second actuator segment 37 can be completely unwound from the shaft 58b when the expansion member 34 is in the expanded position, or can be partially wound about the shaft 58b when the expansion member 34 is in the expanded position, but less wound about the shaft 58b than when the expansion member 34 is in the first position. It should be appreciated that the rate that the first actuator segment 36 winds about the shaft 58b can be equal to the rate that the second actuator segment 37 unwinds from the shaft 58b when the spool 56 is rotated in the second rotational direction.

Conversely, rotation of the spool 56 in the first rotational direction, for instance the clockwise direction, causes the second actuator segment 37 to wind about the shaft 58b, and causes the first actuator segment 36 to unwind from the shaft 58b. As the second actuator segment 37 is wound about the shaft 58b, the second actuator segment 37 applies a force that causes the expansion member 34 to rotate in a direction from the expanded position to the first position. Because the first actuator segment 36 unwinds about the shaft 58b as the spool 56 is rotated in the first rotational direction, the length of the first actuator segment 36 increases so as to not prevent rotation of the expansion member 34 in the direction from the expanded position to the first position. The first actuator segment 36 can be completely unwound from the shaft 58b when the expansion member 34 is in the first position, or can be partially wound about the shaft 58b when the expansion member 34 is in the first position, but less wound about the shaft 58b than when the expansion member 34 is in the expanded position. It should be appreciated that the rate that the second actuator segment 37 winds about the shaft 58b can be equal to the rate that the first actuator segment 36 unwinds from the shaft 58b when the spool 56 is rotated in the first rotational direction.

As described above, the spool 56 is movable with respect to the dilator body 21, for instance the handle 90, between the first unlocked position whereby the locking members 107a and 107b are disengaged and the second locked position whereby the locking members 107a and 107b are engaged with each other. The locking members 107a and 107b, when disengaged from each other, do not prevent the spool 56 from rotating selectively in the first and second rotational directions, respectively, in response to the applied force. The locking members 107a and 107b, when engaged with each other, prevent spool 56 from rotating selectively in both the first and second rotational directions, respectively, in response to the applied force. During operation, the spool 56 can be moved to the second locked position when the expansion member 34 has expanded the respective blades 32 a desired amount, even though the expansion member 34 is not in the full expanded position. Thus, movement of the spool 56 to the second locked position can cause the expansion member 34 to be fixed in a locked position between the first position and the expanded position.

Referring now to FIGS. 8K-8N, and as described above, the dilation member 24 can include at least one stop surface 39 supported by the dilation body 25, for instance at the inner surface 25d of one or more up to all of the dilator blades 32. In accordance with one embodiment, the at least one stop surface 39 is supported at the inner surface 25d of one or both of the dilator blades 32 to which the expansion member 34 is rotatably coupled, for instance the dilator blades 32 of the second pair 31b. As is described below, the dilation body 25 can include a light guiding insert that is supported along the inner surface of one or more of the dilator blades 32. It should be appreciated that the guiding insert can include the stop surface 39, and that in such embodiments, the stop surface 39 can still be said to be supported by the inner surface 25d of the respective dilator blade 32.

The stop surface 39 is configured to abut the expansion member 34 when the expansion member 34 has rotated to the expanded position. The stop surface 39 can be defined by a stop member 41 configured as a shoulder that extends in from the inner surface 25d toward the longitudinal axis L. The stop member 41 can prevent the expansion member 34 from further rotating along the first rotational direction once the expansion member 34 has rotated to the expanded position. The stop surfaces can be offset from the axis of rotation R along the longitudinal axis L a distance substantially equal to the thickness of the expansion member 34, such that the expansion member 34 can be in the fully expanded position when the expansion member 34 abuts the stop surface 39.

Referring now to FIGS. 9A-C, it should be appreciated that the expansion member 34 can alternatively define first and second expansion member segments that are independently rotatable about respective axes of rotation. The first actuator 36 can be coupled to the first expansion member segment, and the second actuator 37 can be coupled to the second expansion member segment. Accordingly, when a first expansion force is applied to the first actuator 36, the first actuator 36 causes the first expansion member segment to rotate about its axis of rotation and expand one of the dilator blades 32 of the second pair 31b from the first position to the dilated position. When a second expansion force is applied to the second actuator 37, the second actuator 37 causes the second expansion member segment to rotate about its axis of rotation and expand the other of the dilator blades 32 of the second pair 31b from the first position to the dilated position. The actuators 36 and 37 can be substantially rigid or otherwise configured to independently cause the respective first and second expansion member segments to retract from the respective expanded positions to the respective first positions.

As illustrated in FIG. 9A-9C, an expandable dilator assembly 64 can include the expandable dilator 20 that can be constructed in accordance with any embodiment described herein. The expandable dilator assembly 64 can further include an auxiliary expansion member 66 that is insertable into the second conduit 25c in a first position, and is expandable along a direction that is substantially perpendicular to the longitudinal axis L from the first position to an expanded position, such that expansion of the auxiliary expansion member 66 biases the dilation member 24 to expand from the first configuration at least toward the expanded configuration. The expansion member 34 can further be actuated from the first position to the expanded position in the manner described above to retain the dilation member 24 in the expanded configuration, or to assist the auxiliary expansion member 66 in expanding the dilation member 24. Thus, subsequent movement of the expansion member 34 to the expanded position after the auxiliary expansion member 66 has expanded from the respective first position to the respective expanded position retains the dilation member 24 in the expanded configuration.

Figure 9D:
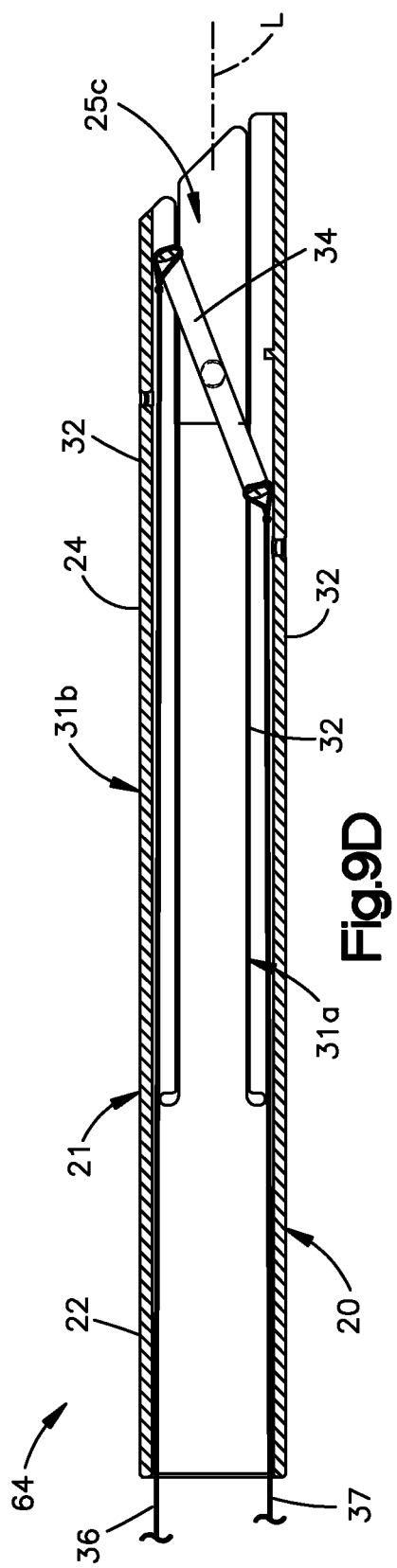
FIG. 9D is a sectional side elevation view of the expandable dilator as illustrated in FIG. 9C, showing the expansion member in a first configuration showing the dilator blades in the first position upon completion of a surgical procedure.

For instance, as illustrated in FIGS. 9A-9C, the auxiliary expansion member 66 can be configured as pliers 70 having opposed arms 72a and 72b that are configured to be inserted in the first position into the second conduit 25c, for instance along the distal direction. The pliers 70 can be actuated to move at least one or both of the arms 72a and 72b away from the other of the arms 72a and 72b, thereby expanding the pliers from the first configuration to the expanded configuration. The arms 72a and 72b can bear against the inner surface 25d of the dilation member 24. Once the expansion member 34 is in the expanded position, the pliers 70 can be actuated to bring the arms 72a and 72b together, and the pliers 70 can then be removed from the second conduit 25c, as illustrated in FIG. 9C. The expansion member 34 can then be moved from the expanded position to the first position after completion of the surgical procedure, as illustrated in FIG. 9D. It should be appreciated that the pliers 70 have been illustrated in accordance with one embodiment, and that the auxiliary expansion member 66 can be constructed in accordance with any alternative embodiment that is suitable to be inserted into the second conduit 25c and expanded so as to move at least one or both of the arms 72a and 72b away from the other of the arms 72a and 72b.

Referring now to FIGS. 23A-C, the dilation member 24 can be made from a resiliently flexible material, and the attachment member 55 of the dilation member 24 can define a track 80 that is supported by, for instance formed in, the dilation member 24 and can extend between proximal end 25a and the distal end 25b. In accordance with the illustrated embodiment the dilation member 24 defines a track 80 that extends through each of the dilator blades 32 of the first pair 31a. The expandable dilator 20 can further include an expansion device 82 that is attachable to the dilation member 24, and slidable along the track 80 between the proximal end 25a and the distal end 25b. The expansion device 82 can have having a cross-sectional dimension greater than that of the second conduit 25c, or can be expandable to the cross-sectional dimension, such that the expansion device expands the dilation member 23 from the first configuration to the expanded configuration at a region 24f that is local to the expansion device 82, such that distant regions 24g of the expansion member 34 that are distant from the expansion device 82 are not expanded. The local region 24g can return from the expanded configuration to the first configuration after the expansion device 82 has traveled along the track away from the local region 24g. Thus, movement of the expansion device 82 to a location proximate to the distal end 25b causes the distal end 25b to expand from the first configuration to the expanded configuration. In accordance with one embodiment, the expansion device 82 can be configured as the expansion member 32 that is slidably mounted to the expansion member 34.

Figure 10F:
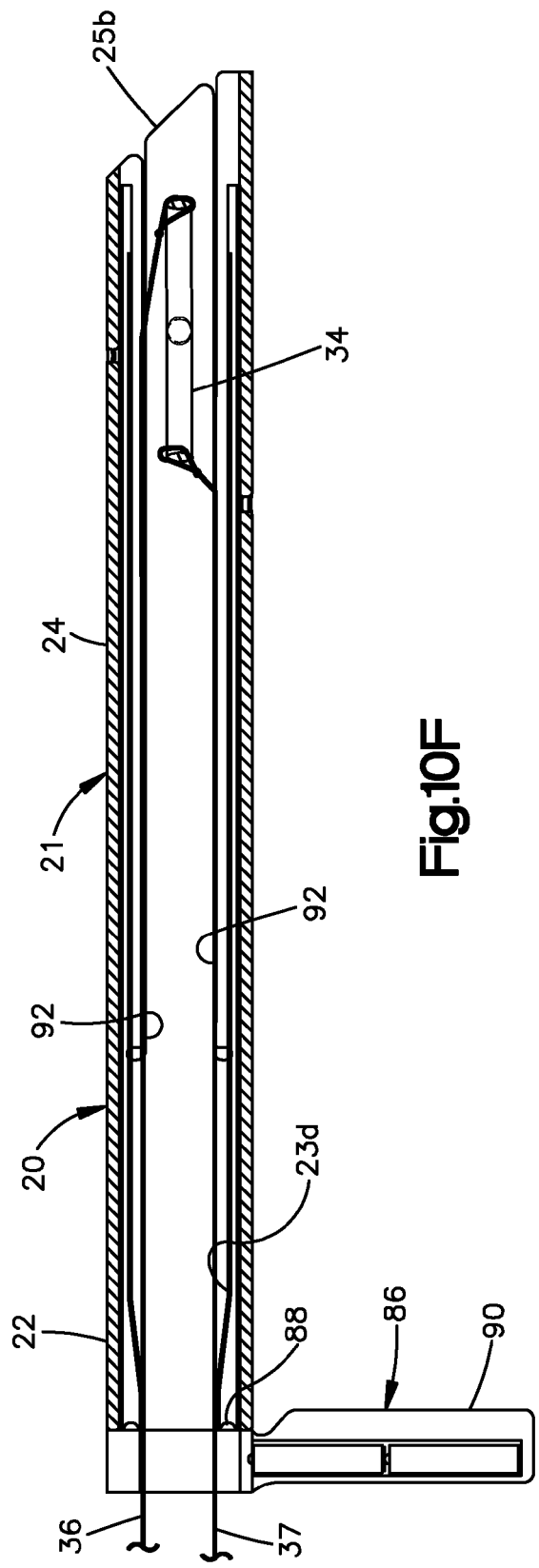
FIG. 10F is a sectional side elevation view of the expandable dilator as illustrated in FIG. 10A, but showing the illumination assembly constructed in accordance with an alternative embodiment.

Referring now to FIGS. 10A-10F, the expandable dilator 20 can include an illumination assembly 86 that, in turn, can include at least one illumination source 88 such as a plurality of illumination sources 88, that are supported by the dilator body 21 and are configured to emit light to the second conduit 25c at the distal end 25b such that the light extends out the distal end 25b to the target surgical site. In accordance with the embodiment illustrated in FIG. 10A, the illumination sources 88 are disposed about the inner surface 23d of the base 22, though it should be appreciated that one or more up to all of the illumination sources 88 can be disposed about the inner surface of the dilation member 24. As illustrated in FIG. 10F, the illumination assembly can include a pair of illumination sources 88 that are aligned with respective ones of the expandable dilator blades 32, though it should be appreciated the illumination sources 88 can alternatively or additionally be aligned with the one or more dilator blades 32 to which the expansion member 34 is rotatably coupled.

The illumination sources 88 can be configured as light emitting diodes, incandescent light sources, laser light sources, or any suitable alternative light sources as desired. The illumination assembly 86 can include a handle 90 that extends out from the base, and can be configured to deliver power to the illumination sources 88 so as to cause the illumination sources 88 to illuminate. For instance, the handle 90 can carry electrochemical batteries that are in electrical communication with the illumination sources, or can be plugged into an electrical receptacle so as to deliver power from the electrical receptacle to the illumination sources 88.

The illumination assembly 86 can further include one or more light conduits 92 that extends from the illumination sources 88 toward, for instance to, the distal end 25b. The light conduits 92 can be configured to transmit light emitted from the corresponding illumination source 88 to the distal end 25b. The light conduits 92 can be substantially opaque from the corresponding light source 88 to a location spaced proximally from the distal end 25b, and can be at least translucent or transparent at the distal end 25b, so as to emit light at the distal end 25b and out the distal end 25b of the second conduit 25c. As illustrated in FIG. 10C, the inner surface 25d of each of the dilator blades 32 can define one or more light transmitting channels 94 that can support the light conduit 92 disposed therein. Alternatively, the light transmitting channels can receive illumination from the illumination sources 88 and transmit the illumination to the distal end 25b.

As illustrated in FIGS. 10B, 10D, and 10E, the distal end 25b of the dilation member 24 can include at least one light shaping element 96 that can be supported by the inner surface 25d. The light shaping elements 96 can include one or more, up to all, of a plurality of prisms 98 supported by the inner surface 25d at the distal end 25b, a roughened textured region 100 of the inner surface 25d at the distal end 25b, and a reflective material 102, such as a foil, supported by the inner surface 25d at the distal end 25b. The light illuminated by the illumination sources 88 can thus be shaped, for instance diffused, prior to being directed out the distal end 25b of the second conduit 25c.

Figure 11A:
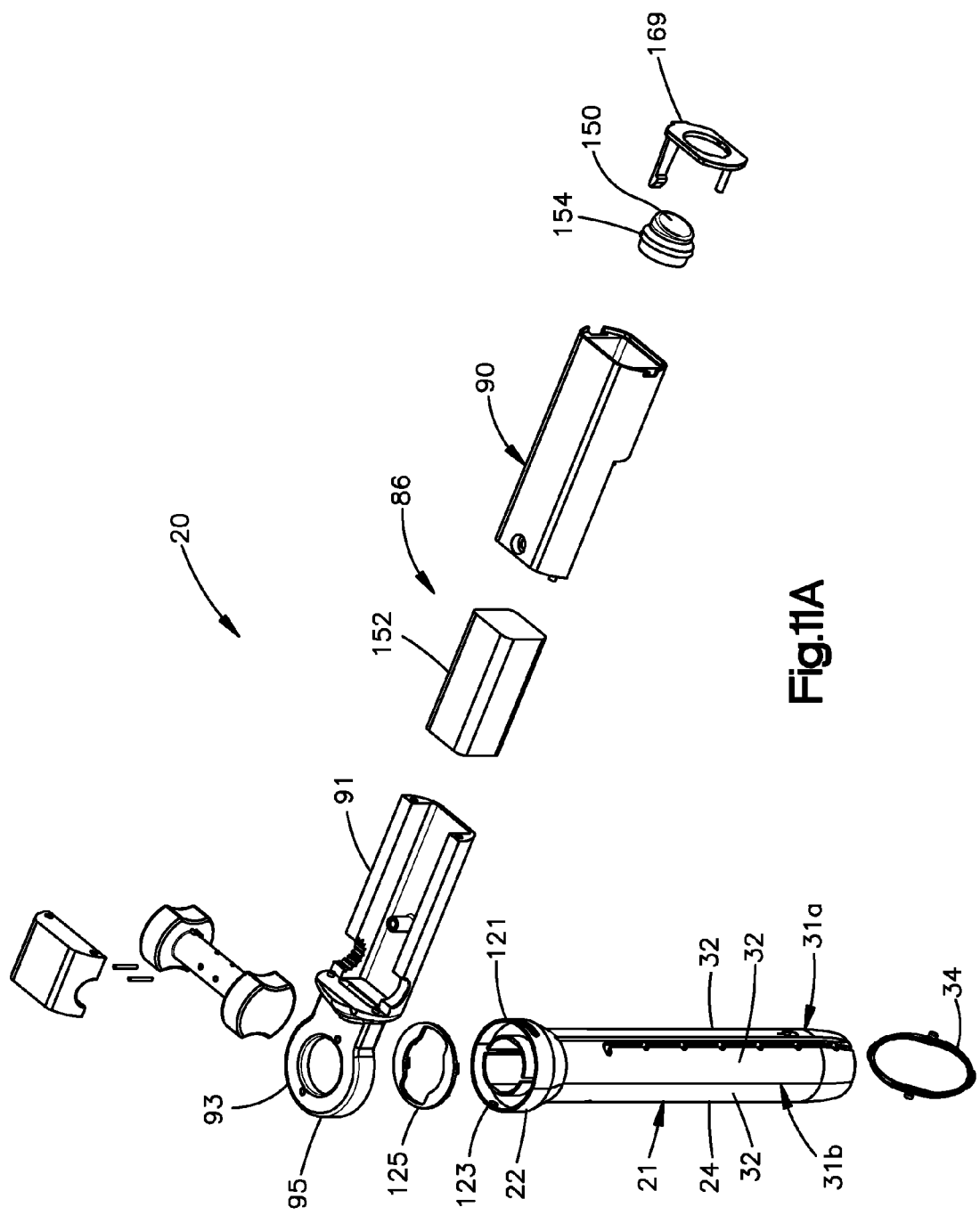
FIG. 11A is an exploded perspective view of the expandable dilator as illustrated in FIG. 1A, including an illumination assembly constructed in accordance with another embodiment.

Referring generally to FIGS. 11A-11O, it should be appreciated that the illumination assembly 86 can be constructed in accordance with any suitable alternative embodiment as desired. As described above, the illumination assembly 86 can include at least one illumination source 88 that is configured to emit illumination to the dilation member 24. At least a portion of the dilation member 24 is transparent such that at least a portion of the emitted illumination travels to the distal end of the dilation member 24. Thus, the at least one illumination source 88 can be disposed proximal with respect to the dilation member 24, and direct the illumination distally along the transparent portion of the dilation member 24.

Figure 11B:
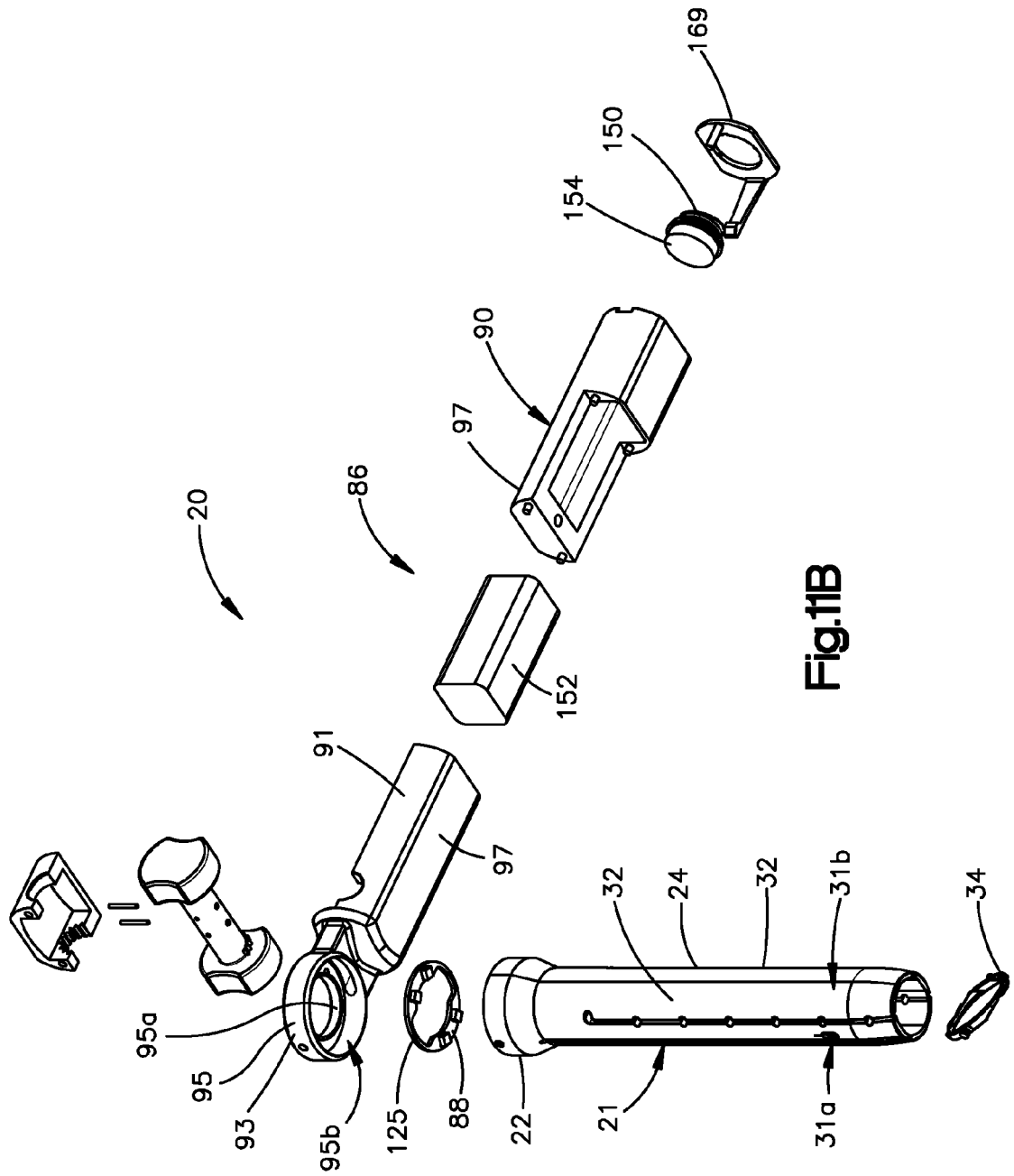
FIG. 11B is an exploded perspective view of the expandable dilator illustrated in FIG. 11A, including an illumination assembly constructed in accordance with another embodiment.
Figure 11C:
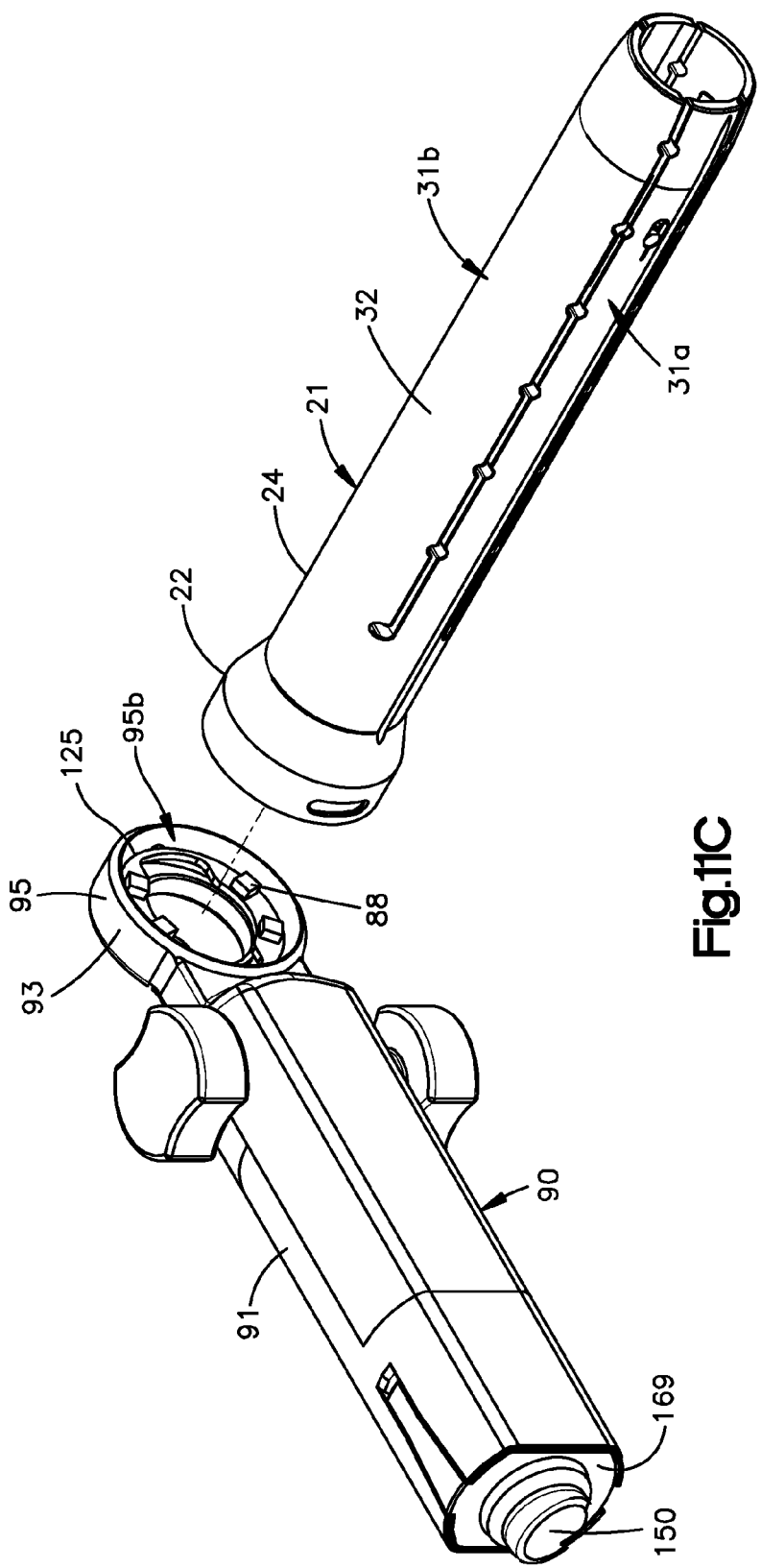
FIG. 11C is another exploded perspective view of the expandable dilator illustrated in FIG. 11A.

As illustrated in FIGS. 11A-C, the dilator body 21 can include the base 22 and the dilation member 24, and at least a portion up to all of the illumination assembly 88 is carried by the dilator body 21. As described above with respect to FIG. 8C, the dilator body 21, and thus the expandable dilator 20, can include a handle 90 that can be supported by the base 22 or any other location of the dilator body 21. For instance, the handle 90 can be configured to attach to the base 22 or any other location of the dilator body 21. In accordance with the illustrated embodiment, the handle 90 extends out with respect to the base 22 along a direction that is angularly offset, for instance perpendicular, with respect to the longitudinal axis L. For instance, the handle 90 can include a handle body 91 and an attachment member 93 that is supported by the handle body 91. For instance, the attachment member 93 can extend from the handle body 91. The attachment member 93 can, for instance, include a wall 95 which can be an annular wall that is configured to receive the base 22, such that the base 22 is press-fit in the wall 95. It should be appreciated, of course, that the attachment can attach to the base 22 in any manner desired. For instance, the wall 95 can be received by the base. Alternatively or additionally, an auxiliary attachment member, such as a one or more screws or locking pins or the like can attach the base 22 to the attachment member 93. Alternatively still, at least a portion of the handle body 91 can be monolithic with the base 22.

In accordance with one embodiment, the at least one illumination source 88 can be carried by the base 22. The illumination assembly 86 can include an illumination substrate, such as a printed circuit board 125, such that the at least one illumination source is carried by the illumination printed circuit board 125. The base 22 can include an outer annular wall 121 that surrounds the proximal end of the dilation member 24, for instance the blades 32, so as to define an annular void 123 between the outer annular wall 121 and the proximal end of the dilation member 24. The printed circuit board 125 can be annular and sized to be received in the annular void 123 such that the at least one illumination source 88 faces the distal direction. The handle 90 can be attached to the base 22, for instance by inserting the outer annular wall 121 into the annular wall 95 of the handle 90. Alternatively, the at least one illumination source 88 can be carried by the handle 90. For instance, the handle 90 can include an inner annular wall 95a disposed radially inward of the annular wall 95 so as to define an annular void 95b between the annular walls 95 and 95a. The inner annular wall 95a can receive the proximal end of the dilation member 24 when the handle 90 is attached to the base 22. The illumination printed circuit board 125 can be disposed in the annular void 95b, and positioned such that the at least one illumination source 88 faces the distal direction.

With continuing reference to FIGS. 11A-11B, the illumination assembly 86 can further include any suitable power source that can be external or configured as an electrochemical battery 152 that is configured to deliver power to the at least one illumination source 88. The at least one illumination source can be configured as a light emitting diode (LED), an incandescent light source, a halogen light source, a laser light source, or any suitable alternative light source as desired. The illumination assembly 86 can further include an actuator 150 that can, for instance, be carried by the handle 90 or any alternative location of the dilator body 21. Actuation of the actuator 150 can cause electrical power to flow from the power source to the printed circuit board 125, and hence to the at least one illumination source 88, thereby causing the illumination source 88 to emit illumination in the manner described herein. The actuator 150 can further be actuated to discontinue power from the power source to the printed circuit board 125, and thus the at least one illumination source 88. For instance, in accordance with one embodiment, the actuator 150 can be configured as a button, though it should be appreciated that the actuator 150 can be configured as any suitable alternatively constructed actuator as desired. Furthermore, the illumination assembly 86 can include a counter 154 that allows the power to flow from the power source to the printed circuit board 125, and thus the at least one illumination source 88, for only a predetermined time duration, at which point the counter discontinues the power from the power source to the printed circuit board 125, and thus the at least one illumination source 88. The actuator 150 can again be actuated to resume the flow of power as desired. The counter can be carried anywhere by the dilator body, for instance in the handle between the actuator 150 and the electrochemical battery 152. The handle 90 can further include an end cap 169 that attaches the actuator 150 to the handle body 91.

Referring now to FIGS. 11A-11D, and as described above, the dilation member 24 can include first and second pairs 31a and 31b of opposed dilator blades 32. Each of the dilator blades 32 defines an inner surface and an outer surface opposite the inner surface. The inner surface of the of the blades 32 face the second conduit 25c, and the expansion member 34 can be rotatably coupled to the dilator blades 32 of the first pair 31 of dilator blades 32, and movable from the first position to the expanded position so as to cause the blades 32 of the second pair 31b to move the first position to the dilated position.

The at least one illumination source 88 is operable to emit illumination to at least a transparent one of the blades 32 of the second pair of blades 31b. For instance, the at least one illumination source 88 can include at least a pair of illumination sources 88 that each are carried by the printed circuit board 125 and configured to emit illumination to different ones of the blades 32 of the second pair 31b of dilator blades 32 that can each be transparent. For instance, each illumination source can be aligned with the respective blade 32 along a longitudinal direction that is substantially parallel with the longitudinal axis. In accordance with another embodiment, the illumination assembly 86 can include a first pair of illumination sources 88 aligned with the first one of the blades 32 of the second pair 31b, and a second pair of illumination sources 88 aligned with the second one of the blades 32 of the second pair 31b.

As illustrated in FIG. 11O, the blades 32 of the second pair 3 lb can be split so as to define first and second blade sections 32c and 32d that are urged to separate from each other by the expansion member 34 as the blade 32 moves from the first position to the dilated position. It should be appreciated that the first and second ones of the first pair of illumination sources 88 can be aligned with the first and second blade sections 32c and 32d, respectively, of the first blade 32. First and second ones of the second pair of illumination sources 88 can be aligned with the first and second blade sections 32c and 32d, respectively, of the second blade 32.

Figure 11H:
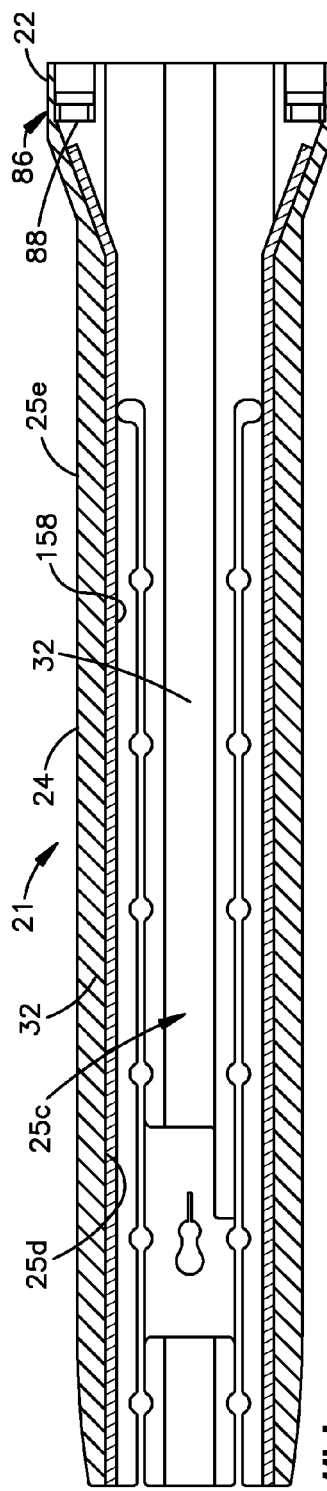
FIG. 11H is a sectional side elevation view of the dilation member of the expandable dilator as illustrated in FIG. 11G, but constructed in accordance with another embodiment.
Figure 11I:
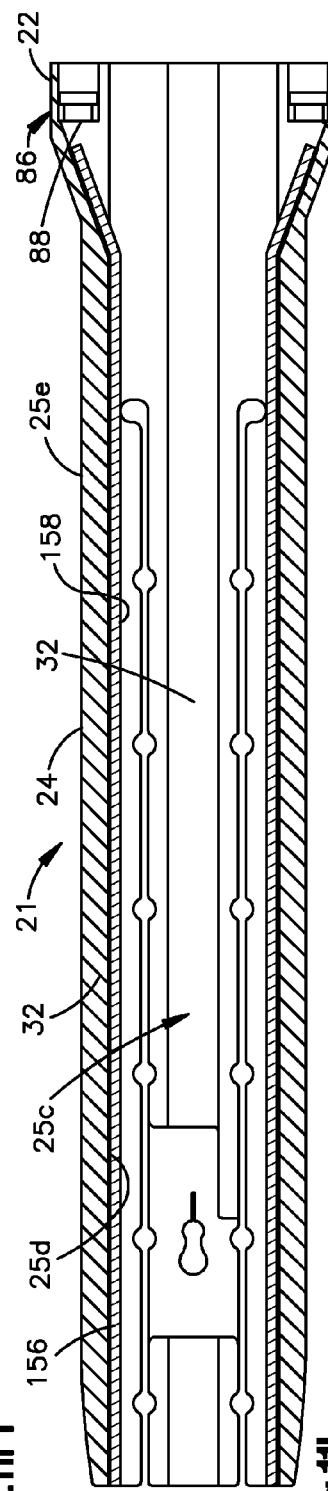
FIG. 11I is a sectional side elevation view of the dilation member of the expandable dilator as illustrated in FIG. 11H, but constructed in accordance with another embodiment.
Figure 11J:
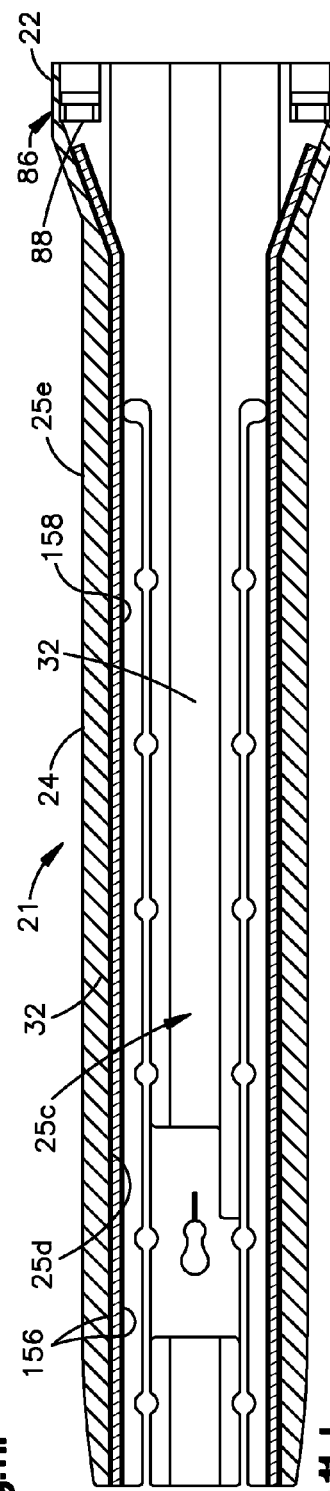
FIG. 11J is a sectional side elevation view of the dilation member of the expandable dilator as illustrated in FIG. 11I, but constructed in accordance with another embodiment.
Figure 11N:
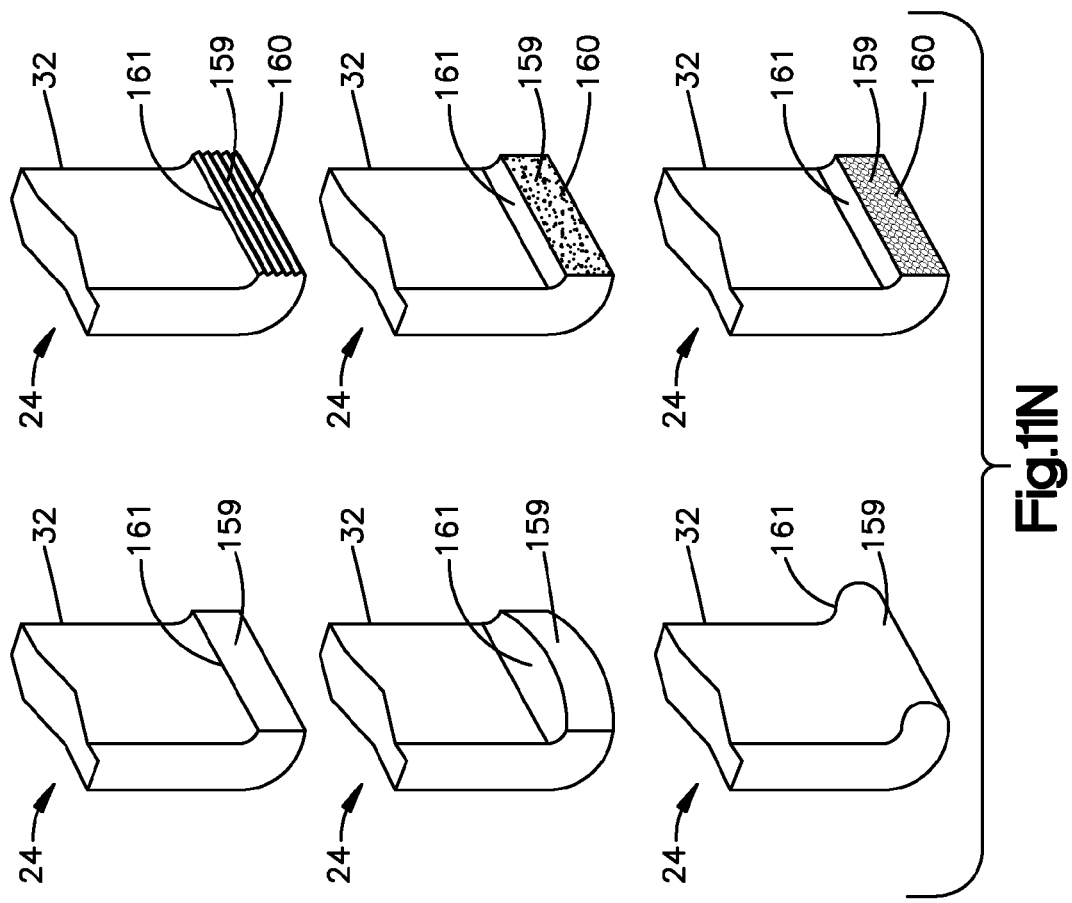
FIG. 11N shows perspective views of distal ends of inserts of the a dilation member illustrated in FIG. 11M, constructed in accordance with different embodiments.
Figure 11M:
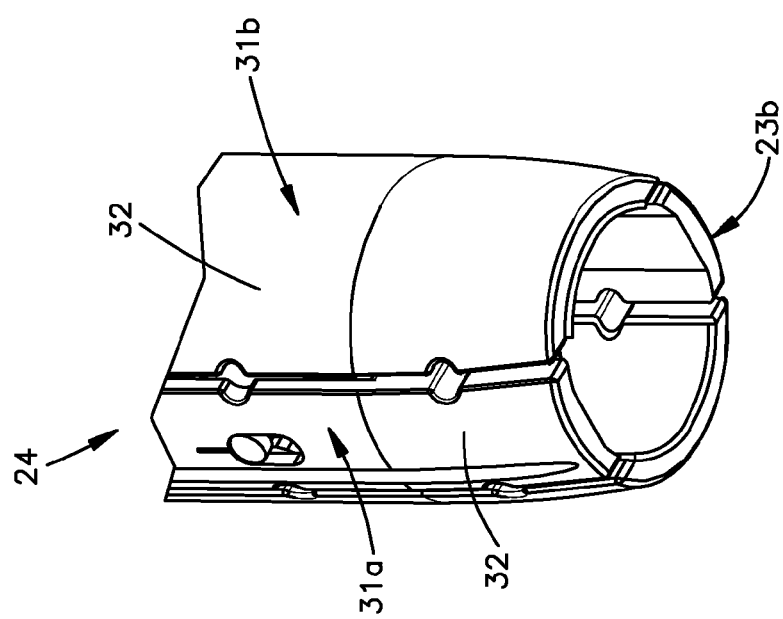
FIG. 11M is a perspective view of the distal end of a dilation member of the expandable dilator illustrated in FIG. 11A, but constructed in accordance with another embodiment.
Figure 110:
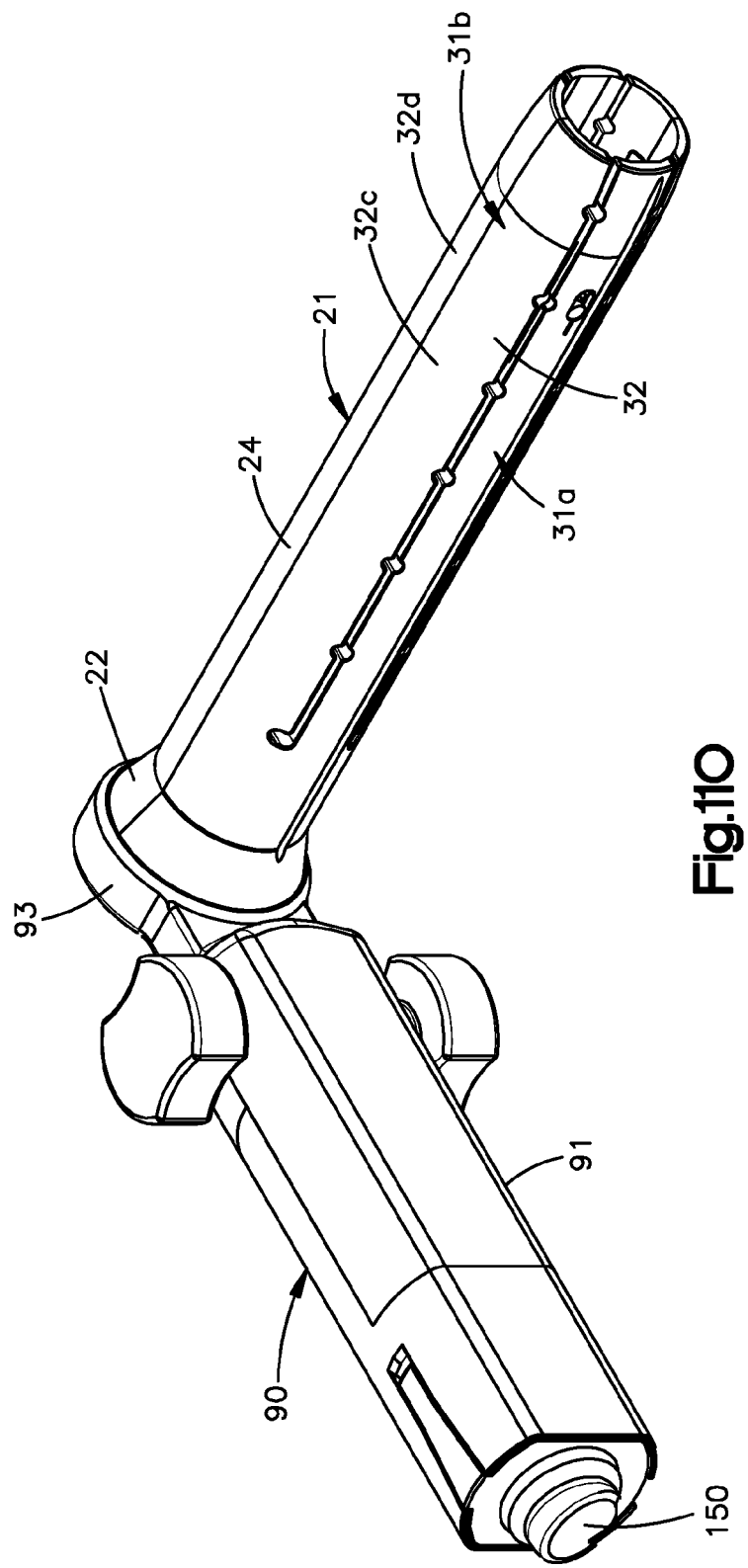
Figure 11P:
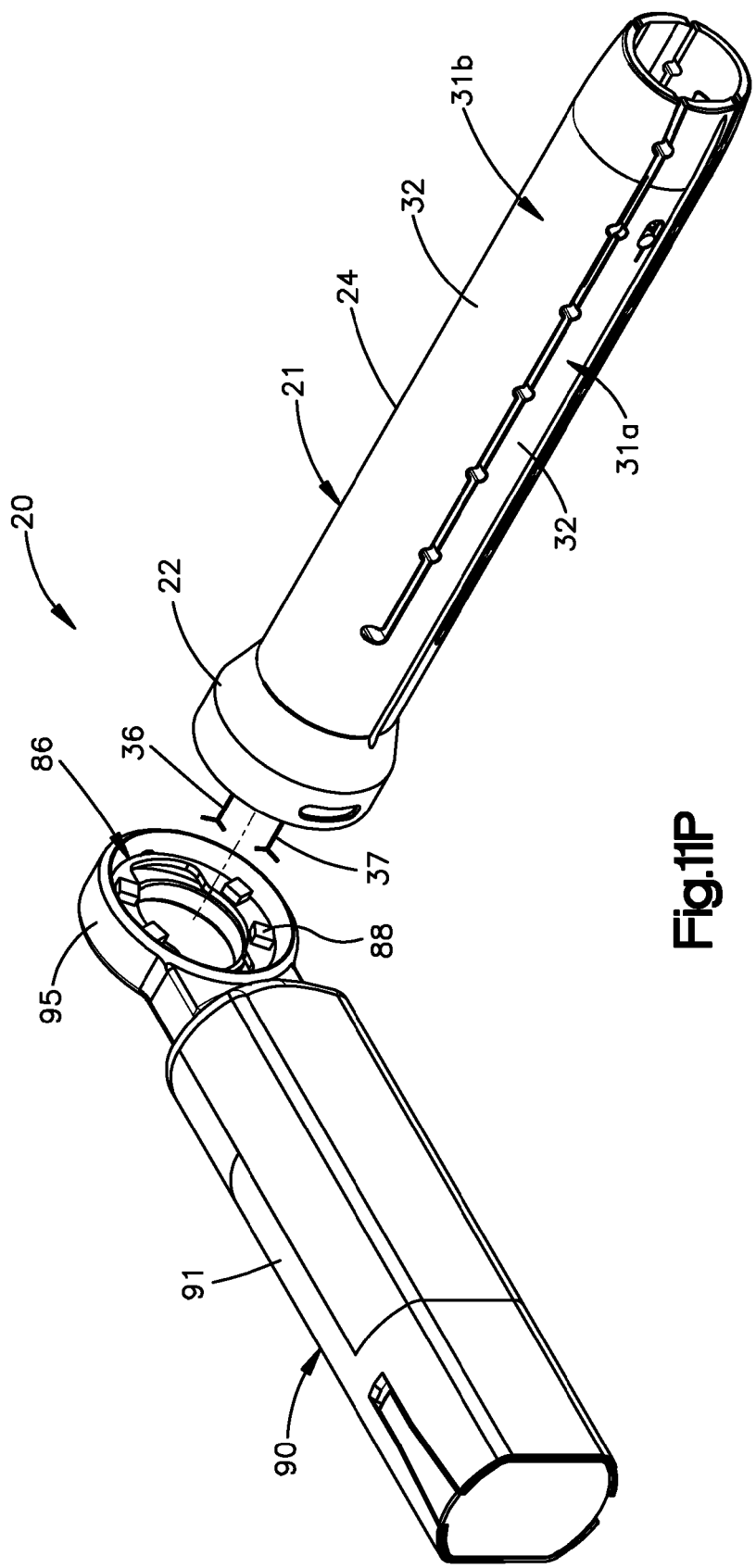
FIG. 11P is a perspective view of an expandable dilator as illustrated in FIG. 11A, but constructed in accordance with an alternative embodiment.
Figure 19A:
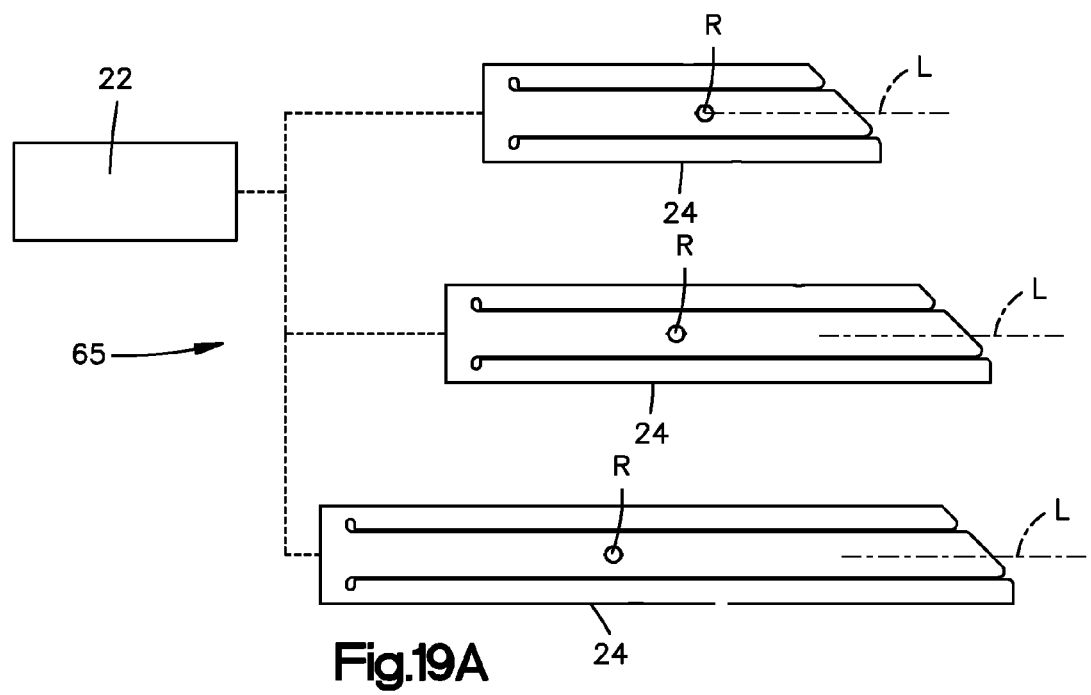
FIG. 19A is a schematic side elevation view of an expandable dilator kit including a base and a plurality of differently sized dilation members configured to be attached to the base.
Figure 19B:
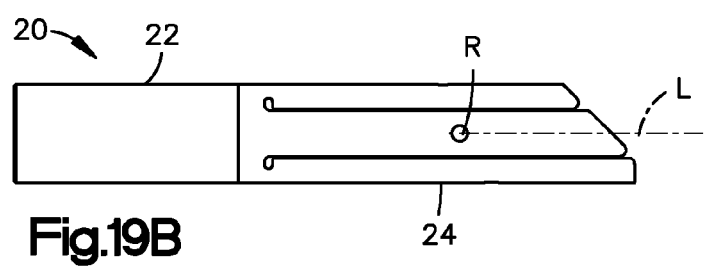
FIG. 19B is a side view of an expandable dilator including the base and one of the dilation members illustrated in FIG. 19A attached to the base.
Figure 19C:
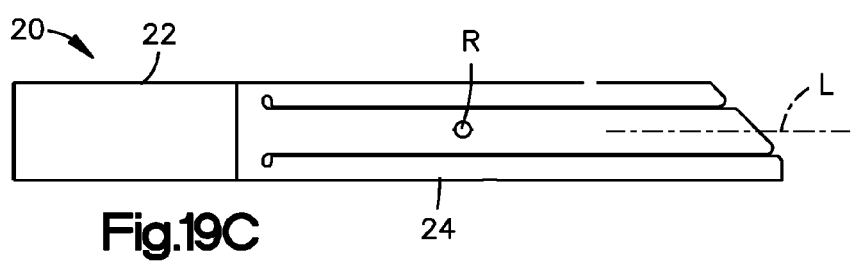
FIG. 19C is a side view of an expandable dilator including the base and another one of the dilation members illustrated in FIG. 19A attached to the base.
Figure 19D:
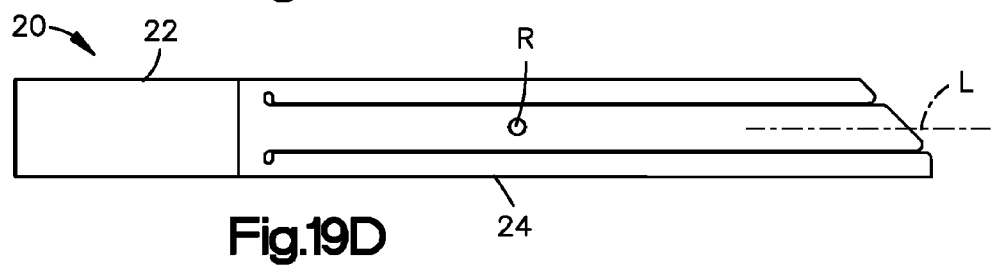
FIG. 19D is a side view of an expandable dilator including the base and yet another one of the dilation members illustrated in FIG. 19A attached to the base.

Referring to FIG. 11P, it should be appreciated that the expandable dilator 20 including the illumination assembly 86 described above can be devoid of the spool 56 illustrated in FIGS. 11A-O. In accordance with this embodiment, the expandable dilator 20 can include a single actuator 36 or a pair of actuators 36 and 37 as described above. The actuator 36 or actuators 36 and 37 can extend out the dilation body 21, such that the user can manually apply the actuation force to either or both of the actuators 36 and 37 to expand and contract the dilation member 24. In accordance with one embodiment, the actuators 36 and 37 can extend out the handle 90 or any alternative suitable structure of the expandable dilator 20. For instance, the actuators 36 and 37 can extend out the dilation body 21 along the longitudinal direction L, or along a direction angularly offset, for instance perpendicular, with respect to the longitudinal direction L.

Referring now to FIGS. 11E-11G in general, the expandable dilator 20, and in particular the dilation member 24, can include a light reflective material 156, such that illumination emitted by the illumination assembly 86 can reflect against the reflective material 156 as it is directed toward and to the distal end of the second conduit 25c. In one embodiment, the reflective material 156 can be coated onto the respective surface along which the reflective material extends. Alternatively, a reflective material 156 can be adhesively attached to the respective surface. Alternatively still, the reflective material 156 can be attached to the dilator body 21, for instance the dilation member 24, as desired such that the reflective surface is configured to direct the emitted light as desired. Furthermore, the reflective material 156 can extend along a portion of a respective surface up to all of a reflective surface, meaning that the reflective material 156 can extend along an entirety of the length of the respective surface from the proximal end to the distal end, or from a location spaced from the proximal end of the respective surface, or to a location spaced from the distal end of the respective surface. Further, the reflective material 156 can extend along a portion or all of the width of the respective surface.

As illustrated in FIG. 11E, the reflective material 156 can extend along at least a portion of the outer surface 25e of the respective blades 32 of the second pair 31b, that is the blades 32 that can be in alignment with the illumination members 88 along the longitudinal direction. Thus, the emitted illumination can reflect off the reflective material and through the respective blades 32 so as to illuminate the second conduit 25c and the transparent blades 32 as the emitted illumination is guided to the distal end. As illustrated in FIG. 11F, it is recognized that the blades 32 can be opaque, and the reflective material 156 can extend along the inner surface 25d of the respective blades of the second pair 31b. The respective illumination source 88 can be aligned with the reflective material 156, such that illumination emitted from the respective illumination source 88 reflect off the reflective material 156 so as to illuminate the second conduit 25c as the emitted illumination is guided to the distal end. As illustrated in FIG. 11G, the reflective material 156 can extend along at least a portion of the outer surface 25d of the blades 32 and the inner surface 25e of the blades 32. The blades can be transparent and aligned with the respective illumination source 88 such that the emitted illumination reflects off the reflective material 156 so as to direct the emitted illumination through the blades 32 to the distal end.

As described above, it is envisioned that the blades 32 can be made from an opaque or semi-transparent or semi-opaque material that is insufficiently transparent to guide a sufficient amount of emitted illumination to the distal end so as to illuminate the target surgical location. Thus, as illustrated in FIG. 11H, the dilator body 21, and in particular the dilation member 24, can include at least one transparent inlay 158 that is configured to receive emitted illumination from at least a respective one of the illumination sources 88, and direct the received emitted illumination toward, for instance to, the distal end. For instance, at least one of the illumination sources 28 can be aligned with a respective at least one inlay 158, for instance at the proximal end, along the longitudinal direction. In one embodiment, the transparent inlay 158 can extend along at least a portion of the inner surface 25d of a respective one of the blades 32, for instance of the second pair 31b of blades 32. The transparent inlay 158 can be coated onto the respective inner surface 25d or adhesively attached to the respective inner surface 25d. Alternatively still, the transparent inlay 158 can be attached to the dilator body 21, for instance the base 22 or the dilation member 24, as desired. Thus, an outer surface of the transparent inlay 158 can face, and can be disposed adjacent to, for instance can abut, the inner surface 25d of the respective blade 32. The inlay 158 can further defines an inner surface opposite the outer surface of the at least one inlay, the inner surface of the inlay 158 at least partially defining the second conduit 25c.

Referring now to FIGS. 11I-11L in general, the expandable dilator 20, and in particular the dilation member 24, can include a light reflective material 156, such that illumination emitted by the illumination assembly 86 can reflect against the reflective material 156 as it is directed to the distal end of the second conduit 25c. For instance, referring now to FIG. 11I, the expandable dilator 20, and in particular the dilation member 24, can include a light reflective material 156 that extends along at least a portion of the outer surface of the at least one inlay 156, for instance at a location between the outer surface of the inlay and the inner surface 25d of the respective blade 32. Thus, the reflective material 156 can be applied or attached to the outer surface of the inlay 158 or to the inner surface 25d of the corresponding blade 32. Thus, the emitted illumination can reflect off the reflective material and through the respective inlays 158 so as to illuminate the second conduit 25c and the transparent blades 32 as the emitted illumination is guided to the distal end. As illustrated in FIG. 11J, the reflective material 156 can extend along at least a portion of the outer surface of the inlay 158 and the inner surface of the inlay 158. The inlays 158 can be transparent and aligned with the respective illumination source 88 such that the emitted illumination reflects off the reflective material 156 so as to direct the emitted illumination through the inlays 158 to the distal end.

Referring now to FIGS. 11K-11L, it is recognized that both the inlays 158 and the respective blades 32 can be transparent and configured to direct the emitted light to the distal end of the second conduit 25c. For instance, as illustrated in FIG. 11K, the reflective material 156 can extend along at least a portion of the outer surface 25e of the respective blades 32 of the second pair 31b. Accordingly, one or both of the blades 32 and the respective inlays 158 can be in alignment with the illumination members 88 along the longitudinal direction. Thus, the emitted illumination can reflect off the reflective material and through the respective blades 32 and inlays so as to illuminate the second conduit 25c and the transparent blades 32 and inlays 158 as the emitted illumination is guided to the distal end of the second conduit 25c. As illustrated in FIG. 11L, the reflective material 156 can extend along at least a portion of the outer surface 25d of the blades 32 and the inner surface of the respective inlays 158. One or both of the blades 32 and the inlays 158 can be transparent and aligned with the respective illumination source 88 such that the emitted illumination reflects off the reflective material 156 so as to direct the emitted illumination through the respective blades 32 and inlays 158 to the distal end.

Referring now to FIGS. 11M-N, the distal end of the blades 32, the inlays 158, or both, can include at least one light shaping element 96 that can be supported by the respective inner surface. Thus, light shaping elements 96 described with reference to the inlays 158 can apply equally to the blades 32 unless otherwise indicated. For instance, as illustrated in FIG. 11N, the distal end of the inlay 32 can define an inner surface 159 that can face the second conduit 25c. For instance, the inner surface 159 can be defined by a lip 161 that is geometrically configured as desired and projects into the second conduit 25c, for instance at the distal end. The inner surface 159 can define any surface texture as desired, such that light reflected through the second conduit 25c can be directed through the inner surfaces 159 at the distal end, and shaped so as to direct the illumination along a direction angularly offset with respect a direction that extends from the proximal end of the at least one inlay to the distal end of the at least one inlay. Thus, the inner surfaces 159 can disperse or diffuse of the illumination at the distal end of the second conduit 25c. Alternatively, if the emitted light is guided to the distal end through a pair of spaced reflective materials 156 on opposite sides of an inlay 158, a blade 32, or combination thereof, the distal end of the respective blade or inlay 32 can define a surface texture at the inner surfaces 159 at the distal end that is configured to disperse, or diffuse, the emitted light at the distal end. In one embodiment, the inner surface 159 can define a plurality of ribs 160, which can be arranged in rows, that project inward toward the longitudinal axis of the second conduit 25c, a roughened surface 165 having raised regions on an inner surface of the inlays 32 that face the second conduit 25c, a Fresnel lens 160 on the inner surface, or any alternative suitable texture as desired.

It should be appreciated that the transparent inlay 158 and the transparent blades 32 can be made from any material such as a transparent plastic as desired, such as PA12/TR55 Grimalid or PA12/Copolyester Trogamid/Evonik or PMMA/Acrilite® MD™ material or Styrol-MMAC Copolyester/Resirene or MMA-Styrol-Ethylen/Acryl Terpolymer/Cyrolite GS90 and CG-7 or Cyclic Olefin Topas or PC/LEXAN™ Resin HPS$_4$ or PET/Eastman Tritan™ Copolyester MX17, or any suitable alternative material as desired. In accordance with one embodiment, the blades 32 and the inlays 158 are made from LEXAN™ Resin HP S$_4$.

Referring now to FIGS. 1-3D and 25A-C, it is recognized that the dilator body 21 defines a working angle defined by the longitudinal axis L and a line that extends from one side of the proximal end 21a of the dilation body 21, which can be defined by the proximal end 23a of the base 22, through the longitudinal axis L, to an opposed side of the distal end 25b of the dilation member 24 when the dilation member 24 is in the expanded configuration. It is further envisioned that the working angle can be increased by expanding the proximal end 21a of the dilator body 21. For instance, the expandable dilator 20 can include a second dilation member 27 that can be constructed substantially as described above with respect to the dilation member 24. The second dilation member 27 can extend along the proximal direction from the proximal end 23a of the base 22, and can extend from the proximal end 23a to a free end 27a. Thus, the proximal end 21a of the dilator body 21 can be defined by the proximal end of the second dilation member 27. The second dilation member 27 can include a plurality of the dilator blades 32.

The expandable dilator 20 can include a second expansion member 34a that is coupled to the second dilation member 27 and movable with respect to the second dilation member 27 from a first position to an expanded position so as to cause at least a portion of the second dilation member 27 to expand from a first configuration to an expanded configuration at a location spaced from the base 22 along the proximal direction in the manner described above with respect to the expansion member 34, thereby expanding the second dilation member 27 from the first configuration to the expanded configuration in the manner described above with respect to the dilation member 24, though it is the proximal end of the second dilation member 27 that is expanded and the distal end of the first dilation member 24 is expanded. The second dilation member 27 defines a second conduit 27b that is in fluid communication with the conduit 23c of the base 22 and the second conduit 25c.

As illustrated in FIG. 25B, the first actuator 36 can be coupled to both the first and second expansion members 34 and 34a, such that the expansion force applied to the first actuator 36 can cause both the first and second expansion members 34 and 34a to move from their respective first positions to their respective expanded positions simultaneously, in tandem. Similarly, the second actuator 37 can be coupled to both the first and second expansion members 34 and 34a, such that the contraction force applied to the second actuator 37 causes the second actuator 37 to apply a corresponding biasing force to each of the first and second expansion members 34 and 34a that causes the expansion members 34 and 34a to move from the respective expanded position to the respective first positions simultaneously, in tandem. Alternatively, as illustrated in FIG. 25C, each of the first and second expansion members 34 and 34a can be independently coupled to their own respective first and second actuators 36 and 37. Accordingly, each of the first and second expansion members 34 and 34a can be independently expanded from their respective first positions to their respective expanded positions, and independently contracted from their respective expanded positions to their respective first positions.

Referring now to FIGS. 22A-B, the expandable dilator 20 can further include a plurality of expansion members 34 coupled to the dilation member 24 and movable with respect to the dilation member 24 from respective first positions to respective expanded position so as to cause at least a portion of the dilation member to expand from the first configuration to the expanded configuration as described herein. Each of the plurality of expansion members 34 can be movable with respect to the dilation member 24 from the respective expanded positions to the respective first positions so as to cause at least a portion of the dilation member 24 to contract from the expanded configuration to the first configuration as described above. In accordance with one embodiment, the outer dimensions D2 (see FIG. 2C) of the expansion members 34 along the respective select directions SD2 can be sequentially larger as the position of the expansion members 34 is more closely spaced to the distal end 25b. Accordingly, the expansion member 34 proximate to the distal end 25b defines a respective outer dimension D2 that is greater than the outer dimension D2 of the expansion member 34 that is proximate to the base 22.

Referring to FIGS. 18A-B, it is recognized that it may be desirable to vary the length of the dilation member 24 along the longitudinal axis L. For instance, the dilation member 24, including one or more up to all of the dilator blades 32, can include a first portion 104a that extends out from the base along a distal direction, and a second portion 104b that is supported by the first portion 104a and is configured to extend out from the first portion 104 along the distal direction. The second portion 104b can define a telescopic portion that is movable with respect to the first portion 104a in the distal direction away from the base 22 so as to increase the length of the dilation member 24 along the longitudinal axis L. The expansion member 34 can be coupled to the second portion 104b as illustrated. Alternatively or additionally, an expansion member 34 can be coupled to the first portion 104a. The dilation member 24 can include any suitably constructed retention member that retains the second portion 104b in the expanded position with respect to the first portion 104a.

Figure 20A:
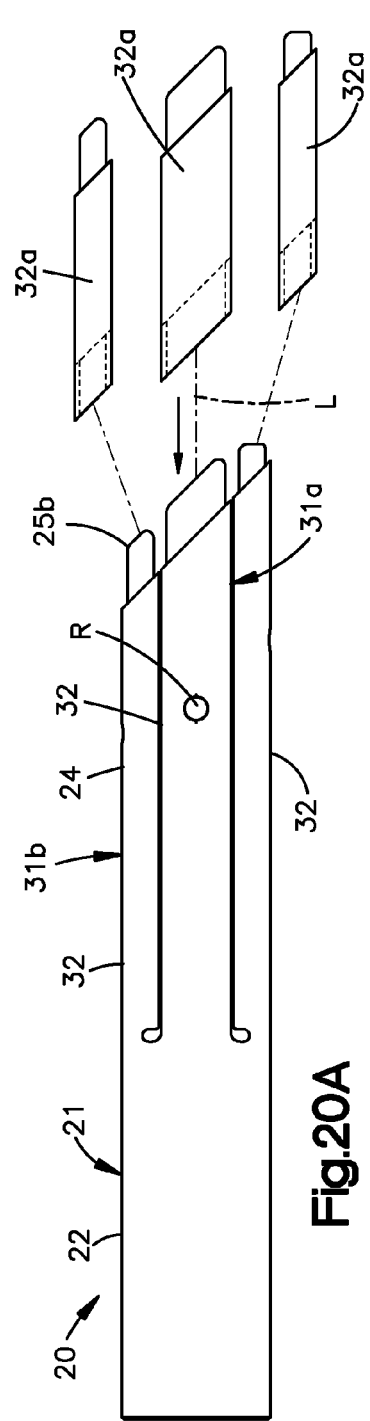
FIG. 20A is a side elevation view of the expandable dilator as illustrated in FIG. 1A, but showing modular dilator blades constructed in accordance with one embodiment.
Figure 20B:
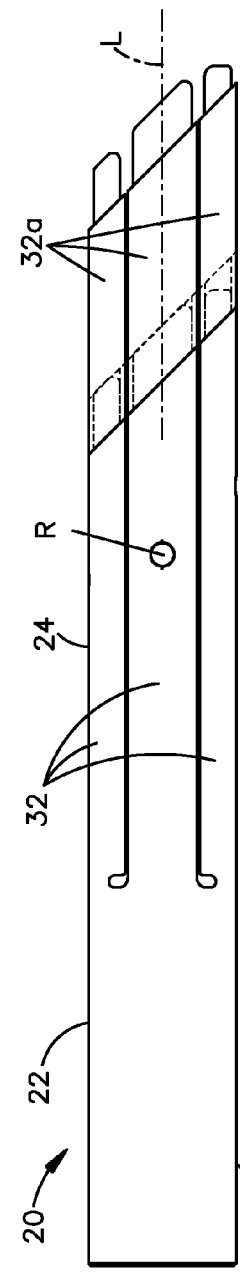
FIG. 20B is a side elevation view of the expandable dilator as illustrated in FIG. 20A, showing blade extension segments attached to the dilator blades.
Figure 20C:
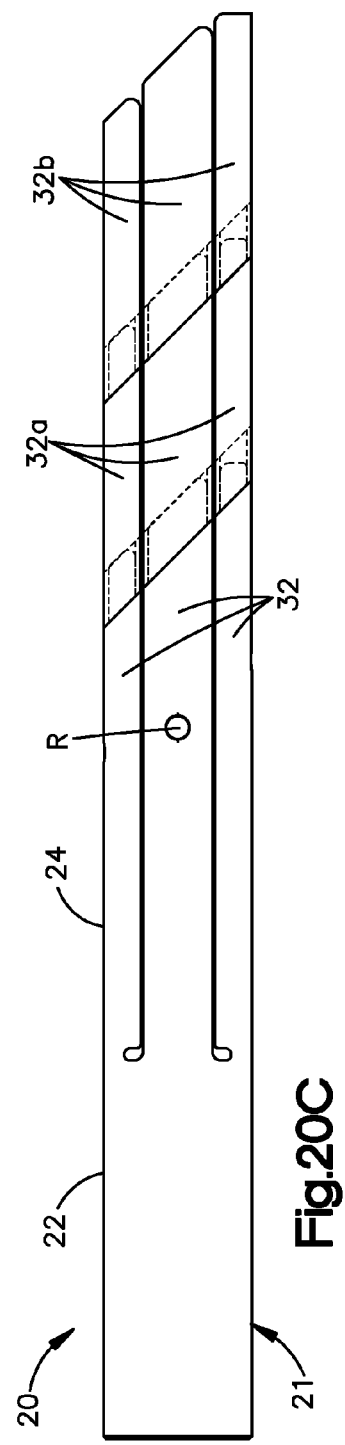
FIG. 20C is a side elevation view of the expandable dilator as illustrated in FIG. 20A, showing a second set of blade extension segments attached to the blade extension segments illustrated in FIG. 20B.
Figure 25A:
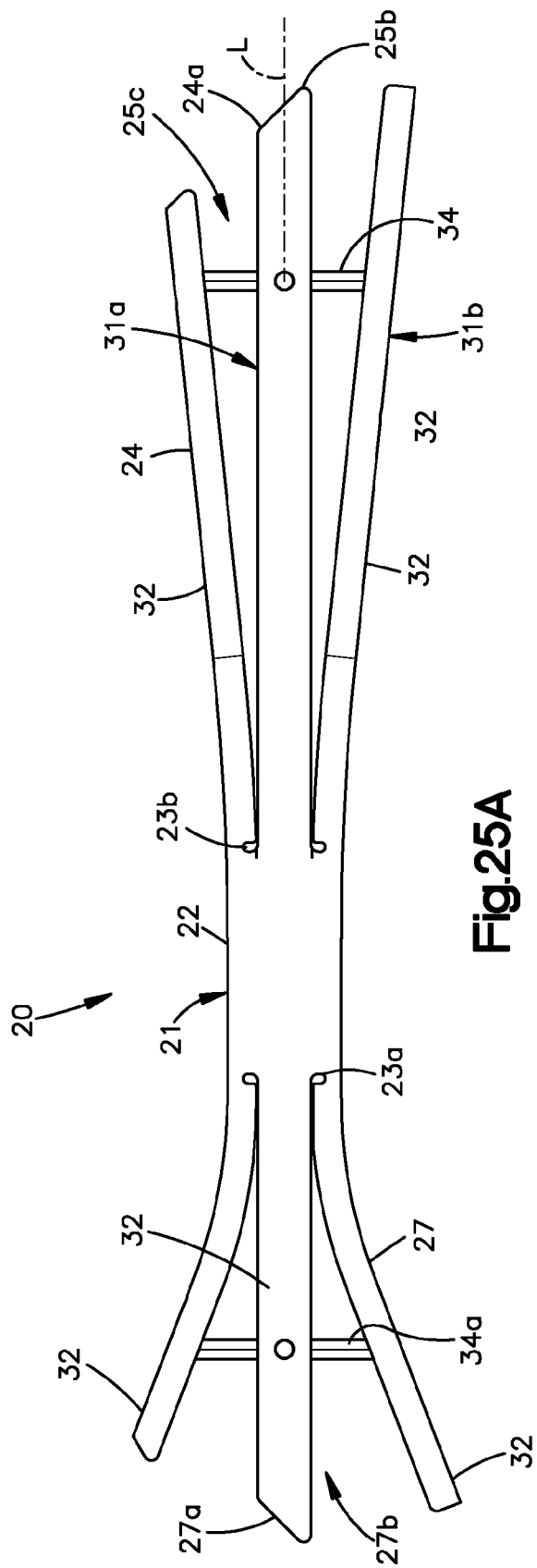
FIG. 25A is side elevation view of the expandable dilator as illustrated in FIG. 1B, but constructed in accordance with an alternative embodiment.

Alternatively, referring to FIGS. 20A-C, the dilation member 24, and thus the expandable dilator 20, can include a plurality of blade extension segments 32a configured to be removably attached to the distal ends 25b of respective ones of the dilator blades 32. For instance, as illustrated in FIGS. 20A-B, the distal ends 25b of the dilator blades 32 can define respective first attachment members, and the blade extension segments 32a can define complementary second attachment members that are configured to removably attach to the first attachment members so as to increase the length of the dilation member 24 along the longitudinal axis L. Furthermore, as illustrated in FIG. 20C, the dilation member 24, and thus the expandable dilator 20, can include a second plurality of blade extension segments 32b that are removably attachable to the distal ends of the first plurality of blade extension segments 32a. For instance, the distal ends 25b of the first plurality of blade extension segments 32a can define respective first attachment members, and each of the second plurality of blade extension segments 32a can define complementary second attachment members that are configured to removably attach to the first attachment members of the blade extension segments 32a so as to further increase the length of the dilation member 24 along the longitudinal axis L. The blade extension segments 32a and 32b can define any length along the longitudinal axis L as desired.

Referring to FIG. 24, an expandable dilator assembly 64 can include the expandable dilator 20 as recited in any one of the preceding claims, and a support frame 120. The support frame 120 has a first attachment end 120a configured to be coupled to a support structure, such as an operating table, a second attachment end 120b configured to be coupled to the expandable dilator 20, for instance to the base 22, and a plurality of linkages 120c joined at respective joints between the first and second attachment ends 120a and 120b. One or more of the linkages 120c are configured to articulate with respect to others of the linkages 120c, such that the first and second attachment ends 120a and 120b are movable with respect to each other in six degrees of freedom. The expandable dilator assembly 64 can further include a handle 126 that extends out from the dilator body 21, for instance at the base 22. Forces can be applied, for instance manually, to the handle 126 so as to move the expandable dilator relative to the support structure in six degrees of freedom as permitted by the support frame 120.

Referring now to FIGS. 21A-B, it is also recognized that it may be desirable to decrease the length of the dilation member 24 along the longitudinal axis L. Accordingly, an expandable dilator assembly 64 can include the expandable dilator 20 in accordance with any embodiment described herein, and a cutter assembly 106 that is configured to sever the dilation member at a location between the base and the free end so as to define the distal end 25b at a location spaced closer to the base 22. For instance, the dilation member 24 can defines at least one perforation 108, such as a plurality of perforations 108 that define a sever location at which the cutter assembly 106 is configured to sever the dilation member 24. In accordance with one embodiment, the cutter assembly 106 can include an anvil 110 that is configured to be inserted into the second conduit 25c, and a cutting blade 112 that is configured to be driven through the anvil 110 and the dilation member 24 so as to sever the dilation member 24.

As an alternative or in addition to adjusting the length of the dilation member 24, a kit 65 can provide for expandable dilators 20 having at least a different size or shape with respect to others of expandable dilators 20. For instance, as illustrated in FIG. 17, the kit 65 can include a plurality of expandable dilators 20 constructed in accordance with any embodiment described herein. The dilation members 24 of each of the plurality of expandable dilators 20 of the kit 65 can have a different size or shape with respect to the dilation members of at least one of the other of the plurality of expandable dilators 20 of the kit. For instance, the dilation members 24 of each of the plurality of expandable dilators 20 of the kit 65 can have a different length along the longitudinal axis L and/or a different cross-sectional dimension along the select direction SD1 with respect to the dilation members 24 of at least one of the other of the plurality of expandable dilators 20 of the kit. Alternatively or additionally, the longitudinal axis L of the dilation members 24 of each of the plurality of expandable dilators 20 of the kit 65 can have a different shape (e.g., straight, curved, or the like) with respect to the dilation members of at least one of the other of the plurality of expandable dilators 20 of the kit.

Referring now to FIGS. 19A-D, the kit 65 can additionally or alternatively include a plurality of dilation members 24 that are removably attachable to the base 22. For instance, the base 22 can define a first attachment member and the dilation members 24 can define a complementary second attachment member that is configured to attach, for instance removably attach, to the first attachment member. The dilation members 24 of the kit 65 can have a different size or shape with respect to of at least one of the other of the plurality of dilation members 24 of the kit 65. For instance, each of the plurality of dilation members 24 of the kit 65 can define a different length along the longitudinal axis L and/or a different cross-sectional dimension along the select direction SD1 with respect to at least one of the other of the plurality of dilation members 24 of the kit 65. Alternatively or additionally, the longitudinal axis L of each of the plurality of dilation members 24 of the kit 65 can have a different shape (e.g., straight, curved, or the like) with respect to at least one of the other of the plurality of dilation members 24 of the kit.

It should be appreciated that methods for dilating soft tissue can be provided by the expandable dilator, the dilation assemblies 64 disclosed herein, and the kits 65 disclosed herein. For instance one method of dilating soft tissue can include the steps of 1) creating an incision into a dermal layer, 2) inserting a dilation member through the dermal layer into soft tissue behind the dermal layer until a free end of the dilation member is positioned adjacent a target surgical site, such that a base traverses the dermal layer, wherein the dilation member extends from the base, and 3) actuating an expansion member coupled to the dilation member to move with respect to the dilation member from a first position to an expanded position, thereby maintaining at least a portion of the dilation member in an expanded configuration from a first configuration to an expanded configuration along a direction of expansion that is angularly offset with respect to a longitudinal axis of the dilation member.

The method can further include the step of applying a biasing force to an actuator that extends from the expansion member so as to actuate the expansion member from the first position to the expanded position. The applying step can further include the step of applying the biasing force along a direction from the dilation member toward the base. The method can further include the step of securing the actuator when the expansion member is in the expanded position. The method can further include the step of illuminating an illumination source that is supported by the base so as to illuminate the free end of the dilation member. The actuating step can include the step of rotating the expansion member about an axis of rotation. The method can further include the step of actuating at least one of the dilator blades away from another one of the dilator blades. The actuating step can further include the step of expanding the dilation member from the first configuration to the expanded configuration. The method can further include the steps of inserting an auxiliary expansion member into a conduit defined by the dilation member, and expanding the auxiliary expansion member so as to expand the dilation member from the first configuration to the expanded configuration. After the step of expanding the auxiliary expansion member, the method can include the step of actuating the expansion member from the first position to the expanded position. After the actuating step, the method can further include the step of returning the auxiliary expansion member to the first position and removing the auxiliary expansion member from the conduit while the expansion member maintains the dilation member in the expanded configuration. The method can further include the step of actuating the expansion member from the expanded position at least toward the first position, thereby returning the dilation member from the expanded configuration to the first configuration, and removing the expandable dilator from the soft tissue and the dermal layer. The inserting step can further include inserting the dilator to a position adjacent an intervertebral space along a lateral transpsoas approach.

The foregoing description is provided for the purpose of explanation and is not to be construed as limiting the invention. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the invention is not intended to be limited to the particulars disclosed herein. For instance, it should be appreciated that structure and methods described in association with one embodiment are equally applicable to all other embodiments described herein unless otherwise indicated. Those skilled in the relevant art, having the benefit of the teachings of this specification, may effect numerous modifications to the invention as described herein, and changes may be made without departing from the spirit and scope of the invention, for instance as set forth by the appended claims.

What is claimed:

1. An expandable dilator configured to dilate soft tissue, the expandable dilator comprising:
   a base defining an outer surface and an inner surface opposite the outer surface, the inner surface at least partially defining a first conduit;
   a dilation member that extends from the base, the dilation member defining an inner surface and an outer surface opposite the inner surface, wherein the inner surface of the dilation member at least partially defines a second conduit in fluid communication with the first conduit, the second conduit elongate along a longitudinal axis; and
   an expansion member coupled to the dilation member at first and second locations spaced from each other along an axis of rotation, and rotatable with respect to the dilation member about the axis of rotation from a first position to an expanded position, wherein as the expansion member moves from the first position to the expanded position, first and second bearing surfaces of the expansion member that are disposed on opposite sides of the axis of rotation are configured to bear against the dilation member so as to urge at least a portion of the dilation member to expand from a first configuration to an expanded configuration along a direction of expansion that is angularly offset with respect to the longitudinal axis,
   wherein rotation of the first bearing surface about the axis or rotation causes the second bearing surface also rotate about the axis of rotation.

2. The expandable dilator as recited in claim 1, wherein the portion of the expansion member is disposed between the first and second locations.

3. The expandable dilator as recited in claim 2, wherein the expansion member defines a first outer dimension along the axis of rotation from the first location to the second location, and a second outer dimension along a select direction that is angularly offset from the axis of rotation, the second outer dimension greater than the first outer dimension.

4. The expandable dilator as recited in claim 1, wherein the expansion member defines an outer perimeter that abuts at least a portion of the inner surface of the dilation member when the expansion member is in the expanded position.

5. The expandable dilator as recited in claim 1, wherein the dilation member defines at least one stop surface that is configured to abut the expansion member when the expansion member has rotated to the expanded position.

6. The expandable dilator as recited in claim 1, wherein the dilation member comprises at least first and second dilator blades, and at least one of the first and second dilator blades receives a biasing force from the expansion member that urges the at least one of the first and second dilator blades to move from a first position away from the other of the first and second dilator blades to a dilated position that defines the expanded configuration.

7. The expandable dilator as recited in claim 1, wherein the dilation member comprises first and second pairs of opposed dilator blades, and the expansion member is rotatably attached to at least one or both of the first pair of dilator blades, such that the expansion member biases at least one or both of the second pair of dilator blades from the first position to the dilated position as the expansion member moves from the first position to the expanded position.

8. The expandable dilator as recited in claim 1, further comprising an actuator coupled to the expansion member, the actuator configured to apply a biasing force to the expansion member that causes the expansion member to move from the first position to the expanded position.

9. The expandable dilator as recited in claim 8, wherein the actuator is monolithic with the expansion member.

10. The expandable dilator as recited in claim 8, wherein the actuator is separate from the expansion member and coupled to the expansion member.

11. The expandable dilator as recited in claim 8, further comprising a dilator body that includes the base and the dilation member, and a securement member that is supported by the dilator body, the securement member configured to attach to the actuator so as to prevent the actuator from moving in a direction from the base toward the dilation member, thereby retaining the expansion member in the expanded position.

12. The expandable dilator as recited in claim 11, wherein the securement member comprises one of a cleat supported by the dilator body, a set screw threadedly supported by the dilator body, and a clamp supported by the dilator body.

13. The expandable dilator as recited in claim 8, further comprising a second actuator configured to apply a biasing force to the expansion member that causes the expansion member to move from the expanded position to the first position.

14. The expandable dilator as recited in claim 8, further comprising an actuation leverage member attached to the actuator, wherein the leverage member is configured to receive a force, alter the force, and apply the altered force through the actuator to the expansion member to move the expansion member from the first position toward the expanded position.

15. The expandable dilator as recited in claim 1, further comprising a dilator body that includes the base and the dilation member that extends out from the base to a distal end, and at least one illumination source supported by the dilator body, the illumination source configured to emit illumination to the second conduit at the distal end and out the distal end of the second conduit.

16. The expandable dilator as recited in claim 15, wherein the distal end of the dilation member defines at least one light shaping element that comprises at least one of 1) a plurality of prisms supported by the inner surface at the distal end, 2) a roughened region of the inner surface at the distal end, and 3) a reflective material supported by the inner surface at the distal end.

17. The expandable dilator as recited in claim 1, wherein the dilation member is resiliently flexible and extends from the base to a distal end, the expandable dilator further comprising:
 a track supported by the dilation member, the track extending between the base and the distal end; and
 an expansion device slidable along the track, the expansion device having a cross-sectional dimension greater than that of the second conduit, such that the expansion device dilates the dilation member from the first configuration to the expanded configuration at a region local to the expansion device.

18. The expandable dilator as recited in claim 1, wherein the axis of rotation intersects the longitudinal axis.

19. The expandable dilator as recited in claim 1, wherein the expansion member has a shape that remains constant both in the first position and in the expanded position.

20. An expandable dilator configured to dilate soft tissue, the expandable dilator comprising:
 a base defining an outer surface and an inner surface opposite the outer surface, the inner surface at least partially defining a first conduit;
 a dilation member that extends from the base, the dilation member defining an inner surface and an outer surface opposite the inner surface, wherein the inner surface of the dilation member at least partially defines a second conduit in fluid communication with the first conduit, the second conduit elongate along a longitudinal axis; and
 an expansion member coupled to the dilation member at first and second locations spaced from each other along an axis of rotation, and rotatable with respect to the dilation member about the axis of rotation from a first position to an expanded position so as to cause at least a portion of the dilation member to expand from a first configuration to an expanded configuration along a direction of expansion that is angularly offset with respect to the longitudinal axis;
 an actuator coupled to the expansion member, the actuator configured to apply a biasing force to the expansion member that causes the expansion member to move from the first position to the expanded position; and
 an actuation leverage member attached to the actuator, wherein the leverage member is configured to receive a force, alter the force, and apply the altered force through the actuator to the expansion member to move the expansion member from the first position toward the expanded position, wherein the actuation leverage member comprises a spool that is attached to the actuator, the spool including a spool body that is rotatable in a first rotational direction so as to cause the actuator to wind around the spool body, thereby causing the expansion member to move from the first position toward the expanded position.

21. The expandable dilator as recited in claim 20, further comprising a dilator body that includes the base and the dilation member that extends out from the base, wherein the actuation leverage member and the dilator body each includes a locking member configured to engage each other so as to prevent the spool from rotating with respect to the dilator body.

\* \* \* \* \*